United States Patent
Yoshimura et al.

(10) Patent No.: US 10,881,734 B2
(45) Date of Patent: Jan. 5, 2021

(54) MONOCLONAL ANTIBODIES TO HUMAN FIBROBLAST GROWTH FACTOR RECEPTOR 2 (HFGFR2) AND METHODS OF USE THEREOF

(71) Applicant: DAIICHI SANKYO COMPANY, LIMITED, Tokyo (JP)

(72) Inventors: Chigusa Yoshimura, Tokyo (JP); Reimi Kawaida, Tokyo (JP); Kokichi Honda, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/567,936

(22) PCT Filed: Apr. 19, 2016

(86) PCT No.: PCT/JP2016/062297
§ 371 (c)(1),
(2) Date: Oct. 19, 2017

(87) PCT Pub. No.: WO2016/171107
PCT Pub. Date: Oct. 27, 2016

(65) Prior Publication Data
US 2018/0133314 A1 May 17, 2018

(30) Foreign Application Priority Data
Apr. 20, 2015 (JP) .................... 2015-085942

(51) Int. Cl.
| | |
|---|---|
| A61K 39/395 | (2006.01) |
| G01N 33/577 | (2006.01) |
| A61P 35/00 | (2006.01) |
| C07K 16/28 | (2006.01) |
| G01N 33/68 | (2006.01) |
| C12N 5/10 | (2006.01) |
| C12N 15/09 | (2006.01) |

(52) U.S. Cl.
CPC ........ *A61K 39/39558* (2013.01); *A61P 35/00* (2018.01); *C07K 16/2863* (2013.01); *C12N 5/10* (2013.01); *C12N 15/09* (2013.01); *G01N 33/577* (2013.01); *G01N 33/6893* (2013.01); *C07K 2317/24* (2013.01); *C07K 2317/33* (2013.01); *C07K 2317/51* (2013.01); *C07K 2317/565* (2013.01); *C07K 2317/76* (2013.01); *G01N 2333/503* (2013.01)

(58) Field of Classification Search
CPC ........ A61K 39/39558; G01N 33/6893; G01N 33/577; G01N 2333/503; C07K 16/2863; C07K 2317/24; C07K 2317/33; C07K 2317/51; C07K 2317/565; C07K 2317/76; A61P 35/00; C12N 5/10; C12N 15/09
See application file for complete search history.

(56) References Cited

U.S. PATENT DOCUMENTS

2013/0142802 A1 6/2013 Chang et al.
2015/0125454 A1* 5/2015 Ohtsuka ............. C07K 16/2863
424/139.1

FOREIGN PATENT DOCUMENTS

| WO | WO-2010/054265 A2 | 5/2010 |
| WO | WO-2013/076186 A1 | 5/2013 |
| WO | WO-2013-154206 | 10/2013 |
| WO | WO-2014-089193 A1 | 6/2014 |
| WO | WO-2014/160160 A2 | 10/2014 |
| WO | WO-2015/017600 A1 | 2/2015 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Lloyd C, et al. (2009). Protein Engineering, Design & Selection. 22(3):159-168. doi:10.1093/protein/gzn058.*
Eswarakumar et al, Cellular signaling by fibroblast growth factor receptors, Cytokine & Growth Factor Reviews, 2005, pp. 139-149.
Turner et al, Fibroblast growth factor signaling: from development to cancer, Cancer, 2010, vol. 10, No. 2, pp. 116, 129.
Easton et al, Genome-wide association study identifies novel breast cancer susceptibility loci, Jun. 28, 2007, vol. 447 (No. 7148), p. 1087-1093.
Hunter et al, A genome-wide association study identifies alleles in FGFR2 associated with risk of sporadic postmenopausal breast cancer, Nat. Genet, 2007, vol. 39, No. 7, pp. 870-874.
Katoh et al, FGFR2-related pathogenesis and FGFR2-targeted therapeutics (Review), International Journal of Molecular Medicine, 2008, vol. 23, pp. 307-311.
Chaffer et al, Aberrant fibroblast growth factor receptor signaling in bladder and other cancers, Differentiation, 2007, vol. 75, pp. 831-842.
Carstens et al, Alternative splicing of fibroblast growth factor receptor 2 (FGF-R2) in human prostate cancer, Oncogene, 1997, vol. 15, pp. 3059-3065.
Zhao et al, Monoclonal Antibodies to Fibroblast Growth Factor Receptor 2 Effectively Inhibit Growth of Gastric Tumor Xenografts, Clinical Cancer Research, 2010, vol. 16, pp. 5750-5758.
Bai et al, GP369, an FGFR2-IIIb—Specific Antibody, Exhibits Potent Antitumor Activity against Human Cancers Driven by Activated FGFR2 Signaling, Cancer Research, 2010, vol. 70, pp. 7630-7639.
Clinical Trials. gov, Clinical Trials.gov Identifier: NCT01881217, published online on Jun. 13, 2013.
Clinical Trials. gov, Clinical Trials. gov Identifier: NCT02368951, published online on Feb. 16, 2015.

(Continued)

*Primary Examiner* — Robert S Landsman
(74) *Attorney, Agent, or Firm* — Foley & Lardner LLP

(57) ABSTRACT

The present invention provides a pharmaceutical composition or a diagnostic composition targeting human fibroblast growth factor receptor 2 (hFGFR2).

21 Claims, 28 Drawing Sheets
Specification includes a Sequence Listing.

(56) References Cited

OTHER PUBLICATIONS

Vermeulen et al, Differential Expression of Growth Factor Receptors and Membrane-Bound Tumor Markers for Imaging in Male and Female Breast Cancer, PLOS One, 2013, vol. 8.

Partial European Search Report dated Nov. 16, 2018 in corresponding application No. 16783128.8.

Ohashi et al, Downregulation of fibroblast growth factor receptor 2 and its isoforms correlates with a high proliferation rate and poor prognosis in high-grade glioma, Oncology Reports, 2014, pp. 1163-1169.

Extended European Search Report dated Feb. 25, 2019 in corresponding application No. 16783128.8.

Wei et a, Generation and Characterization of Monoclonal Antibodies to Human Keratinocyte Growth Factor Receptor, Hybridoma, 2006, vol. 25, No. 3.

Matsuda, Y., et al., "Fibroblast Growth Factor Receptor 2 IIIc as a Therapeutic Target for Colorectal Cancer Cells," Molecular Cancer Therapeutics, dated Sep. 2012, pp. 2010-2020.

Matsuda, Y., et al., "Fibroblast Growth Factor Receptor 2: Expression, Roles, and Potential as a Novel Molecular Target for Colorectal Cancer," Pathology Research International, vol. 2012, dated Mar. 28, 2012, pp. 1-8.

Ishiwata, T., et al., "Enhanced Expression of Fibroblast Growth Factor Receptor 2 IIIc Promotes Human Pancreatic Cancer Cell Proliferation," The American Journal of Pathology, vol. 180, No. 5, dated May 2012, pp. 1928-1941.

Ueda, J., et al., "Epithelial splicing regulatory protein 1 is a favorable prognostic factor in pancreatic cancer that attenuates pancreatic metastases," Oncogene, vol. 33, dated Sep. 30, 2013, pp. 4485-4495.

\* cited by examiner

[Figure 1]
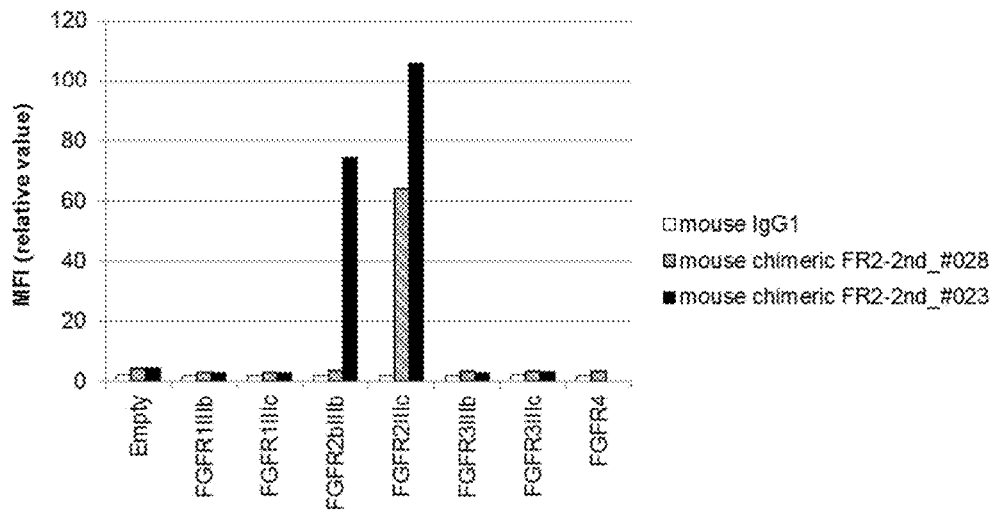
[Figure 2A]
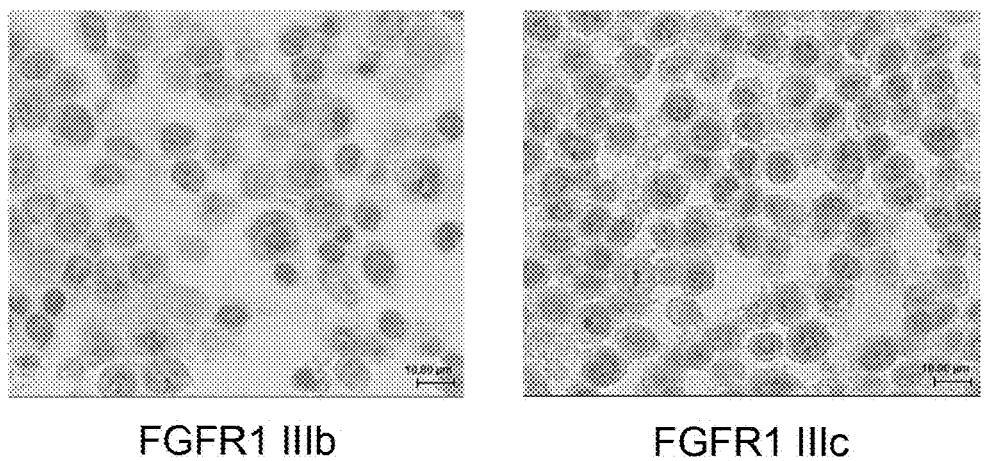
FGFR1 IIIb    FGFR1 IIIc
[Figure 2B]
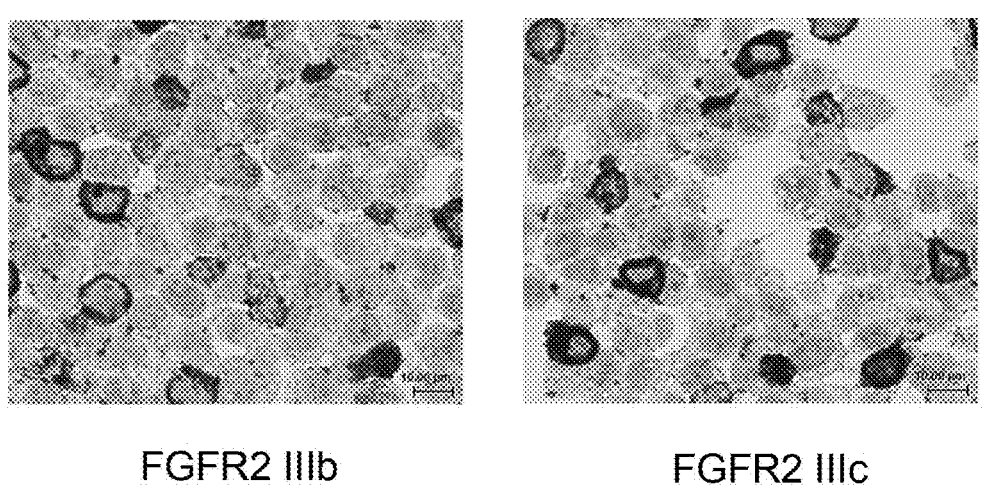
FGFR2 IIIb    FGFR2 IIIc

[Figure 2C]
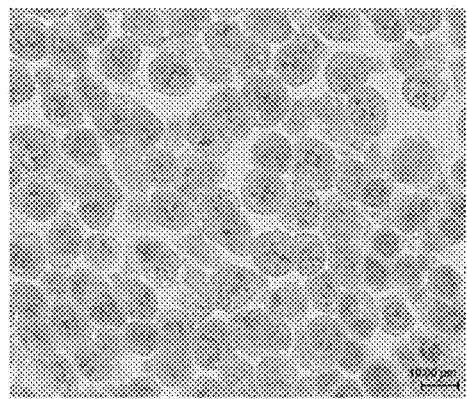
FGFR3 IIIb
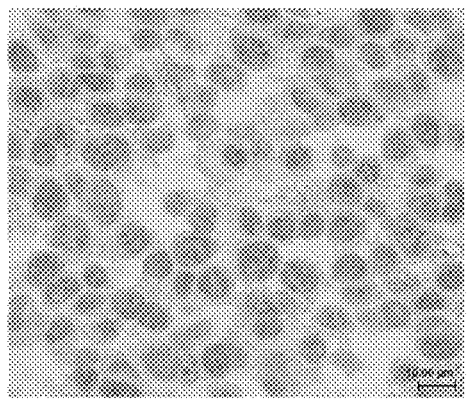
FGFR3 IIIc
[Figure 2D]
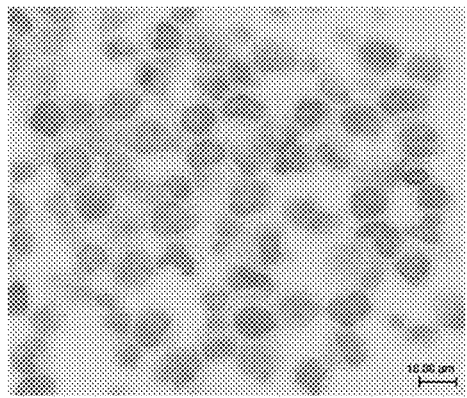
FGFR4
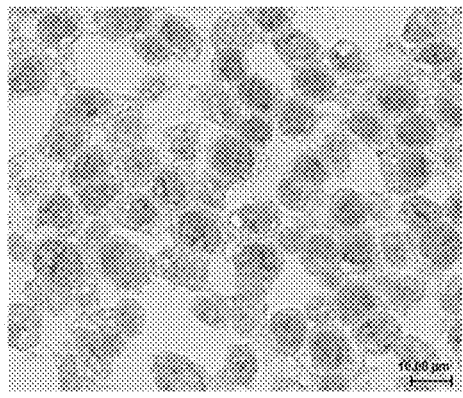
Vector

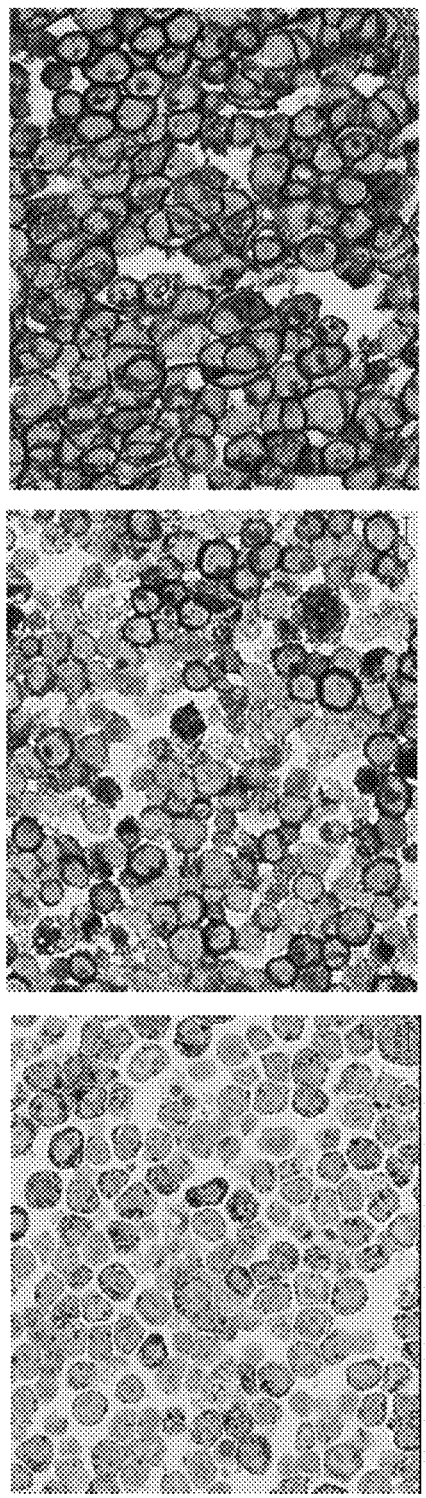
[Figure 3]

[Figure 4A]
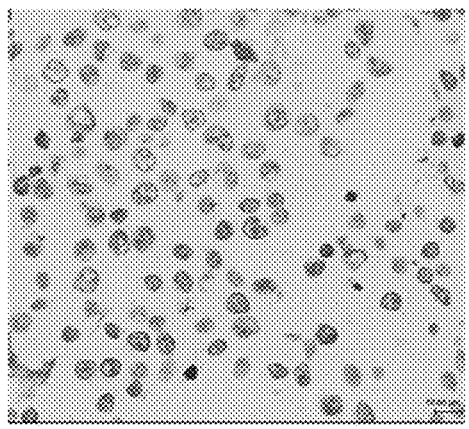
FGFR1 IIIb
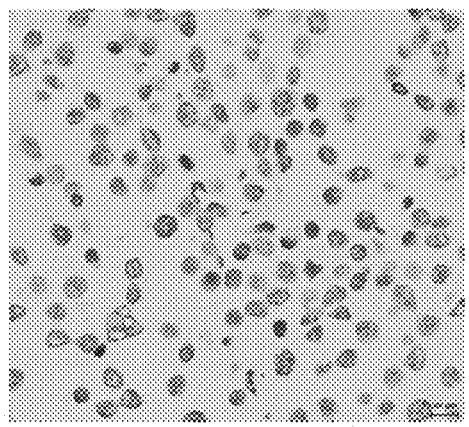
FGFR1 IIIc
[Figure 4B]
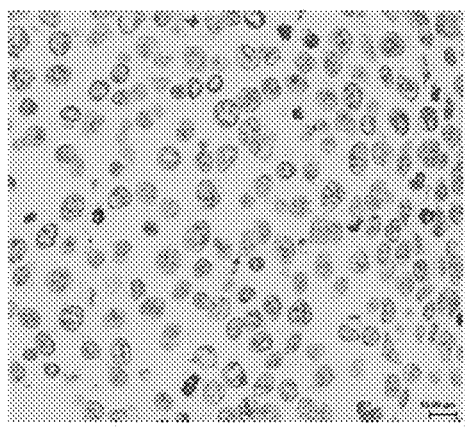
FGFR2 IIIb
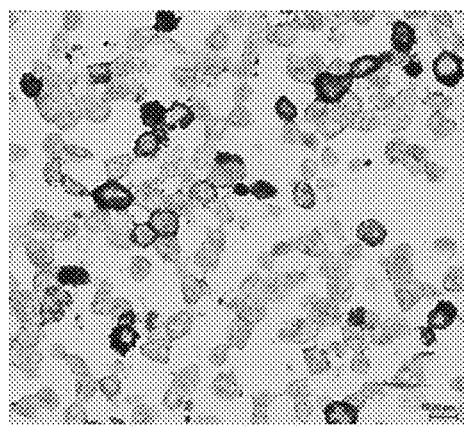
FGFR2 IIIc

[Figure 4C]
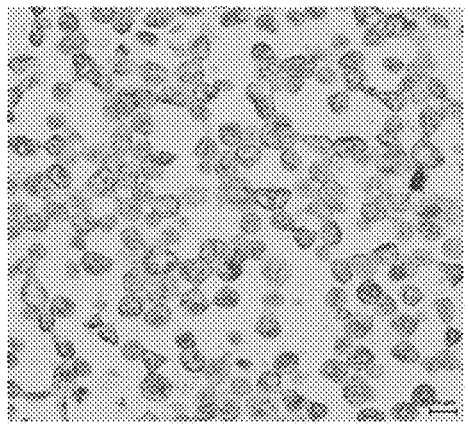
FGFR3 IIIb
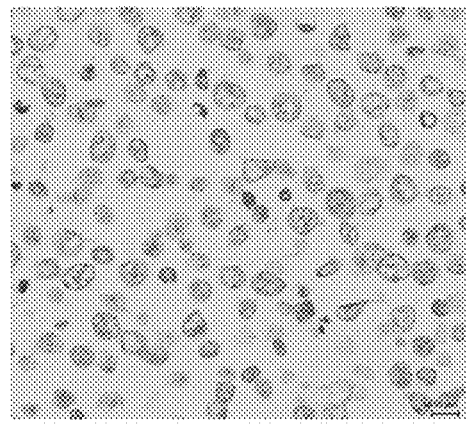
FGFR3 IIIc
[Figure 4D]
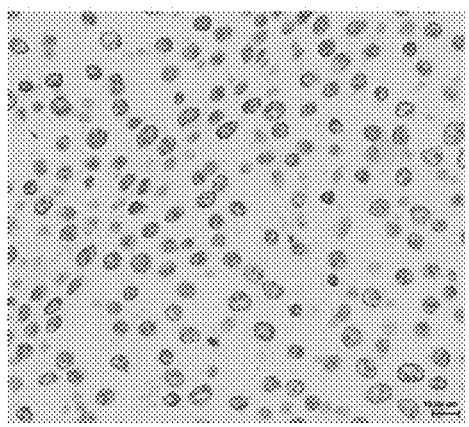
FGFR4
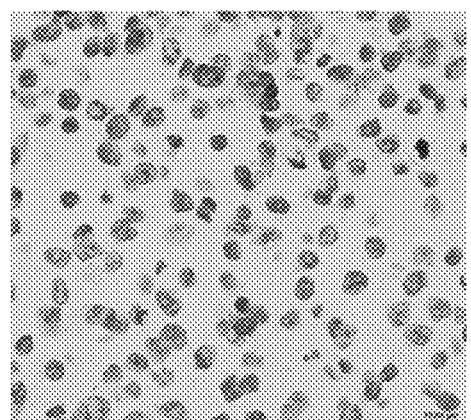
Vector

[Figure 5A]
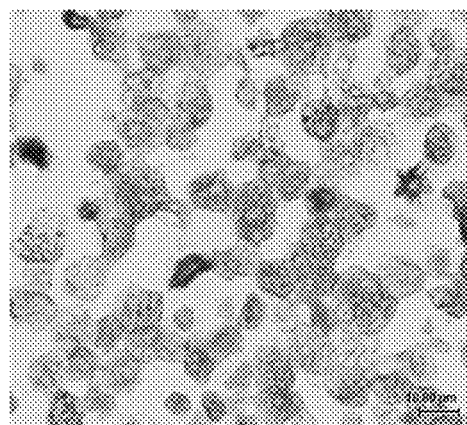 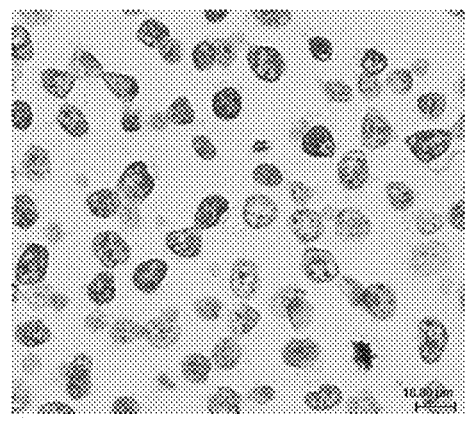
FGFR1 IIIb            FGFR1 IIIc
[Figure 5B]
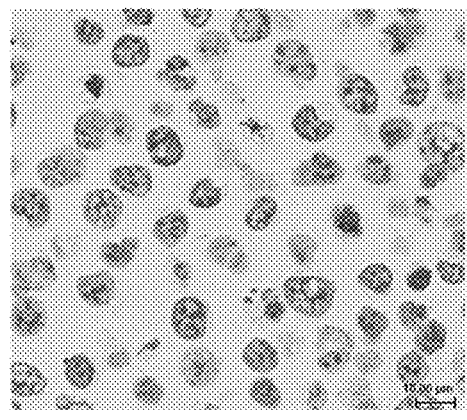 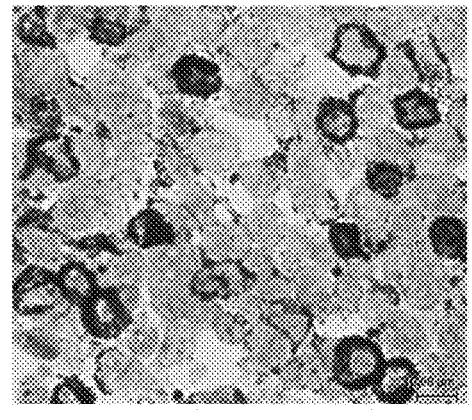
FGFR2 IIIb            FGFR2 IIIc

[Figure 5C]
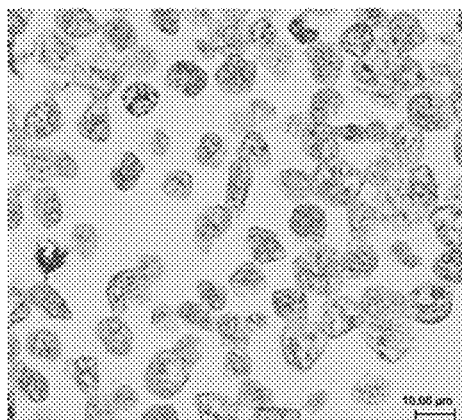
FGFR3 IIIb
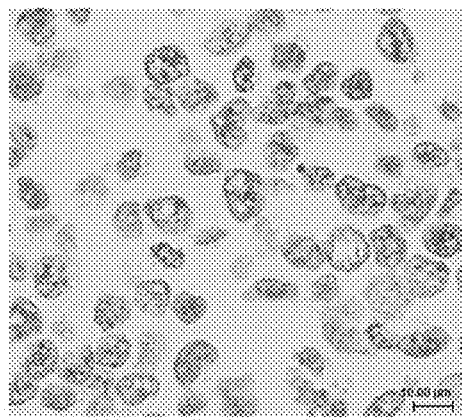
FGFR3 IIIc
[Figure 5D]
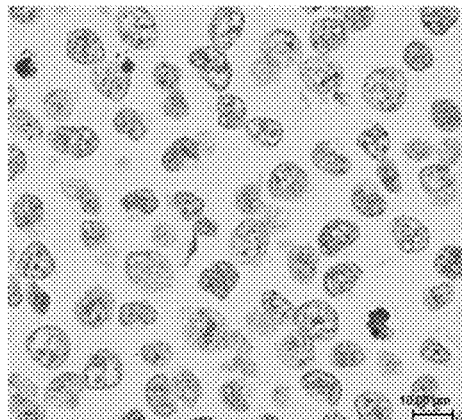
FGFR4
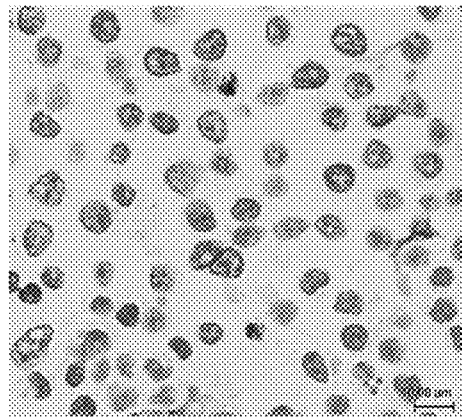
Vector

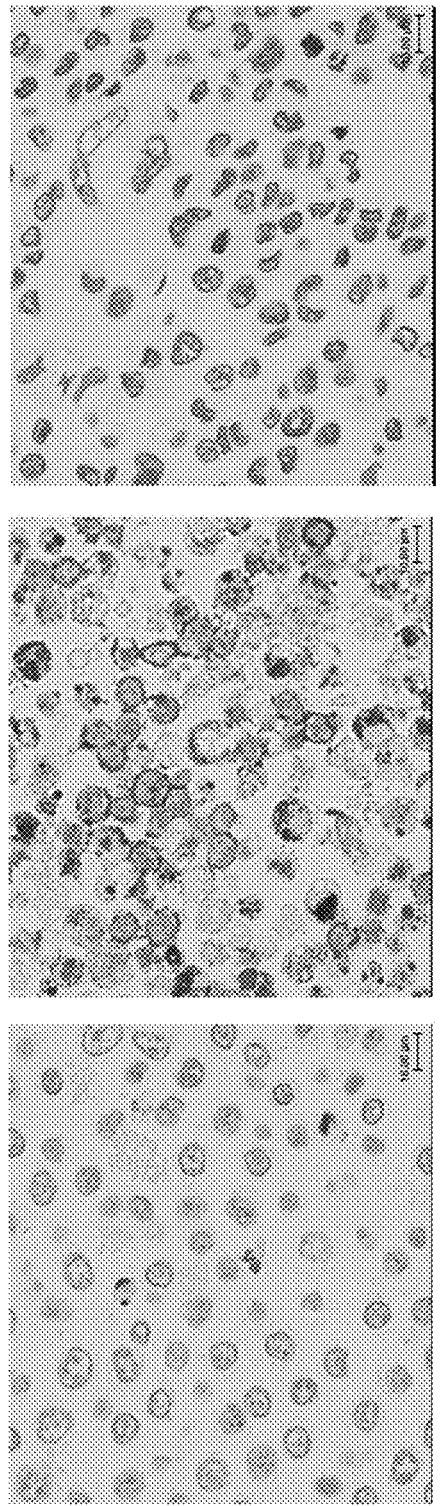
[Figure 6]

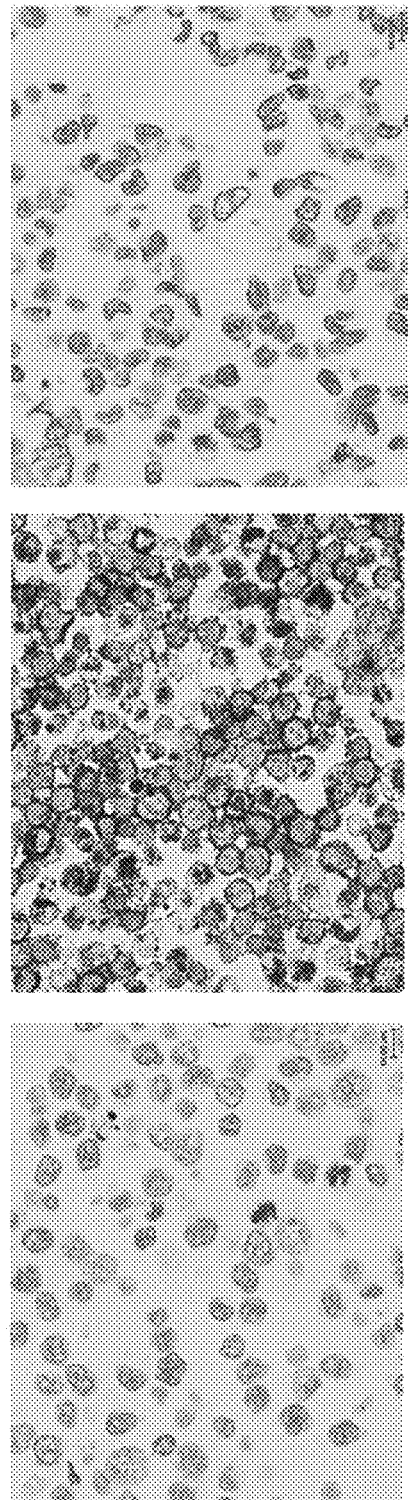
[Figure 7]

[Figure 8]
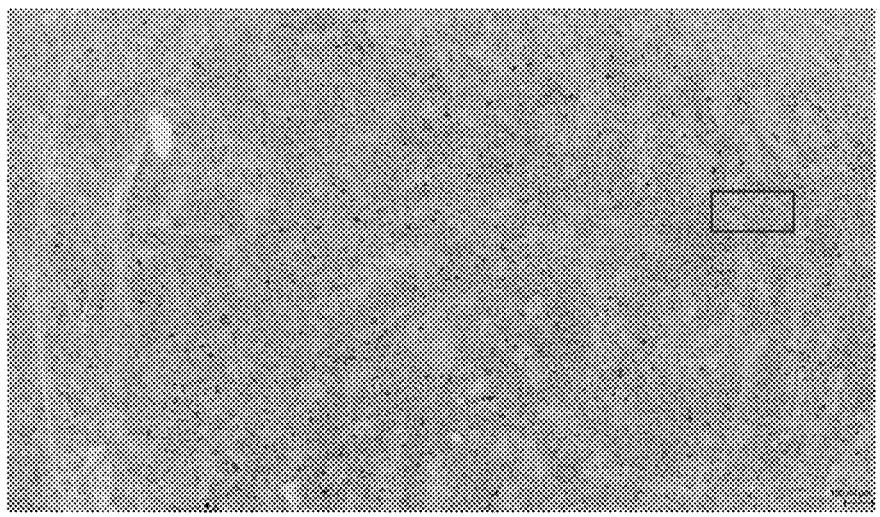
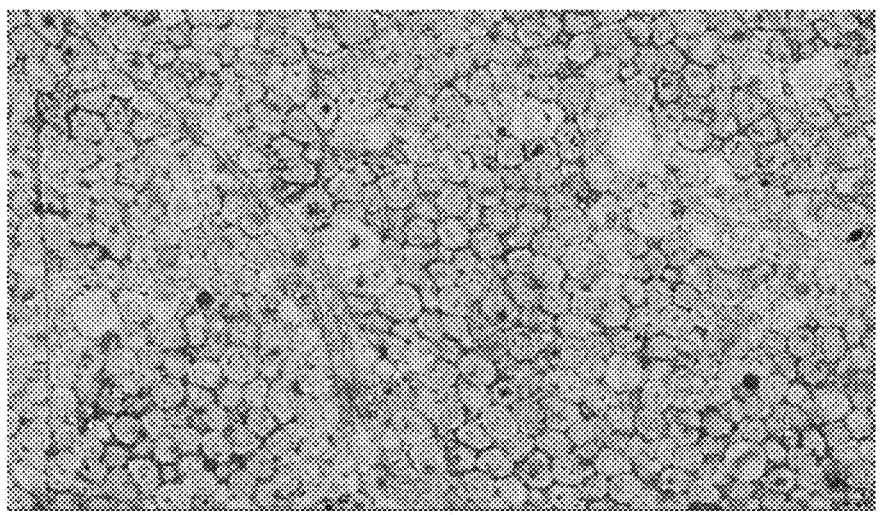
[Figure 9A]
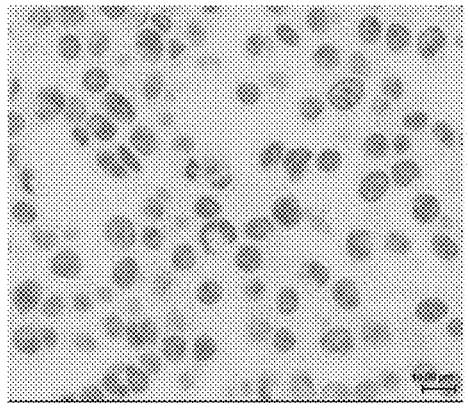
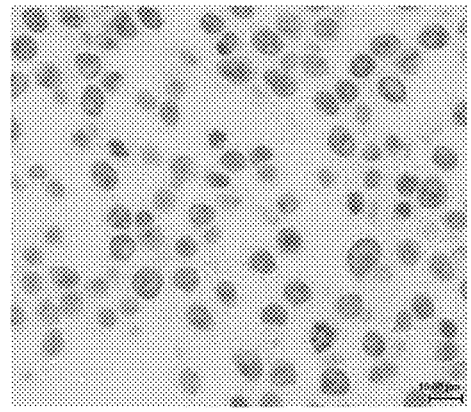
FGFR1 IIIb            FGFR1 IIIc

[Figure 9B]
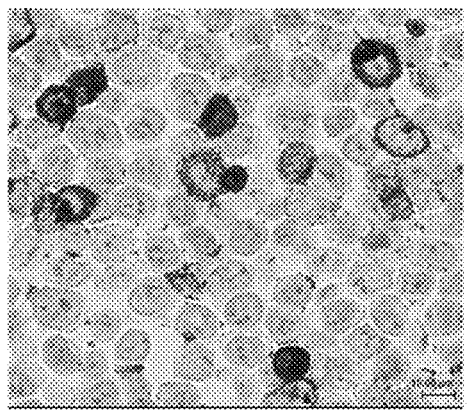 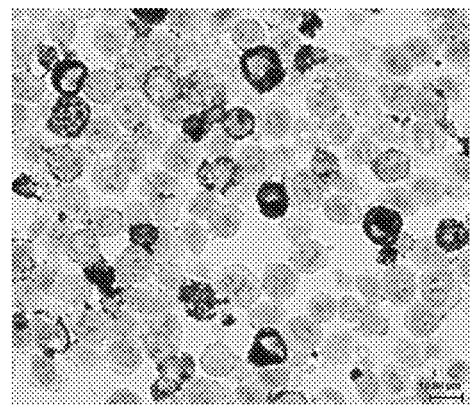
FGFR2 IIIb          FGFR2 IIIc
[Figure 9C]
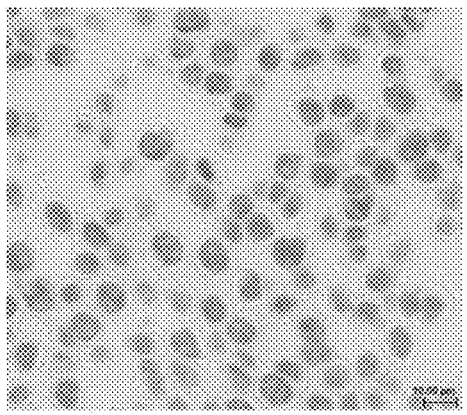 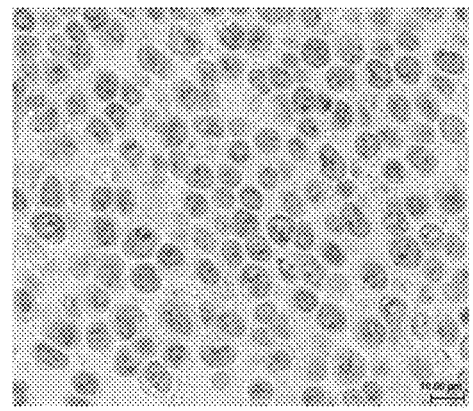
FGFR3 IIIb          FGFR3 IIIc

[Figure 9D]
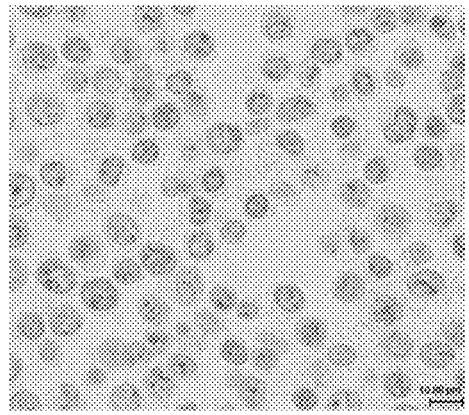
FGFR4
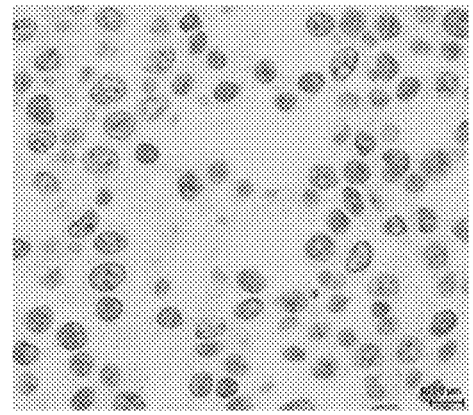
Vector
[Figure 10A]
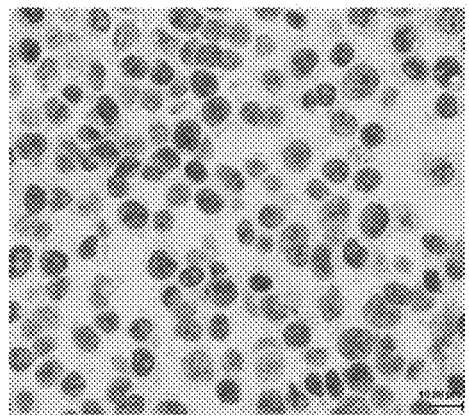
FGFR1 IIIb
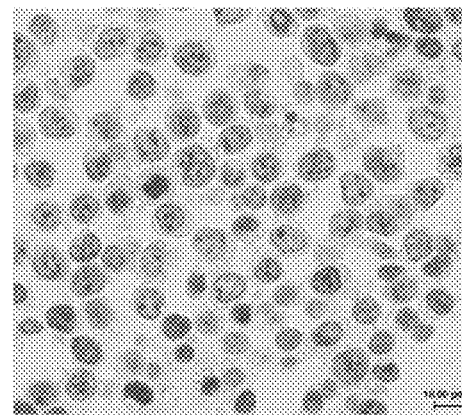
FGFR1 IIIc

[Figure 10B]
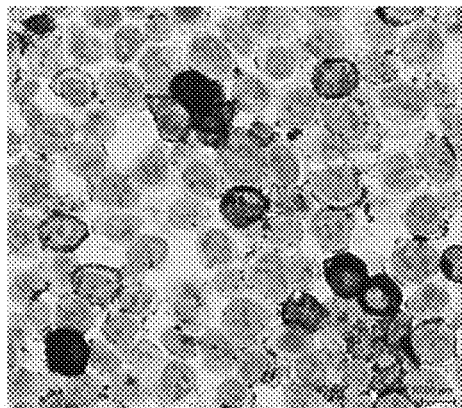
FGFR2 IIIb
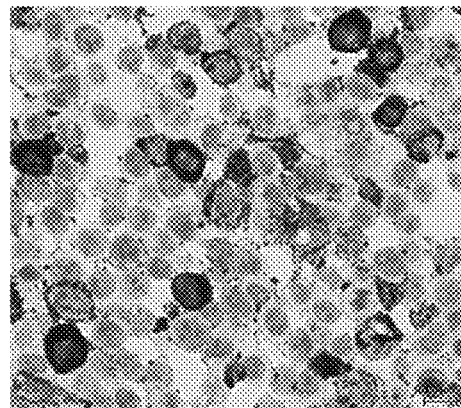
FGFR2 IIIc
[Figure 10C]
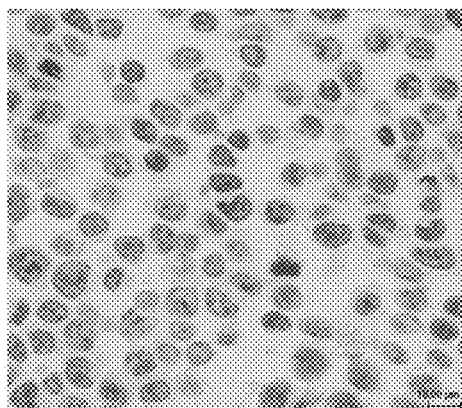
FGFR3 IIIb
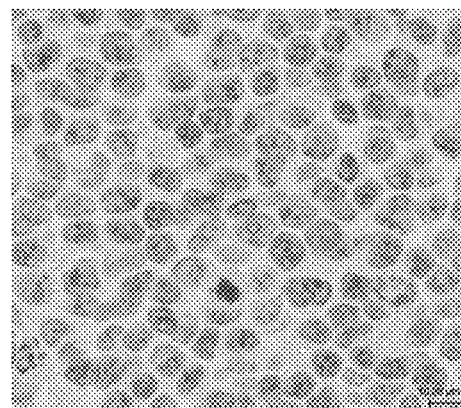
FGFR3 IIIc

[Figure 10D]
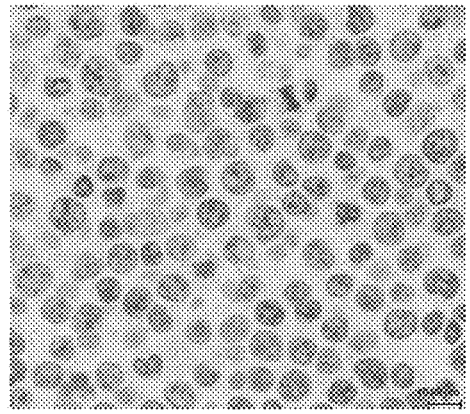 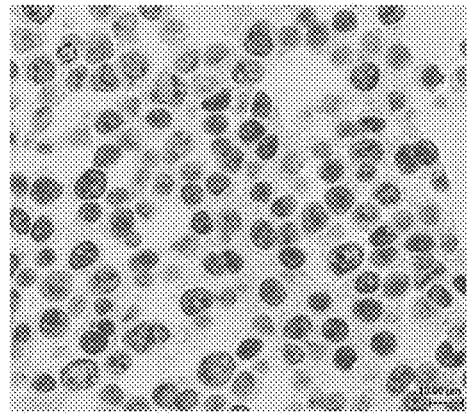
FGFR4　　　　　　　　Vector

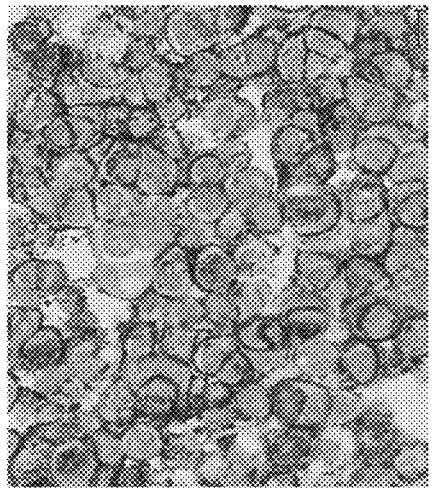
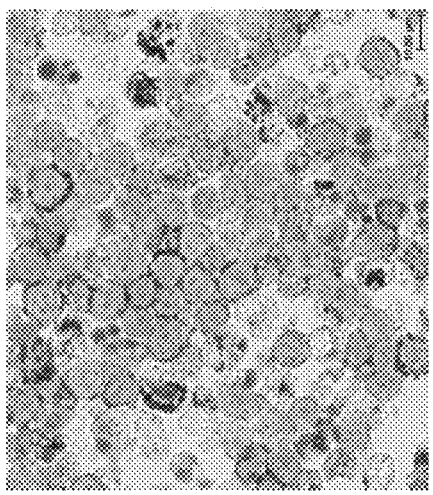
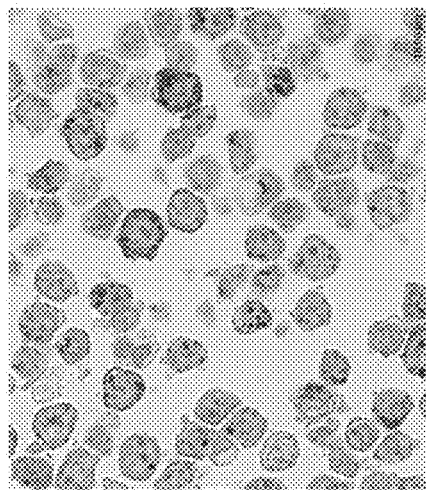
[Figure 11]

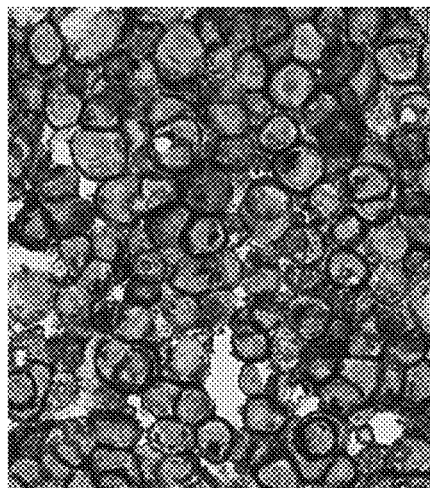
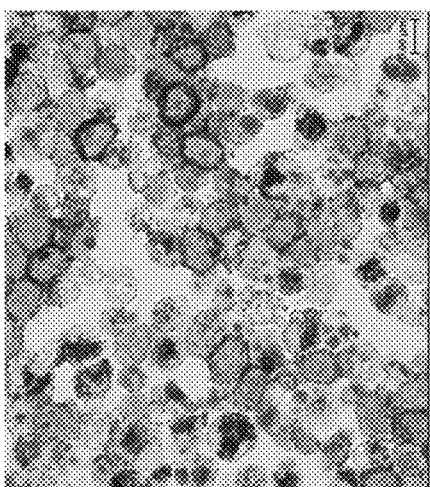
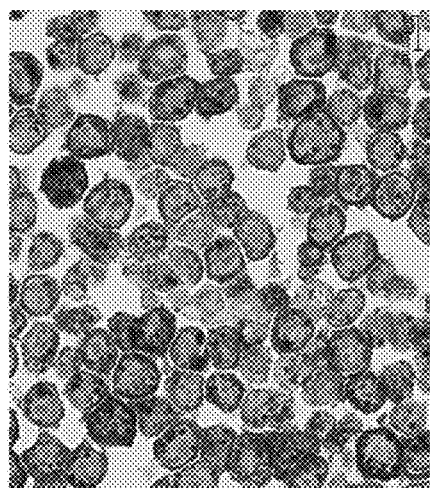
[Figure 12]

[Figure 13A]
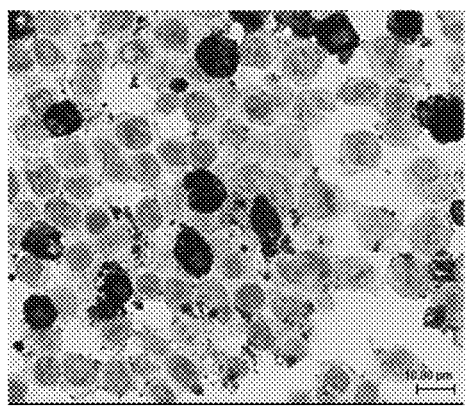
FGFR1 IIIb
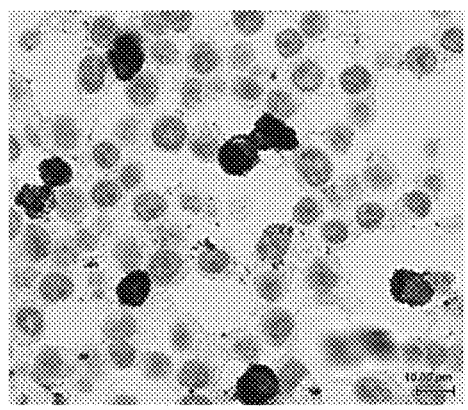
FGFR1 IIIc
[Figure 13B]
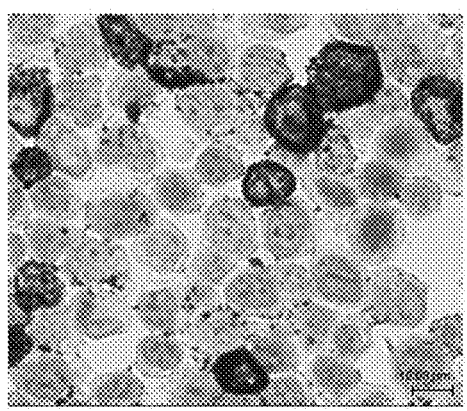
FGFR2 IIIb
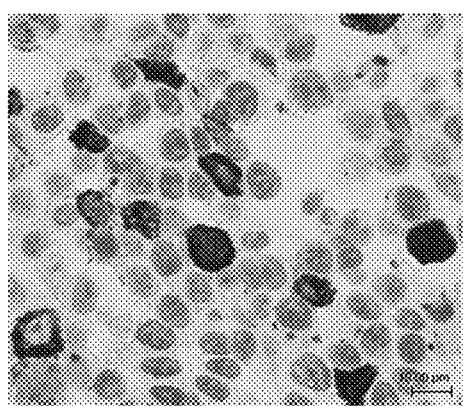
FGFR2 IIIc

[Figure 13C]
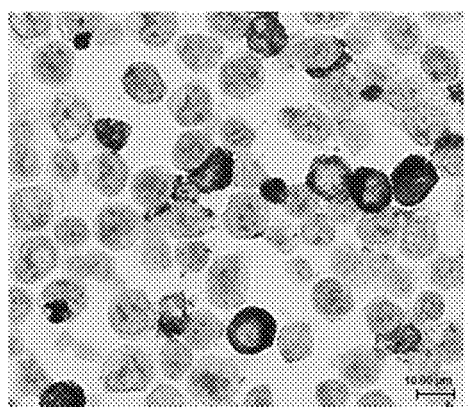
FGFR3 IIIb
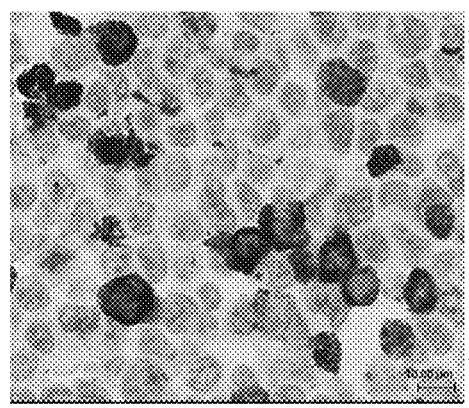
FGFR3 IIIc
[Figure 13D]
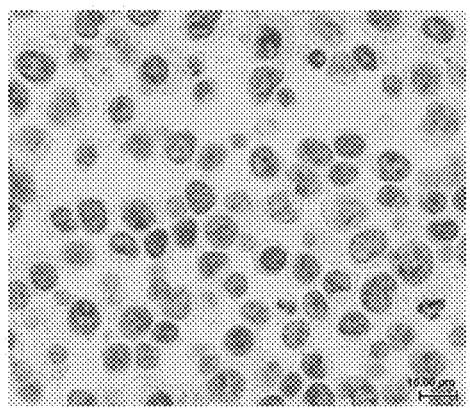
FGFR4
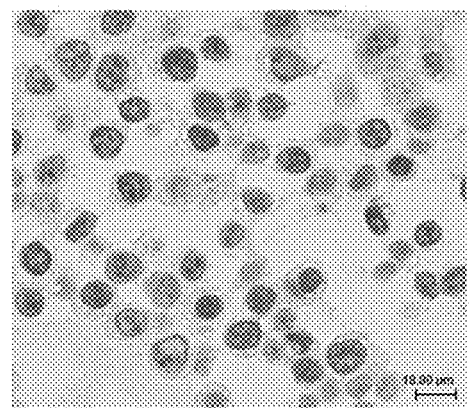
Vector

[Figure 14A]

Figure 14A (SEQ ID NO: 2)

gaggtgcaactggtggagtctggtggaggcttagtgcagcctggaaggtccctgaaa ctctcctgtgcagcctcaggattcactttcagtgactatggcatggcctgggtccgc caggctccaacgaagggctggagtgggtcgcaaccattagttatgatggtagtagc acttactatcgagactccgtgaagggccgtttcactatctccagagaaaatgcaaaa agcaccctatccctgcaaatggacagtctgaggtctgaggacacggccacttattac tgtacaagacatccgacttattactatataatggatgcctggggtcaaggagcttca gtcactgtctcctca Variable region (1-357)

[Figure 14B]

Figure 14B (SEQ ID NO: 3)

EVQLVESGGGLVQPGRSLKLSCAASGFTFSDYGMAWVRQAPTKGLEWVATISYDGSS

TYYRDSVKGRFTISRENAKSTLSLQMDSLRSEDTATYYCTRHPTYYYIMDAWGQGAS

VTVSS

Variable region (1-119)

[Figure 14C]

Figure 14C (SEQ ID NO: 5)

gacactgtactgacccagtctcctgctttggctgtgtctctagggcagagggtcacc atctcttgtagggccagcaaaagtgtcagtacatttatgaactggtaccaacagaaa tcgggacagcaacccaaactcctgatctatagagcatccaacctagaatctggagtc ccttccaggttcagtgggagtgggtctgggacagactttaccctcaccatagatcct gtggaggctgatgacatagcaaactattactgtcagcagagtaatgaacttcctctc acgttcggttctgggaccaagctggagatcaaacgggct Variable region (1-324)

[Figure 14D]

Figure 14D (SEQ ID NO: 6)

DTVLTQSPALAVSLGQRVTISCRASKSVSTFMNWYQQKSGQQPKLLIYRASNLESGV
PSRFSGSGSGTDFTLTIDPVEADDIANYYCQQSNELPLTFGSGTKLEIKRA

Variable region (1-108)

[Figure 15A]

Figure 15A (SEQ ID NO: 7)

gaggtgcagctggtggagtctggggcggcttagtgcagcctggaaggtccatgaaa
ctctcctgtgcagcctcaggactcactttcagtaactatggcatggcctgggtccgc
caggctccaagaagggtctggagtgggtcgcattcattagtcatgatggtggtagc
tcttactatcgagactccgtggagggccgattcattatctccagagataatgcgaaa
agcaccctatccctgcaaatggacagtctgaggtctgaggacacggccacttattac
tgtacaacagccggggactactacagcgacaatgactggtactttgacttctggggc
ccaggaatcatggtcaccgtgtcctca Variable region (1-369)

[Figure 15B]

Figure 15B (SEQ ID NO: 8)

EVQLVESGGGLVQPGRSMKLSCAASGLTFSNYGMAWVRQAPKKGLEWVAFISHDGGS
SYYRDSVEGRFIISRDNAKSTLSLQMDSLRSEDTATYYCTTAGDYYSDNDWYFDFWG
PGIMVTVSS

Variable region (1-123)

[Figure 15C]

Figure 15C (SEQ ID NO: 9)

gacatccagatgacccagtctccttcactcctgtcagcatctgtgggagacagagtc actctcagctgcaaagcaagtcagagtatttacaacagtttagcctggtatcagcaa aaacttggagaagctcccaaactcctcatatatgatgcagacagtttgcaaacgggc atcccatcaaggttcagtggcagtggatctggtacagattacacactcaccatcagc agcctgcagcctgaagatgttgccacatatttctgccagaagtattatagcgggtgg acgttcggtggaggcaccaagctggaattgaaacgggct Variable region (1-324)

[Figure 15D]

Figure 15D (SEQ ID NO: 10)

DIQMTQSPSLLSASVGDRVTLSCKASQSIYNSLAWYQQKLGEAPKLLIYDADSLQTG

IPSRFSGSGSGTDYTLTISSLQPEDVATYFCQKYYSGWTFGGGTKLELKRA

Variable region (1-108)

[Figure 16]

Figure 16 (SEQ ID NO: 11)

gcctccggactctagagccaccATGGTGCTGCAGACCCAGGTGTTCATCTCCCTGCT

GCTGTGGATCTCCGGCGCGTACGGCGATATCGTGATGATTAAACGTACGGTGGCCGC

CCCCTCCGTGTTCATCTTCCCCCCCTCCGACGAGCAGCTGAAGTCCGGCACCGCCTC

CGTGGTGTGCCTGCTGAATAACTTCTACCCCAGAGAGGCCAAGGTGCAGTGGAAGGT

GGACAACGCCCTGCAGTCCGGGAACTCCCAGGAGAGCGTGACCGAGCAGGACAGCAA

GGACAGCACCTACAGCCTGAGCAGCACCCTGACCCTGAGCAAAGCCGACTACGAGAA

GCACAAGGTGTACGCCTGCGAGGTGACCCACCAGGGCCTGAGCTCCCCCGTCACCAA

GAGCTTCAACAGGGGGGAGTGTtagggggcccgtttaaacgggggaggcta

[Figure 17A]

Figure 17A (SEQ ID NO: 14)

ccagcctccggactctagagccaccATGAAACACCTGTGGTTCTTCCTGCTGCTGGT
CGCCGCACCTAGATGGGTCCTGAGTGAAGTCCAGCTGGTCGAAAGCGGGGGGGCCT
GGTGCAGCCAGGACGATCCCTGAAGCTGTCTTGCGCCGCTAGTGGCTTCACCTTTTC
CGACTATGGATGGCATGGGTGCGACAGGCCCCTACCAAAGGACTGGAGTGGGTGGC
CACAATCTCTTACGACGGCAGCTCCACTTACTATAGGGATAGTGTGAAGGGGCGGTT
CACCATTTCAAGAGAGAATGCTAAATCTACACTGAGTCTGCAGATGGACTCACTGCG
AAGCGAAGATACTGCAACCTACTATTGCACCCGGCACCCTACATACTATTACATCAT
GGACGCTTGGGGACAGGGAGCAAGCGTCACCGTGTCTAGTGCCAAGACCACACCCCC
TAGCGTGTATCCACTGGCTCCAGGATCCGCAGCACAGACCAATTCTATGGTGACACT
GGGATGTCTGGTCAAGGGCTACTTCCCTGAGCCAGTCACAGTGACTTGGAACAGCGG
GTCCCTGTCAAGCGGAGTGCACACTTTTCCCGCCGTCCTGCAGAGCGATCTGTACAC
CCTGTCCTCTAGTGTCACTGTGCCCTCAAGCACCTGGCCTAGCGAGACCGTGACATG
CAATGTCGCCCATCCAGCTTCCTCTACAAAGGTGGACAAGAAAATCGTCCCCCGGGA
TTGCGGCTGTAAACCATGCATTTGTACTGTCCCCGAAGTGAGTTCAGTCTTCATCTT
TCCACCCAAGCCCAAGACGTGCTGACTATTACCCTGACACCTAAGGTCACCTGTGT
GGTCGTGGATATCAGCAAAGACGATCCCGAGGTGCAGTTCTCCTGGTTTGTCGACGA
TGTCGAAGTGCACACAGCACAGACTCAGCCTAGGGAGGAACAGTTCAACAGCACATT
TCGCTCTGTGAGTGAGCTGCCAATTATGCATCAGGACTGGCTGAATGGCAAGGAATT
CAAATGCAGAGTGAACTCCGCTGCATTTCCGCTCCTATCGAGAAGACTATTTCTAA
GACCAAAGGGAGGCCTAAAGCACCACAGGTGTATACCATCCCTCCACCCAAGGAACA
GATGGCCAAGGATAAAGTGAGCCTGACATGTATGATCACTGACTTCTTTCCAGAGGA
TATTACAGTGGAATGGCAGTGGAATGGGCAGCCTGCCGAGAACTACAAGAATACACA
GCCAATTATGGACACTGATGGATCATATTTCGTGTACAGCAAGCTGAACGTCCAGAA
ATCTAATTGGGAAGCTGGAAACACTTTTACCTGTAGTGTGCTGCACGAGGGCCTGCA
TAACCACCATACCGAAAAGTCACTGAGCCATTCCCCGGCAAAtgagtttaaacggg
ggaggctaact Signal sequence (26-82), Variable region (83-439),
Constant region (440-1411)

[Figure 17B]

Figure 17B (SEQ ID NO: 15)

MKHLWFFLLLVAAPRWVLSEVQLVESGGGLVQPGRSLKLSCAASGFTFSDYGMAWVR
QAPTKGLEWVATISYDGSSTYYRDSVKGRFTISRENAKSTLSLQMDSLRSEDTATYY
CTRHPTYYYIMDAWGQGASVTVSSAKTTPPSVYPLAPGSAAQTNSMVTLGCLVKGYF
PEPVTVTWNSGSLSSGVHTFPAVLQSDLYTLSSSVTVPSSTWPSETVTCNVAHPASS
TKVDKKIVPRDCGCKPCICTVPEVSSVFIFPPKPKDVLTITLTPKVTCVVVDISKDD
PEVQFSWFVDDVEVHTAQTQPREEQFNSTFRSVSELPIMHQDWLNGKEFKCRVNSAA
FPAPIEKTISKTKGRPKAPQVYTIPPPKEQMAKDKVSLTCMITDFFPEDITVEWQWN
GQPAENYKNTQPIMDTDGSYFVYSKLNVQKSNWEAGNTFTCSVLHEGLHNHHTEKSL
SHSPGK

Signal sequence (1-19), Variable region (20-138),
Constant region (139-462)

[Figure 17C]

Figure 17C (SEQ ID NO: 18)

ccagcctccggactctagagccaccATGGTGCTGCAGACCCAGGTGTTCATTTCACT
GCTGCTGTGGATTTCAGGCGCTTACGGCGATACTGTGCTGACCCAGAGCCCCGCTCT
GGCTGTGAGCCTGGGCCAGCGGGTCACAATCTCCTGCAGAGCATCAAAGAGCGTGTC
CACTTTCATGAACTGGTACCAGCAGAAGTCCGGCCAGCAGCCAAAACTGCTGATCTA
CAGGGCCAGCAATCTGGAGTCCGGGGTGCCCTCTCGCTTCTCTGGAAGTGGCTCAGG
GACCGACTTTACCCTGACAATCGATCCTGTCGAAGCAGACGATATTGCCAACTACTA
TTGCCAGCAGTCTAATGAGCTGCCACTGACCTTCGGAAGTGGCACAAAGCTGGAAAT
CAAACGGGCCGACGCCGCTCCCACAGTGAGCATTTTTCCCCCTAGCTCCGAGCAGCT
GACCAGTGGCGGGGCTTCAGTGGTCTGTTTCCTGAACAATTTTTACCCTAAAGACAT
CAACGTGAAGTGGAAAATTGATGGGAGCGAACGGCAGAACGGAGTCCTGAATTCCTG
GACTGACCAGGATTCTAAGGACAGTACCTATTCAATGTCTAGTACTCTGACCCTGAC
AAAAGATGAGTACGAACGACACAATTCTTATACATGCGAGGCCACTCATAAGACTAG
CACCTCCCCCATCGTGAAAAGCTTTAACAGAAATGAATGTgagtttaaacggggga
ggctaact Signal sequence (26-85), Variable region (86-409),
Constant region (410-724)

[Figure 17D]

Figure 17D (SEQ ID NO: 19)

MVLQTQVFISLLLWISGAYGDTVLTQSPALAVSLGQRVTISCRASKSVSTFMNWYQQ
KSGQQPKLLIYRASNLESGVPSRFSGSGSGTDFTLTIDPVEADDIANYYCQQSNELP
LTFGSGTKLEIKRADAAPTVSIFPPSSEQLTSGGASVVCFLNNFYPKDINVKWKIDG
SERQNGVLNSWTDQDSKDSTYSMSSTLTLTKDEYERHNSYTCEATHKTSTSPIVKSF
NRNEC

Signal sequence (1-20), Variable region (21-128),
Constant region (129-233)

[Figure 18A]

Figure 18A (SEQ ID NO: 20)

ccagcctccggactctagagccaccATGAAACATCTGTGGTTCTTCCTGCTGCTGGT
CGCCGCTCCTCGGTGGGTCCTGAGTGAAGTGCAGCTGGTCGAATCTGGGGGGGCCT
GGTGCAGCCCGGCAGATCCATGAAGCTGTCTTGCGCCGCTAGTGGACTGACCTTCAG
CAATTATGGCATGGCATGGGTGAGGCAGGCCCCTAAGAAAGGACTGGAGTGGGTGGC
TTTCATCAGCCACGACGGCGGGAGCTCCTACTATCGCGATAGTGTGGAAGGCCGGTT
TATCATTTCAAGAGACAATGCAAAGTCTACACTGAGTCTGCAGATGGACTCACTGCG
AAGCGAGGATACAGCTACTTACTATTGCACCACAGCAGGCGACTACTATTCCGACAA
CGATTGGTACTTCGATTTTTGGGGACCAGGCATCATGGTCACCGTGTCTAGTGCCAA
GACTACCCCCCTTCTGTGTATCCACTGGCTCCAGGATCCGCAGCACAGACCAATTC
TATGGTGACACTGGGGTGTCTGGTCAAAGGATACTTCCCTGAGCCAGTCACCGTGAC
ATGGAACAGCGGCTCCCTGTCAAGCGGAGTGCACACCTTTCCAGCAGTCCTGCAGTC
CGATCTGTACACACTGTCCTCTAGTGTCACTGTGCCCTCAAGCACCTGGCCTTCTGA
GACTGTGACCTGCAATGTCGCCCATCCAGCTTCCTCTACTAAGGTGGACAAGAAAAT
CGTCCCCAGGGATTGCGGCTGTAAACCATGCATTTGTACCGTCCCCGAAGTGAGTTC
AGTCTTCATCTTTCCACCCAAGCCCAAAGACGTGCTGACAATTACTCTGACCCCTAA
GGTCACATGTGTGGTCGTGGACATCAGCAAAGACGATCCCGAGGTGCAGTTCTCCTG
GTTTGTCGACGATGTCGAAGTGCACACCGCCCAGACACAGCCTAGGGAGGAACAGTT
CAACAGCACCTTTCGCTCTGTGAGTGAGCTGCCAATTATGCATCAGGACTGGCTGAA
TGGGAAGGAATTCAAATGCCGAGTGAACAGCGCTGCATTTCCCGCCCCTATCGAGAA
GACTATTAGCAAGACCAAAGGACGGCCTAAAGCACCACAGGTGTATACAATCCCTCC
ACCCAAGGAACAGATGGCCAAGGATAAAGTGAGCCTGACATGTATGATCACTGACTT
CTTTCCTGAGGATATTACTGTGGAATGGCAGTGGAATGGCCAGCCTGCCGAGAACTA
CAAGAATACACAGCCAATTATGGACACTGATGGGTCATACTTCGTGTATAGCAAGCT
GAACGTCCAGAAATCTAATTGGGAAGCTGGGAACACCTTCACCTGTAGTGTGCTGCA
CGAGGGACTGCATAACCACCATACCGAAAGTCACTGAGCCATTCCCCCGGCAAAtg
agtttaaacgggggaggctaact Signal sequence (26-82), Variable region (83-451),
Constant region (452-1423)

[Figure 18B]

Figure 18B (SEQ ID NO: 21)

MKHLWFFLLLVAAPRWVLSEVQLVESGGGLVQPGRSMKLSCAASGLTFSNYGMAWVR
QAPKKGLEWVAFISHDGGSSYYRDSVEGRFIISRDNAKSTLSLQMDSLRSEDTATYY
CTTAGDYYSDNDWYFDFWGPGIMVTVSSAKTTPPSVYPLAPGSAAQTNSMVTLGCLV
KGYFPEPVTVTWNSGSLSSGVHTFPAVLQSDLYTLSSSVTVPSSTWPSETVTCNVAH
PASSTKVDKKIVPRDCGCKPCICTVPEVSSVFIFPPKPKDVLTITLTPKVTCVVVDI
SKDDPEVQFSWFVDDVEVHTAQTQPREEQFNSTFRSVSELPIMHQDWLNGKEFKCRV
NSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHHT
EKSLSHSPGK

Signal sequence (1-19), Variable region (20-142),
Constant region (143-466)

[Figure 18C]

Figure 18C (SEQ ID NO: 22)

ccagcctccggactctagagccaccATGGTGCTGCAGACTCAGGTGTTCATTTCACT
GCTGCTGTGGATTAGCGGCGCATACGGCGACATTCAGATGACCCAGAGCCCCTCACT
GCTGTCCGCATCTGTGGGCGACAGGGTCACTCTGAGCTGCAAGGCTAGTCAGTCAAT
CTACAACTCCCTGGCATGGTATCAGCAGAAGCTGGGGGAGGCACCAAAACTGCTGAT
CTACGACGCCGATAGCCTGCAGACCGGAATTCCATCCCGCTTCAGCGGATCCGGATC
TGGAACAGACTACACCCTGACAATCAGCTCCCTGCAGCCCGAAGATGTGGCTACCTA
TTTCTGCCAGAAGTACTATTCCGGGTGGACCTTTGGCGGGGAACAAAGCTGGAGCT
GAAACGAGCCGATGCCGCTCCTACAGTCAGCATTTTTCCCCCTTCTAGTGAACAGCT
GACTAGTGGCGGGGCTTCAGTGGTCTGTTTCCTGAACAATTTTTACCCAAAAGACAT
CAACGTGAAGTGGAAAATTGATGGATCTGAGAGACAGAACGGCGTCCTGAATAGTTG
GACTGACCAGGATAGCAAGGACTCCACCTATTCTATGTCAAGCACTCTGACCCTGAC
AAAAGATGAGTACGAACGGCACAATTCTTATACATGCGAGGCCACTCATAAGACTAG
TACCTCACCTATTGTGAAAAGCTTCAACAGAAATGAATGTtgagtttaaacggggga
ggctaact Signal sequence (26-85), Variable region (86-409),
Constant region (410-724)

[Figure 18D]

Figure 18D (SEQ ID NO: 23)

MVLQTQVFISLLLWISGAYGDIQMTQSPSLLSASVGDRVTLSCKASQSIYNSLAWYQ
QKLGEAPKLLIYDADSLQTGIPSRFSGSGSGTDYTLTISSLQPEDVATYFCQKYYSG
WTFGGGTKLELKRADAAPTVSIFPPSSEQLTSGGASVVCFLNNFYPKDINVKWKIDG
SERQNGVLNSWTDQDSKDSTYSMSSTLTLTKDEYERHNSYTCEATHKTSTSPIVKSF
NRNEC

Signal sequence (1-20), Variable region (21-128),
Constant region (129-233)

Rat anti-human FGFR2 antibody FR2-2nd_#028

CDRH1 : GFTFSDYGMA         (SEQ ID NO: 24)

CDRH2 : TISYDGSSTYYRDSVKG  (SEQ ID NO: 25)

CDRH3 : HPTYYYIMDA         (SEQ ID NO: 26)

CDRL1 : RASKSVSTFMN        (SEQ ID NO: 27)

CDRL2 : RASNLES            (SEQ ID NO: 28)

CDRL3 : QQSNELPLT          (SEQ ID NO: 29)

Rat anti-human FGFR2 antibody FR2-2nd_#023

CDRH1 : GLTFSNYGMA         (SEQ ID NO: 30)

CDRH2 : FISHDGGSSYYRDSVEG  (SEQ ID NO: 31)

CDRH3 : AGDYYSDNDWYFDF     (SEQ ID NO: 32)

CDRL1 : KASQSIYNSLA        (SEQ ID NO: 33)

CDRL2 : DADSLQT            (SEQ ID NO: 34)

CDRL3 : QKYYSGWT           (SEQ ID NO: 35)

SEQUENCE LISTING

<160> NUMBER OF SEQ ID NOS: 35

<210> SEQ ID NO 1
<211> LENGTH: 29
<212> TYPE: DNA
<213> ORGANISM: Artificial Sequence

```
<220> FEATURE:
<223> OTHER INFORMATION: primer

<400> SEQUENCE: 1
ctccagagtt ccaggtcacg gtgactggc                                    29

<210> SEQ ID NO 2
<211> LENGTH: 357
<212> TYPE: DNA
<213> ORGANISM: Rattus norvegicus
<220> FEATURE:
<221> NAME/KEY: CDS
<222> LOCATION: (1)..(357)

<400> SEQUENCE: 2 gag gtg caa ctg gtg gag tct ggt gga ggc tta gtg cag cct gga agg     48
Glu Val Gln Leu Val Glu Ser Gly Gly Gly Leu Val Gln Pro Gly Arg
1               5                   10                  15 tcc ctg aaa ctc tcc tgt gca gcc tca gga ttc act ttc agt gac tat     96
Ser Leu Lys Leu Ser Cys Ala Ala Ser Gly Phe Thr Phe Ser Asp Tyr
            20                  25                  30 ggc atg gcc tgg gtc cgc cag gct cca acg aag ggg ctg gag tgg gtc    144
Gly Met Ala Trp Val Arg Gln Ala Pro Thr Lys Gly Leu Glu Trp Val
        35                  40                  45 gca acc att agt tat gat ggt agt agc act tac tat cga gac tcc gtg    192
Ala Thr Ile Ser Tyr Asp Gly Ser Ser Thr Tyr Tyr Arg Asp Ser Val
    50                  55                  60 aag ggc cgt ttc act atc tcc aga gaa aat gca aaa agc acc cta tcc    240
Lys Gly Arg Phe Thr Ile Ser Arg Glu Asn Ala Lys Ser Thr Leu Ser
65                  70                  75                  80 ctg caa atg gac agt ctg agg tct gag gac acg gcc act tat tac tgt    288
Leu Gln Met Asp Ser Leu Arg Ser Glu Asp Thr Ala Thr Tyr Tyr Cys
                85                  90                  95 aca aga cat ccg act tat tac tat ata atg gat gcc tgg ggt caa gga    336
Thr Arg His Pro Thr Tyr Tyr Tyr Ile Met Asp Ala Trp Gly Gln Gly
            100                 105                 110 gct tca gtc act gtc tcc tca                                        357
Ala Ser Val Thr Val Ser Ser
        115

<210> SEQ ID NO 3
<211> LENGTH: 119
<212> TYPE: PRT
<213> ORGANISM: Rattus norvegicus

<400> SEQUENCE: 3

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Gly Met Ala Trp Val Arg Gln Ala Pro Thr Lys Gly Leu Glu Trp Val
        35                  40                  45

Ala Thr Ile Ser Tyr Asp Gly Ser Ser Thr Tyr Tyr Arg Asp Ser Val
    50                  55                  60

Lys Gly Arg Phe Thr Ile Ser Arg Glu Asn Ala Lys Ser Thr Leu Ser
65                  70                  75                  80

Leu Gln Met Asp Ser Leu Arg Ser Glu Asp Thr Ala Thr Tyr Tyr Cys
                85                  90                  95

Thr Arg His Pro Thr Tyr Tyr Tyr Ile Met Asp Ala Trp Gly Gln Gly
            100                 105                 110
```

Ala Ser Val Thr Val Ser Ser
            115

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
tcagtaacac tgtccaggac accatctc                                          28

<210> SEQ ID NO 5
<211> LENGTH: 324
<212> TYPE: DNA
<213> ORGANISM: Rattus exulans
<220> FEATURE:
<221> NAME/KEY: CDS
<222> LOCATION: (1)..(324)

<400> SEQUENCE: 5 gac act gta ctg acc cag tct cct gct ttg gct gtg tct cta ggg cag        48
Asp Thr Val Leu Thr Gln Ser Pro Ala Leu Ala Val Ser Leu Gly Gln
1               5                   10                  15 agg gtc acc atc tct tgt agg gcc agc aaa agt gtc agt aca ttt atg        96
Arg Val Thr Ile Ser Cys Arg Ala Ser Lys Ser Val Ser Thr Phe Met
            20                  25                  30 aac tgg tac caa cag aaa tcg gga cag caa ccc aaa ctc ctg atc tat       144
Asn Trp Tyr Gln Gln Lys Ser Gly Gln Gln Pro Lys Leu Leu Ile Tyr
        35                  40                  45 aga gca tcc aac cta gaa tct gga gtc cct tcc agg ttc agt ggg agt       192
Arg Ala Ser Asn Leu Glu Ser Gly Val Pro Ser Arg Phe Ser Gly Ser
    50                  55                  60 ggg tct ggg aca gac ttt acc ctc acc ata gat cct gtg gag gct gat       240
Gly Ser Gly Thr Asp Phe Thr Leu Thr Ile Asp Pro Val Glu Ala Asp
65                  70                  75                  80 gac ata gca aac tat tac tgt cag cag agt aat gaa ctt cct ctc acg       288
Asp Ile Ala Asn Tyr Tyr Cys Gln Gln Ser Asn Glu Leu Pro Leu Thr
                85                  90                  95 ttc ggt tct ggg acc aag ctg gag atc aaa cgg gct                       324
Phe Gly Ser Gly Thr Lys Leu Glu Ile Lys Arg Ala
            100                 105

<210> SEQ ID NO 6
<211> LENGTH: 108
<212> TYPE: PRT
<213> ORGANISM: Rattus exulans

<400> SEQUENCE: 6

Asp Thr Val Leu Thr Gln Ser Pro Ala Leu Ala Val Ser Leu Gly Gln
1               5                   10                  15

Arg Val Thr Ile Ser Cys Arg Ala Ser Lys Ser Val Ser Thr Phe Met
            20                  25                  30

Asn Trp Tyr Gln Gln Lys Ser Gly Gln Gln Pro Lys Leu Leu Ile Tyr
        35                  40                  45

Arg Ala Ser Asn Leu Glu Ser Gly Val Pro Ser Arg Phe Ser Gly Ser
    50                  55                  60

Gly Ser Gly Thr Asp Phe Thr Leu Thr Ile Asp Pro Val Glu Ala Asp
65                  70                  75                  80

Asp Ile Ala Asn Tyr Tyr Cys Gln Gln Ser Asn Glu Leu Pro Leu Thr
                85                  90                  95

Phe Gly Ser Gly Thr Lys Leu Glu Ile Lys Arg Ala
            100                 105

<210> SEQ ID NO 7
<211> LENGTH: 369
<212> TYPE: DNA
<213> ORGANISM: Rattus norvegicus
<220> FEATURE:
<221> NAME/KEY: CDS
<222> LOCATION: (1)..(369)

<400> SEQUENCE: 7

```
gag gtg cag ctg gtg gag tct ggg ggc ggc tta gtg cag cct gga agg      48
Glu Val Gln Leu Val Glu Ser Gly Gly Gly Leu Val Gln Pro Gly Arg
1               5                   10                  15 tcc atg aaa ctc tcc tgt gca gcc tca gga ctc act ttc agt aac tat      96
Ser Met Lys Leu Ser Cys Ala Ala Ser Gly Leu Thr Phe Ser Asn Tyr
            20                  25                  30 ggc atg gcc tgg gtc cgc cag gct cca aag aag ggt ctg gag tgg gtc     144
Gly Met Ala Trp Val Arg Gln Ala Pro Lys Lys Gly Leu Glu Trp Val
        35                  40                  45 gca ttc att agt cat gat ggt ggt agc tct tac tat cga gac tcc gtg     192
Ala Phe Ile Ser His Asp Gly Gly Ser Ser Tyr Tyr Arg Asp Ser Val
    50                  55                  60 gag ggc cga ttc att atc tcc aga gat aat gcg aaa agc acc cta tcc     240
Glu Gly Arg Phe Ile Ile Ser Arg Asp Asn Ala Lys Ser Thr Leu Ser
65                  70                  75                  80 ctg caa atg gac agt ctg agg tct gag gac acg gcc act tat tac tgt     288
Leu Gln Met Asp Ser Leu Arg Ser Glu Asp Thr Ala Thr Tyr Tyr Cys
                85                  90                  95 aca aca gcc ggg gac tac tac agc gac aat gac tgg tac ttt gac ttc     336
Thr Thr Ala Gly Asp Tyr Tyr Ser Asp Asn Asp Trp Tyr Phe Asp Phe
            100                 105                 110 tgg ggc cca gga atc atg gtc acc gtg tcc tca                         369
Trp Gly Pro Gly Ile Met Val Thr Val Ser Ser
        115                 120
```

<210> SEQ ID NO 8
<211> LENGTH: 123
<212> TYPE: PRT
<213> ORGANISM: Rattus norvegicus

<400> SEQUENCE: 8

Glu Val Gln Leu Val Glu Ser Gly Gly Gly Leu Val Gln Pro Gly Arg
1               5                   10                  15

Ser Met Lys Leu Ser Cys Ala Ala Ser Gly Leu Thr Phe Ser Asn Tyr
            20                  25                  30

Gly Met Ala Trp Val Arg Gln Ala Pro Lys Lys Gly Leu Glu Trp Val
        35                  40                  45

Ala Phe Ile Ser His Asp Gly Gly Ser Ser Tyr Tyr Arg Asp Ser Val
    50                  55                  60

Glu Gly Arg Phe Ile Ile Ser Arg Asp Asn Ala Lys Ser Thr Leu Ser
65                  70                  75                  80

Leu Gln Met Asp Ser Leu Arg Ser Glu Asp Thr Ala Thr Tyr Tyr Cys
                85                  90                  95

Thr Thr Ala Gly Asp Tyr Tyr Ser Asp Asn Asp Trp Tyr Phe Asp Phe
            100                 105                 110

Trp Gly Pro Gly Ile Met Val Thr Val Ser Ser
        115                 120

<210> SEQ ID NO 9
<211> LENGTH: 324
<212> TYPE: DNA
<213> ORGANISM: Rattus norvegicus
<220> FEATURE:
<221> NAME/KEY: CDS
<222> LOCATION: (1)..(324)

<400> SEQUENCE: 9

| gac | atc | cag | atg | acc | cag | tct | cct | tca | ctc | ctg | tca | gca | tct | gtg | gga | 48 |
| Asp | Ile | Gln | Met | Thr | Gln | Ser | Pro | Ser | Leu | Leu | Ser | Ala | Ser | Val | Gly | |
| 1 | | | | 5 | | | | | 10 | | | | | 15 | | |

| gac | aga | gtc | act | ctc | agc | tgc | aaa | gca | agt | cag | agt | att | tac | aac | agt | 96 |
| Asp | Arg | Val | Thr | Leu | Ser | Cys | Lys | Ala | Ser | Gln | Ser | Ile | Tyr | Asn | Ser | |
| | | | 20 | | | | | 25 | | | | | 30 | | | |

| tta | gcc | tgg | tat | cag | caa | aaa | ctt | gga | gaa | gct | ccc | aaa | ctc | ctc | ata | 144 |
| Leu | Ala | Trp | Tyr | Gln | Gln | Lys | Leu | Gly | Glu | Ala | Pro | Lys | Leu | Leu | Ile | |
| | | | 35 | | | | | 40 | | | | | 45 | | | |

| tat | gat | gca | gac | agt | ttg | caa | acg | ggc | atc | cca | tca | agg | ttc | agt | ggc | 192 |
| Tyr | Asp | Ala | Asp | Ser | Leu | Gln | Thr | Gly | Ile | Pro | Ser | Arg | Phe | Ser | Gly | |
| | 50 | | | | | 55 | | | | | 60 | | | | | |

| agt | gga | tct | ggt | aca | gat | tac | aca | ctc | acc | atc | agc | agc | ctg | cag | cct | 240 |
| Ser | Gly | Ser | Gly | Thr | Asp | Tyr | Thr | Leu | Thr | Ile | Ser | Ser | Leu | Gln | Pro | |
| 65 | | | | | 70 | | | | | 75 | | | | | 80 | |

| gaa | gat | gtt | gcc | aca | tat | ttc | tgc | cag | aag | tat | tat | agc | ggg | tgg | acg | 288 |
| Glu | Asp | Val | Ala | Thr | Tyr | Phe | Cys | Gln | Lys | Tyr | Tyr | Ser | Gly | Trp | Thr | |
| | | | | 85 | | | | | 90 | | | | | 95 | | |

| ttc | ggt | gga | ggc | acc | aag | ctg | gaa | ttg | aaa | cgg | gct | | | | | 324 |
| Phe | Gly | Gly | Gly | Thr | Lys | Leu | Glu | Leu | Lys | Arg | Ala | | | | | |
| | | | 100 | | | | | 105 | | | | | | | | |

<210> SEQ ID NO 10
<211> LENGTH: 108
<212> TYPE: PRT
<213> ORGANISM: Rattus norvegicus

<400> SEQUENCE: 10

Asp Ile Gln Met Thr Gln Ser Pro Ser Leu Leu Ser Ala Ser Val Gly
1               5                   10                  15

Asp Arg Val Thr Leu Ser Cys Lys Ala Ser Gln Ser Ile Tyr Asn Ser
            20                  25                  30

Leu Ala Trp Tyr Gln Gln Lys Leu Gly Glu Ala Pro Lys Leu Leu Ile
        35                  40                  45

Tyr Asp Ala Asp Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Lys Tyr Tyr Ser Gly Trp Thr
                85                  90                  95

Phe Gly Gly Gly Thr Lys Leu Glu Leu Lys Arg Ala
            100                 105

<210> SEQ ID NO 11
<211> LENGTH: 449
<212> TYPE: DNA
<213> ORGANISM: Homo sapiens

<400> SEQUENCE: 11
gcctccggac tctagagcca ccatggtgct gcagacccag gtgttcatct ccctgctgct    60
gtggatctcc ggcgcgtacg gcgatatcgt gatgattaaa cgtacggtgg ccgccccctc   120

```
cgtgttcatc ttccccccct ccgacgagca gctgaagtcc ggcaccgcct ccgtggtgtg    180
cctgctgaat aacttctacc ccagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgaa agcacaaagg tgtacgcctg    360
cgaggtgacc caccagggcc tgagctcccc cgtcaccaag agcttcaaca ggggggagtg    420 ttagggccc gtttaaacgg gggaggcta                                        449

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
tataccgtcg acctctagct agagcttggc                                       30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
gctatggcag ggcctgccgc cccgacgttg                                       30

<210> SEQ ID NO 14
<211> LENGTH: 1436
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (26)..(1411)

<400> SEQUENCE: 14
ccagcctccg gactctagag ccacc atg aaa cac ctg tgg ttc ttc ctg ctg       52
                            Met Lys His Leu Trp Phe Phe Leu Leu
                              1               5 ctg gtc gcc gca cct aga tgg gtc ctg agt gaa gtc cag ctg gtc gaa      100
Leu Val Ala Ala Pro Arg Trp Val Leu Ser Glu Val Gln Leu Val Glu
 10              15                  20                  25 agc ggg ggg ggc ctg gtg cag cca gga cga tcc ctg aag ctg tct tgc      148
Ser Gly Gly Gly Leu Val Gln Pro Gly Arg Ser Leu Lys Leu Ser Cys
                 30                  35                  40 gcc gct agt ggc ttc acc ttt tcc gac tat ggg atg gca tgg gtg cga      196
Ala Ala Ser Gly Phe Thr Phe Ser Asp Tyr Gly Met Ala Trp Val Arg
             45                  50                  55 cag gcc cct acc aaa gga ctg gag tgg gtg gcc aca atc tct tac gac      244
Gln Ala Pro Thr Lys Gly Leu Glu Trp Val Ala Thr Ile Ser Tyr Asp
         60                  65                  70 ggc agc tcc act tac tat agg gat agt gtg aag ggg cgg ttc acc att      292
Gly Ser Ser Thr Tyr Tyr Arg Asp Ser Val Lys Gly Arg Phe Thr Ile
     75                  80                  85 tca aga gag aat gct aaa tct aca ctg agt ctg cag atg gac tca ctg      340
Ser Arg Glu Asn Ala Lys Ser Thr Leu Ser Leu Gln Met Asp Ser Leu
 90                  95                 100                 105 cga agc gaa gat act gca acc tac tat tgc acc cgg cac cct aca tac      388
```

```
                Arg Ser Glu Asp Thr Ala Thr Tyr Tyr Cys Thr Arg His Pro Thr Tyr
                                110                 115                 120 tat tac atc atg gac gct tgg gga cag gga gca agc gtc acc gtg tct            436
Tyr Tyr Ile Met Asp Ala Trp Gly Gln Gly Ala Ser Val Thr Val Ser
            125                 130                 135 agt gcc aag acc aca ccc cct agc gtg tat cca ctg gct cca gga tcc            484
Ser Ala Lys Thr Thr Pro Pro Ser Val Tyr Pro Leu Ala Pro Gly Ser
        140                 145                 150 gca gca cag acc aat tct atg gtg aca ctg gga tgt ctg gtc aag ggc            532
Ala Ala Gln Thr Asn Ser Met Val Thr Leu Gly Cys Leu Val Lys Gly
    155                 160                 165 tac ttc cct gag cca gtc aca gtg act tgg aac agc ggg tcc ctg tca            580
Tyr Phe Pro Glu Pro Val Thr Val Thr Trp Asn Ser Gly Ser Leu Ser
170                 175                 180                 185 agc gga gtg cac act ttt ccc gcc gtc ctg cag agc gat ctg tac acc            628
Ser Gly Val His Thr Phe Pro Ala Val Leu Gln Ser Asp Leu Tyr Thr
                190                 195                 200 ctg tcc tct agt gtc act gtg ccc tca agc acc tgg cct agc gag acc            676
Leu Ser Ser Ser Val Thr Val Pro Ser Ser Thr Trp Pro Ser Glu Thr
            205                 210                 215 gtg aca tgc aat gtc gcc cat cca gct tcc tct aca aag gtg gac aag            724
Val Thr Cys Asn Val Ala His Pro Ala Ser Ser Thr Lys Val Asp Lys
        220                 225                 230 aaa atc gtc ccc cgg gat tgc ggc tgt aaa cca tgc att tgt act gtc            772
Lys Ile Val Pro Arg Asp Cys Gly Cys Lys Pro Cys Ile Cys Thr Val
    235                 240                 245 ccc gaa gtg agt tca gtc ttc atc ttt cca ccc aag ccc aaa gac gtg            820
Pro Glu Val Ser Ser Val Phe Ile Phe Pro Pro Lys Pro Lys Asp Val
250                 255                 260                 265 ctg act att acc ctg aca cct aag gtc acc tgt gtg gtc gtg gat atc            868
Leu Thr Ile Thr Leu Thr Pro Lys Val Thr Cys Val Val Val Asp Ile
                270                 275                 280 agc aaa gac gat ccc gag gtg cag ttc tcc tgg ttt gtc gac gat gtc            916
Ser Lys Asp Asp Pro Glu Val Gln Phe Ser Trp Phe Val Asp Asp Val
            285                 290                 295 gaa gtg cac aca gca cag act cag cct agg gag gaa cag ttc aac agc            964
Glu Val His Thr Ala Gln Thr Gln Pro Arg Glu Glu Gln Phe Asn Ser
        300                 305                 310 aca ttt cgc tct gtg agt gag ctg cca att atg cat cag gac tgg ctg           1012
Thr Phe Arg Ser Val Ser Glu Leu Pro Ile Met His Gln Asp Trp Leu
    315                 320                 325 aat ggc aag gaa ttc aaa tgc aga gtg aac tcc gct gca ttt ccc gct           1060
Asn Gly Lys Glu Phe Lys Cys Arg Val Asn Ser Ala Ala Phe Pro Ala
330                 335                 340                 345 cct atc gag aag act att tct aag acc aaa ggg agg cct aaa gca cca           1108
Pro Ile Glu Lys Thr Ile Ser Lys Thr Lys Gly Arg Pro Lys Ala Pro
                350                 355                 360 cag gtg tat acc atc cct cca ccc aag gaa cag atg gcc aag gat aaa           1156
Gln Val Tyr Thr Ile Pro Pro Pro Lys Glu Gln Met Ala Lys Asp Lys
            365                 370                 375 gtg agc ctg aca tgt atg atc act gac ttc ttt cca gag gat att aca           1204
Val Ser Leu Thr Cys Met Ile Thr Asp Phe Phe Pro Glu Asp Ile Thr
        380                 385                 390 gtg gaa tgg cag tgg aat ggg cag cct gcc gag aac tac aag aat aca           1252
Val Glu Trp Gln Trp Asn Gly Gln Pro Ala Glu Asn Tyr Lys Asn Thr
    395                 400                 405 cag cca att atg gac act gat gga tca tat ttc gtg tac agc aag ctg           1300
Gln Pro Ile Met Asp Thr Asp Gly Ser Tyr Phe Val Tyr Ser Lys Leu
410                 415                 420                 425
```

-continued

```
aac gtc cag aaa tct aat tgg gaa gct gga aac act ttt acc tgt agt    1348
Asn Val Gln Lys Ser Asn Trp Glu Ala Gly Asn Thr Phe Thr Cys Ser
            430                 435                 440 gtg ctg cac gag ggc ctg cat aac cac cat acc gaa aag tca ctg agc    1396
Val Leu His Glu Gly Leu His Asn His His Thr Glu Lys Ser Leu Ser
            445                 450                 455 cat tcc ccc ggc aaa tgagtttaaa cggggaggc taact                     1436
His Ser Pro Gly Lys
            460
```

<210> SEQ ID NO 15
<211> LENGTH: 462
<212> TYPE: PRT
<213> ORGANISM: Artificial Sequence
<220> FEATURE:
<223> OTHER INFORMATION: Synthetic Construct

<400> SEQUENCE: 15

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asp Tyr Gly Met Ala Trp Val Arg Gln Ala Pro Thr Lys Gly Leu
    50                  55                  60

Glu Trp Val Ala Thr Ile Ser Tyr Asp Gly Ser Ser Thr Tyr Tyr Arg
65                  70                  75                  80

Asp Ser Val Lys Gly Arg Phe Thr Ile Ser Arg Glu Asn Ala Lys Ser
                85                  90                  95

Thr Leu Ser Leu Gln Met Asp Ser Leu Arg Ser Glu Asp Thr Ala Thr
            100                 105                 110

Tyr Tyr Cys Thr Arg His Pro Thr Tyr Tyr Ile Met Asp Ala Trp
        115                 120                 125

Gly Gln Gly Ala Ser Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300
```

```
Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
            325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
    450                 455                 460

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
ccagcctccg gactctagag ccacc                                         25

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
agttagcctc ccccgtttaa actc                                          24

<210> SEQ ID NO 18
<211> LENGTH: 749
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (26)..(724)

<400> SEQUENCE: 18
ccagcctccg gactctagag ccacc atg gtg ctg cag acc cag gtg ttc att    52
                            Met Val Leu Gln Thr Gln Val Phe Ile
                            1               5 tca ctg ctg ctg tgg att tca ggc gct tac ggc gat act gtg ctg acc   100
Ser Leu Leu Leu Trp Ile Ser Gly Ala Tyr Gly Asp Thr Val Leu Thr
10              15                  20                  25 cag agc ccc gct ctg gct gtg agc ctg ggc cag cgg gtc aca atc tcc   148
Gln Ser Pro Ala Leu Ala Val Ser Leu Gly Gln Arg Val Thr Ile Ser
            30                  35                  40
```

```
tgc aga gca tca aag agc gtg tcc act ttc atg aac tgg tac cag cag        196
Cys Arg Ala Ser Lys Ser Val Ser Thr Phe Met Asn Trp Tyr Gln Gln
        45                  50                  55 aag tcc ggc cag cag cca aaa ctg ctg atc tac agg gcc agc aat ctg        244
Lys Ser Gly Gln Gln Pro Lys Leu Leu Ile Tyr Arg Ala Ser Asn Leu
    60                  65                  70 gag tcc ggg gtg ccc tct cgc ttc tct gga agt ggc tca ggg acc gac        292
Glu Ser Gly Val Pro Ser Arg Phe Ser Gly Ser Gly Ser Gly Thr Asp
75                  80                  85 ttt acc ctg aca atc gat cct gtc gaa gca gac gat att gcc aac tac        340
Phe Thr Leu Thr Ile Asp Pro Val Glu Ala Asp Asp Ile Ala Asn Tyr
90                  95                  100                 105 tat tgc cag cag tct aat gag ctg cca ctg acc ttc gga agt ggc aca        388
Tyr Cys Gln Gln Ser Asn Glu Leu Pro Leu Thr Phe Gly Ser Gly Thr
                110                 115                 120 aag ctg gaa atc aaa cgg gcc gac gcc gct ccc aca gtg agc att ttt        436
Lys Leu Glu Ile Lys Arg Ala Asp Ala Ala Pro Thr Val Ser Ile Phe
            125                 130                 135 ccc cct agc tcc gag cag ctg acc agt ggc ggg gct tca gtg gtc tgt        484
Pro Pro Ser Ser Glu Gln Leu Thr Ser Gly Gly Ala Ser Val Val Cys
        140                 145                 150 ttc ctg aac aat ttt tac cct aaa gac atc aac gtg aag tgg aaa att        532
Phe Leu Asn Asn Phe Tyr Pro Lys Asp Ile Asn Val Lys Trp Lys Ile
    155                 160                 165 gat ggg agc gaa cgg cag aac gga gtc ctg aat tcc tgg act gac cag        580
Asp Gly Ser Glu Arg Gln Asn Gly Val Leu Asn Ser Trp Thr Asp Gln
170                 175                 180                 185 gat tct aag gac agt acc tat tca atg tct agt act ctg acc ctg aca        628
Asp Ser Lys Asp Ser Thr Tyr Ser Met Ser Ser Thr Leu Thr Leu Thr
                190                 195                 200 aaa gat gag tac gaa cga cac aat tct tat aca tgc gag gcc act cat        676
Lys Asp Glu Tyr Glu Arg His Asn Ser Tyr Thr Cys Glu Ala Thr His
            205                 210                 215 aag act agc acc tcc ccc atc gtg aaa agc ttt aac aga aat gaa tgt        724
Lys Thr Ser Thr Ser Pro Ile Val Lys Ser Phe Asn Arg Asn Glu Cys
        220                 225                 230 tgagtttaaa cgggggaggc taact                                            749
```

<210> SEQ ID NO 19
<211> LENGTH: 233
<212> TYPE: PRT
<213> ORGANISM: Artificial Sequence
<220> FEATURE:
<223> OTHER INFORMATION: Synthetic Construct

<400> SEQUENCE: 19

```
Met Val Leu Gln Thr Gln Val Phe Ile Ser Leu Leu Trp Ile Ser
1               5                   10                  15

Gly Ala Tyr Gly Asp Thr Val Leu Thr Gln Ser Pro Ala Leu Ala Val
            20                  25                  30

Ser Leu Gly Gln Arg Val Thr Ile Ser Cys Arg Ala Ser Lys Ser Val
        35                  40                  45

Ser Thr Phe Met Asn Trp Tyr Gln Gln Lys Ser Gly Gln Gln Pro Lys
    50                  55                  60

Leu Leu Ile Tyr Arg Ala Ser Asn Leu Glu Ser Gly Val Pro Ser Arg
65                  70                  75                  80

Phe Ser Gly Ser Gly Ser Gly Thr Asp Phe Thr Leu Thr Ile Asp Pro
                85                  90                  95

Val Glu Ala Asp Asp Ile Ala Asn Tyr Tyr Cys Gln Gln Ser Asn Glu
```

```
                    100                 105                 110
Leu Pro Leu Thr Phe Gly Ser Gly Thr Lys Leu Glu Ile Lys Arg Ala
            115                 120                 125

Asp Ala Ala Pro Thr Val Ser Ile Phe Pro Pro Ser Ser Glu Gln Leu
130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
                180                 185                 190

Ser Met Ser Ser Thr Leu Thr Leu Thr Lys Asp Glu Tyr Glu Arg His
            195                 200                 205

Asn Ser Tyr Thr Cys Glu Ala Thr His Lys Thr Ser Thr Ser Pro Ile
        210                 215                 220

Val Lys Ser Phe Asn Arg Asn Glu Cys
225                 230

<210> SEQ ID NO 20
<211> LENGTH: 1448
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (26)..(1423)

<400> SEQUENCE: 20
ccagcctccg gactctagag ccacc atg aaa cat ctg tgg ttc ttc ctg ctg       52
                            Met Lys His Leu Trp Phe Phe Leu Leu
                            1               5 ctg gtc gcc gct cct cgg tgg gtc ctg agt gaa gtg cag ctg gtc gaa      100
Leu Val Ala Ala Pro Arg Trp Val Leu Ser Glu Val Gln Leu Val Glu
10                  15                  20                  25 tct ggg ggg ggc ctg gtg cag ccc gga aga tcc atg aag ctg tct tgc      148
Ser Gly Gly Gly Leu Val Gln Pro Gly Arg Ser Met Lys Leu Ser Cys
                30                  35                  40 gcc gct agt gga ctg acc ttc agc aat tat ggc atg gca tgg gtg agg      196
Ala Ala Ser Gly Leu Thr Phe Ser Asn Tyr Gly Met Ala Trp Val Arg
            45                  50                  55 cag gcc cct aag aaa gga ctg gag tgg gtg gct ttc atc agc cac gac      244
Gln Ala Pro Lys Lys Gly Leu Glu Trp Val Ala Phe Ile Ser His Asp
        60                  65                  70 ggc ggg agc tcc tac tat cgc gat agt gtg gaa ggc cgg ttt atc att      292
Gly Gly Ser Ser Tyr Tyr Arg Asp Ser Val Glu Gly Arg Phe Ile Ile
    75                  80                  85 tca aga gac aat gca aag tct aca ctg agt ctg cag atg gac tca ctg      340
Ser Arg Asp Asn Ala Lys Ser Thr Leu Ser Leu Gln Met Asp Ser Leu
90                  95                  100                 105 cga agc gag gat aca gct act tac tat tgc acc aca gca ggc gac tac      388
Arg Ser Glu Asp Thr Ala Thr Tyr Tyr Cys Thr Thr Ala Gly Asp Tyr
                110                 115                 120 tat tcc gac aac gat tgg tac ttc gat ttt tgg gga cca ggc atc atg      436
Tyr Ser Asp Asn Asp Trp Tyr Phe Asp Phe Trp Gly Pro Gly Ile Met
            125                 130                 135 gtc acc gtg tct agt gcc aag act acc ccc cct tct gtg tat cca ctg      484
Val Thr Val Ser Ser Ala Lys Thr Thr Pro Pro Ser Val Tyr Pro Leu
        140                 145                 150
```

```
gct cca gga tcc gca gca cag acc aat tct atg gtg aca ctg ggg tgt      532
Ala Pro Gly Ser Ala Ala Gln Thr Asn Ser Met Val Thr Leu Gly Cys
155                 160                 165 ctg gtc aaa gga tac ttc cct gag cca gtc acc gtg aca tgg aac agc      580
Leu Val Lys Gly Tyr Phe Pro Glu Pro Val Thr Val Thr Trp Asn Ser
170                 175                 180                 185 ggc tcc ctg tca agc gga gtg cac acc ttt cca gca gtc ctg cag tcc      628
Gly Ser Leu Ser Ser Gly Val His Thr Phe Pro Ala Val Leu Gln Ser
                190                 195                 200 gat ctg tac aca ctg tcc tct agt gtc act gtg ccc tca agc acc tgg      676
Asp Leu Tyr Thr Leu Ser Ser Ser Val Thr Val Pro Ser Ser Thr Trp
        205                 210                 215 cct tct gag act gtg acc tgc aat gtc gcc cat cca gct tcc tct act      724
Pro Ser Glu Thr Val Thr Cys Asn Val Ala His Pro Ala Ser Ser Thr
    220                 225                 230 aag gtg gac aag aaa atc gtc ccc agg gat tgc ggc tgt aaa cca tgc      772
Lys Val Asp Lys Lys Ile Val Pro Arg Asp Cys Gly Cys Lys Pro Cys
235                 240                 245 att tgt acc gtc ccc gaa gtg agt tca gtc ttc atc ttt cca ccc aag      820
Ile Cys Thr Val Pro Glu Val Ser Ser Val Phe Ile Phe Pro Pro Lys
250                 255                 260                 265 ccc aaa gac gtg ctg aca att act ctg acc cct aag gtc aca tgt gtg      868
Pro Lys Asp Val Leu Thr Ile Thr Leu Thr Pro Lys Val Thr Cys Val
                270                 275                 280 gtc gtg gac atc agc aaa gac gat ccc gag gtg cag ttc tcc tgg ttt      916
Val Val Asp Ile Ser Lys Asp Asp Pro Glu Val Gln Phe Ser Trp Phe
        285                 290                 295 gtc gac gat gtc gaa gtg cac acc gcc cag aca cag cct agg gag gaa      964
Val Asp Asp Val Glu Val His Thr Ala Gln Thr Gln Pro Arg Glu Glu
    300                 305                 310 cag ttc aac agc acc ttt cgc tct gtg agt gag ctg cca att atg cat     1012
Gln Phe Asn Ser Thr Phe Arg Ser Val Ser Glu Leu Pro Ile Met His
315                 320                 325 cag gac tgg ctg aat ggg aag gaa ttc aaa tgc cga gtg aac agc gct     1060
Gln Asp Trp Leu Asn Gly Lys Glu Phe Lys Cys Arg Val Asn Ser Ala
330                 335                 340                 345 gca ttt ccc gcc cct atc gag aag act att agc aag acc aaa gga cgg     1108
Ala Phe Pro Ala Pro Ile Glu Lys Thr Ile Ser Lys Thr Lys Gly Arg
                350                 355                 360 cct aaa gca cca cag gtg tat aca atc cct cca ccc aag gaa cag atg     1156
Pro Lys Ala Pro Gln Val Tyr Thr Ile Pro Pro Pro Lys Glu Gln Met
        365                 370                 375 gcc aag gat aaa gtg agc ctg aca tgt atg atc act gac ttc ttt cct     1204
Ala Lys Asp Lys Val Ser Leu Thr Cys Met Ile Thr Asp Phe Phe Pro
    380                 385                 390 gag gat att act gtg gaa tgg cag tgg aat ggc cag cct gcc gag aac     1252
Glu Asp Ile Thr Val Glu Trp Gln Trp Asn Gly Gln Pro Ala Glu Asn
395                 400                 405 tac aag aat aca cag cca att atg gac act gat ggg tca tac ttc gtg     1300
Tyr Lys Asn Thr Gln Pro Ile Met Asp Thr Asp Gly Ser Tyr Phe Val
410                 415                 420                 425 tat agc aag ctg aac gtc cag aaa tct aat tgg gaa gct ggg aac acc     1348
Tyr Ser Lys Leu Asn Val Gln Lys Ser Asn Trp Glu Ala Gly Asn Thr
                430                 435                 440 ttc acc tgt agt gtg ctg cac gag gga ctg cat aac cac cat acc gaa     1396
Phe Thr Cys Ser Val Leu His Glu Gly Leu His Asn His His Thr Glu
        445                 450                 455 aag tca ctg agc cat tcc ccc ggc aaa tgagtttaaa cggggaggc taact      1448
Lys Ser Leu Ser His Ser Pro Gly Lys
460                 465
```

<210> SEQ ID NO 21
<211> LENGTH: 466
<212> TYPE: PRT
<213> ORGANISM: Artificial Sequence
<220> FEATURE:
<223> OTHER INFORMATION: Synthetic Construct

<400> SEQUENCE: 21

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Met Lys Leu Ser Cys Ala Ala Ser Gly Leu Thr Phe
        35                  40                  45

Ser Asn Tyr Gly Met Ala Trp Val Arg Gln Ala Pro Lys Lys Gly Leu
    50                  55                  60

Glu Trp Val Ala Phe Ile Ser His Asp Gly Ser Ser Tyr Tyr Arg
65                  70                  75                  80

Asp Ser Val Glu Gly Arg Phe Ile Ile Ser Arg Asp Asn Ala Lys Ser
                85                  90                  95

Thr Leu Ser Leu Gln Met Asp Ser Leu Arg Ser Glu Asp Thr Ala Thr
            100                 105                 110

Tyr Tyr Cys Thr Thr Ala Gly Asp Tyr Tyr Ser Asp Asn Asp Trp Tyr
        115                 120                 125

Phe Asp Phe Trp Gly Pro Gly Ile Met Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365
```

```
Thr Ile Pro Pro Lys Glu Gln Met Ala Lys Asp Lys Val Ser Leu
    370             375             380
Thr Cys Met Ile Thr Asp Phe Phe Pro Glu Asp Ile Thr Val Glu Trp
385             390             395                 400
Gln Trp Asn Gly Gln Pro Ala Glu Asn Tyr Lys Asn Thr Gln Pro Ile
            405             410             415
Met Asp Thr Asp Gly Ser Tyr Phe Val Tyr Ser Lys Leu Asn Val Gln
            420             425             430
Lys Ser Asn Trp Glu Ala Gly Asn Thr Phe Thr Cys Ser Val Leu His
            435             440             445
Glu Gly Leu His Asn His Thr Glu Lys Ser Leu Ser His Ser Pro
    450             455             460
Gly Lys
465

<210> SEQ ID NO 22
<211> LENGTH: 749
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (26)..(724)

<400> SEQUENCE: 22
ccagcctccg gactctagag ccacc atg gtg ctg cag act cag gtg ttc att      52
                            Met Val Leu Gln Thr Gln Val Phe Ile
                            1               5 tca ctg ctg ctg tgg att agc ggc gca tac ggc gac att cag atg acc    100
Ser Leu Leu Leu Trp Ile Ser Gly Ala Tyr Gly Asp Ile Gln Met Thr
 10              15                  20                  25 cag agc ccc tca ctg ctg tcc gca tct gtg ggc gac agg gtc act ctg    148
Gln Ser Pro Ser Leu Leu Ser Ala Ser Val Gly Asp Arg Val Thr Leu
                30                  35                  40 agc tgc aag gct agt cag tca atc tac aac tcc ctg gca tgg tat cag    196
Ser Cys Lys Ala Ser Gln Ser Ile Tyr Asn Ser Leu Ala Trp Tyr Gln
            45                  50                  55 cag aag ctg ggg gag gca cca aaa ctg ctg atc tac gac gcc gat agc    244
Gln Lys Leu Gly Glu Ala Pro Lys Leu Leu Ile Tyr Asp Ala Asp Ser
        60                  65                  70 ctg cag acc gga att cca tcc cgc ttc agc gga tcc gga tct gga aca    292
Leu Gln Thr Gly Ile Pro Ser Arg Phe Ser Gly Ser Gly Ser Gly Thr
    75                  80                  85 gac tac acc ctg aca atc agc tcc ctg cag ccc gaa gat gtg gct acc    340
Asp Tyr Thr Leu Thr Ile Ser Ser Leu Gln Pro Glu Asp Val Ala Thr
 90                  95                 100                 105 tat ttc tgc cag aag tac tat tcc ggg tgg acc ttt ggc ggg gga aca    388
Tyr Phe Cys Gln Lys Tyr Tyr Ser Gly Trp Thr Phe Gly Gly Gly Thr
                110                 115                 120 aag ctg gag ctg aaa cga gcc gat gcc gct cct aca gtc agc att ttt    436
Lys Leu Glu Leu Lys Arg Ala Asp Ala Ala Pro Thr Val Ser Ile Phe
            125                 130                 135 ccc cct tct agt gaa cag ctg act agt ggc ggg gct tca gtg gtc tgt    484
Pro Pro Ser Ser Glu Gln Leu Thr Ser Gly Gly Ala Ser Val Val Cys
        140                 145                 150 ttc ctg aac aat ttt tac cca aaa gac atc aac gtg aag tgg aaa att    532
Phe Leu Asn Asn Phe Tyr Pro Lys Asp Ile Asn Val Lys Trp Lys Ile
    155                 160                 165
```

```
gat gga tct gag aga cag aac ggc gtc ctg aat agt tgg act gac cag      580
Asp Gly Ser Glu Arg Gln Asn Gly Val Leu Asn Ser Trp Thr Asp Gln
170                 175                 180                 185 gat agc aag gac tcc acc tat tct atg tca agc act ctg acc ctg aca      628
Asp Ser Lys Asp Ser Thr Tyr Ser Met Ser Ser Thr Leu Thr Leu Thr
                190                 195                 200 aaa gat gag tac gaa cgg cac aat tct tat aca tgc gag gcc act cat      676
Lys Asp Glu Tyr Glu Arg His Asn Ser Tyr Thr Cys Glu Ala Thr His
            205                 210                 215 aag act agt acc tca cct att gtg aaa agc ttc aac aga aat gaa tgt      724
Lys Thr Ser Thr Ser Pro Ile Val Lys Ser Phe Asn Arg Asn Glu Cys
220                 225                 230 tgagtttaaa cggggggaggc taact                                          749
```

<210> SEQ ID NO 23
<211> LENGTH: 233
<212> TYPE: PRT
<213> ORGANISM: Artificial Sequence
<220> FEATURE:
<223> OTHER INFORMATION: Synthetic Construct

<400> SEQUENCE: 23

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Leu Leu Ser
            20                  25                  30

Ala Ser Val Gly Asp Arg Val Thr Leu Ser Cys Lys Ala Ser Gln Ser
        35                  40                  45

Ile Tyr Asn Ser Leu Ala Trp Tyr Gln Gln Lys Leu Gly Glu Ala Pro
    50                  55                  60

Lys Leu Leu Ile Tyr Asp Ala Asp Ser Leu Gln Thr Gly Ile Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Val Ala Thr Tyr Phe Cys Gln Lys Tyr Tyr
            100                 105                 110

Ser Gly Trp Thr Phe Gly Gly Gly Thr Lys Leu Glu Leu Lys Arg Ala
        115                 120                 125

Asp Ala Ala Pro Thr Val Ser Ile Phe Pro Pro Ser Ser Glu Gln Leu
130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230
```

<210> SEQ ID NO 24
<211> LENGTH: 10
<212> TYPE: PRT
<213> ORGANISM: Rattus norvegicus

```
<400> SEQUENCE: 24

Gly Phe Thr Phe Ser Asp Tyr Gly Met Ala
1               5                   10

<210> SEQ ID NO 25
<211> LENGTH: 17
<212> TYPE: PRT
<213> ORGANISM: Rattus norvegicus

<400> SEQUENCE: 25

Thr Ile Ser Tyr Asp Gly Ser Ser Thr Tyr Tyr Arg Asp Ser Val Lys
1               5                   10                  15

Gly

<210> SEQ ID NO 26
<211> LENGTH: 10
<212> TYPE: PRT
<213> ORGANISM: Rattus norvegicus

<400> SEQUENCE: 26

His Pro Thr Tyr Tyr Tyr Ile Met Asp Ala
1               5                   10

<210> SEQ ID NO 27
<211> LENGTH: 11
<212> TYPE: PRT
<213> ORGANISM: Rattus norvegicus

<400> SEQUENCE: 27

Arg Ala Ser Lys Ser Val Ser Thr Phe Met Asn
1               5                   10

<210> SEQ ID NO 28
<211> LENGTH: 7
<212> TYPE: PRT
<213> ORGANISM: Rattus norvegicus

<400> SEQUENCE: 28

Arg Ala Ser Asn Leu Glu Ser
1               5

<210> SEQ ID NO 29
<211> LENGTH: 9
<212> TYPE: PRT
<213> ORGANISM: Rattus norvegicus

<400> SEQUENCE: 29

Gln Gln Ser Asn Glu Leu Pro Leu Thr
1               5

<210> SEQ ID NO 30
<211> LENGTH: 10
<212> TYPE: PRT
<213> ORGANISM: Rattus norvegicus

<400> SEQUENCE: 30

Gly Leu Thr Phe Ser Asn Tyr Gly Met Ala
1               5                   10

<210> SEQ ID NO 31
<211> LENGTH: 17
<212> TYPE: PRT
<213> ORGANISM: Rattus norvegicus
```

```
<400> SEQUENCE: 31

Phe Ile Ser His Asp Gly Gly Ser Ser Tyr Tyr Arg Asp Ser Val Glu
1               5                   10                  15

Gly

<210> SEQ ID NO 32
<211> LENGTH: 14
<212> TYPE: PRT
<213> ORGANISM: Rattus norvegicus

<400> SEQUENCE: 32

Ala Gly Asp Tyr Tyr Ser Asp Asn Asp Trp Tyr Phe Asp Phe
1               5                   10

<210> SEQ ID NO 33
<211> LENGTH: 11
<212> TYPE: PRT
<213> ORGANISM: Rattus norvegicus

<400> SEQUENCE: 33

Lys Ala Ser Gln Ser Ile Tyr Asn Ser Leu Ala
1               5                   10

<210> SEQ ID NO 34
<211> LENGTH: 7
<212> TYPE: PRT
<213> ORGANISM: Rattus norvegicus

<400> SEQUENCE: 34

Asp Ala Asp Ser Leu Gln Thr
1               5

<210> SEQ ID NO 35
<211> LENGTH: 8
<212> TYPE: PRT
<213> ORGANISM: Rattus norvegicus

<400> SEQUENCE: 35

Gln Lys Tyr Tyr Ser Gly Trp Thr
1               5
```

MONOCLONAL ANTIBODIES TO HUMAN FIBROBLAST GROWTH FACTOR RECEPTOR 2 (HFGFR2) AND METHODS OF USE THEREOF

CROSS-REFERENCE TO RELATED APPLICATIONS

The present application is a U.S. national stage application of International Patent Application No. PCT/JP2016/062297, filed Apr. 19, 2016, which claims the benefit of priority to Japanese Patent Application No. 2015-085942, filed Apr. 20, 2015, the entireties of which are incorporated herein by reference.

TECHNICAL FIELD

The present invention relates to a novel antibody, a functional fragment of the antibody, a modified form of the antibody, a nucleotide comprising a nucleotide sequence encoding the amino acid sequence of the antibody, a vector having an insert of the nucleotide, a cell comprising the nucleotide or the vector, a method for producing the antibody, comprising the step of culturing the cell, a pharmaceutical composition, a composition for diagnosis or testing, a kit, etc.

BACKGROUND ART

Fibroblast growth factors (FGFs) are known to play an important role in embryogenesis, tissue homeostasis, and metabolism via FGF receptor (FGFR) signals (Non Patent Literature 1). In humans, there are 22 FGFs (FGF1 to FGF14 and FGF16 to FGF23) and 4 FGF receptors (FGFR1 to FGFR4; hereinafter, collectively referred to as "FGFRs") having a tyrosine kinase domain. These FGFRs are each composed of an extracellular region comprising a ligand binding site composed of 2 or 3 immunoglobulin-like domains (IgD1 to IgD3), a single-pass transmembrane region, and an intracellular region comprising the tyrosine kinase domain. FGFR1, FGFR2, and FGFR3 each have two splicing variants called IIIb and IIIc. These isoforms differ in the sequence of approximately 50 amino acids in the latter half of IgD3 and exhibit distinctive tissue distribution and ligand specificity. It is generally known that the IIIb isoform is expressed in epithelial cells, while the IIIc isoform is expressed in mesenchymal cells. The binding of FGFs to FGFRs induces the activation of many signaling pathways (Non Patent Literature 1). As a result, FGFs and their corresponding receptors control a wide range of cell functions including growth, differentiation, migration, and survival.

The abnormal activation of FGFRs is known to participate in particular types of malignant tumor development in humans (Non Patent Literature 1 and 2). Particularly, FGFR2 signal abnormalities such as the overexpression of FGFR2 and its ligand, receptor mutations or gene amplification, and isoform switching, have been found to be associated with cancer (Non Patent Literature 2, 3, 4, 5, 6 and 7).

As mentioned above, the possibility of FGFR2 as an excellent therapeutic target for cancer has been suggested. In fact, monoclonal antibodies against FGFR2 have been obtained and are under clinical trial (Non Patent Literatures 8, 9, 10, and 11).

For these reasons, the provision of methods capable of detecting expression of FGFR2 and its splicing variants is useful in the testing or diagnosis of FGFR2-related diseases such as cancer or of FGFR2 expression.

Many monoclonal antibodies which recognize human FGFR2 are known. However, very few of these known antibodies are capable of being used for immunohistological staining. For instance, only one clone known as 1G3 (Non Patent Literature 12) recognises denatured FGFR2 when fixed in formalin, which means it is capable of immunohistological staining. Neither antibody cross-reactivity to the denatured form of other FGFR families when fixed in formalin, nor selective recognition of the denatured human FGFR2 splicing variants IIIb and IIIc when fixed in formalin, have been reported.

A monoclonal antibody which selectively recognizes a denatured splicing variant IIIb of human FGFR2 fixed in formalin has been reported (Patent Literature 1). However, no monoclonal antibody which selectively recognizes a denatured human FGFR2 IIIc has been identified.

CITATION LIST

Patent Literature

Patent Literature 1: WO2013/154206

Non Patent Literature

Non Patent Literature 1: Eswarakumar, V. P., et al., J. Cytokine Growth Factor Rev., April 2005, Vol. 16 (No. 2), p. 139-149, published online on Feb. 1, 2005, Review Non Patent Literature 2: Turner, N. and Grose, R., Nat. Rev. Cancer, February 2010, Vol. 10 (No. 2), p. 116-129, Review Non Patent Literature 3: Easton, D. F., et al., Nature, Jun. 28, 2007, Vol. 447 (No. 7148), p. 1087-1093

Non Patent Literature 4: Hunter D J, et al., Nat. Genet., July 2007, Vol. 39 (No. 7), p. 870-874, published online on May 27, 2007

Non Patent Literature 5: Katoh, Y. and Katoh, M., Int. J. Mol. Med., March 2009, Vol. 23 (No. 3), p. 307-311, Review Non Patent Literature 6: Chaffer, C. L., et al., Differentiation, November 2007, Vol. 75 (No. 9), p. 831-842, published online on Aug. 14, 2007, Review Non Patent Literature 7: Carstens, R. P., et al., Oncogene, Dec. 18, 1997, Vol. 15 (No. 25), p. 3059-3065

Non Patent Literature 8: Zhao, W. M., et al., Clin. Cancer Res., Dec. 1, 2010, Vol. 16 (No. 23), p. 5750-5758, published online on Jul. 29, 2010

Non Patent Literature 9: Bai, A., et al., Cancer Res., Oct. 1, 2010, Vol. 70 (No. 19), p. 7630-7639, published online on Aug. 13, 2010

Non Patent Literature 10: Clinical Trials. gov, Clinical Trials. gov Identifier: NCT01881217, published online on Jun. 13, 2013

Non Patent Literature 11: Clinical Trials. gov, Clinical Trials. gov Identifier: NCT02368951, published online on Feb. 16, 2015

Non Patent Literature 12: Vermeulen, J. F., et al., PloS One, published in 2013, Vol. 8 (No. 1), e53353

SUMMARY OF THE INVENTION

Technical Problem

An object of the present invention is to provide an antibody against FGFR2.

Another object of the present invention is to provide a composition for diagnosis or testing, etc., comprising an anti-FGFR2 antibody.

An alternative object of the present invention includes the provision of a nucleotide encoding the amino acid sequence of the antibody, a vector having an insert of the nucleotide, a cell comprising the nucleotide or the vector, a method for producing the antibody, comprising the step of culturing the cell, etc.

A further alternative object of the present invention is to provide a pharmaceutical composition and a method of treatment and/or a composition for use in a method of treatment.

Solution to the Problem

The present inventors have conducted diligent studies to attain the objects and consequently completed the present invention by developing a novel anti-FGFR2 antibody and have found that FGFR2 can be detected using the antibody.

The present invention relates to:

(1) A monoclonal antibody or an antigen binding fragment thereof which has the following properties (i) to (iii):
 (i) specifically binds to non-denatured human fibroblast growth factor receptor 2 (hFGFR2) IIIc;
 (ii) specifically binds to none of the following: non-denatured human fibroblast growth factor receptor 1 (hFGFR1); non-denatured human fibroblast growth factor receptor 3 (hFGFR3); and non-denatured human fibroblast growth factor receptor 4 (hFGFR4); and
 (iii) specifically binds to denatured hFGFR2 IIIc in a preparation fixed in formalin;

(2) The monoclonal antibody or antigen binding fragment thereof according to (1), wherein the monoclonal antibody or antigen binding fragment thereof specifically binds to non-denatured human fibroblast growth factor receptor 2 (hFGFR2) IIIb and denatured hFGFR2 IIIb in a preparation fixed in formalin;

(3) The monoclonal antibody or antigen binding fragment thereof according to (1) or (2), wherein the monoclonal antibody consists of a heavy chain comprising a CDRH1 consisting of the amino acid sequence represented by SEQ ID NO: 30 (FIG. 20) or an amino acid sequence derived from the amino acid sequence by the substitution of one or two amino acids, a CDRH2 consisting of the amino acid sequence represented by SEQ ID NO: 31 (FIG. 20) or an amino acid sequence derived from the amino acid sequence by the substitution of one or two amino acids, and a CDRH3 consisting of the amino acid sequence represented by SEQ ID NO: 32 (FIG. 20) or an amino acid sequence derived from the amino acid sequence by the substitution of one or two amino acids; and a light chain comprising a CDRL1 consisting of the amino acid sequence represented by SEQ ID NO: 33 (FIG. 20) or an amino acid sequence derived from the amino acid sequence by the substitution of one or two amino acids, a CDRL2 consisting of the amino acid sequence represented by SEQ ID NO: 34 (FIG. 20) or an amino acid sequence derived from the amino acid sequence by the substitution of one or two amino acids, and a CDRL3 consisting of the amino acid sequence represented by SEQ ID NO: 35 (FIG. 20) or an amino acid sequence derived from the amino acid sequence by the substitution of one or two amino acids;

(4) The monoclonal antibody or antigen binding fragment thereof according to (3), wherein the monoclonal antibody consists of a heavy chain comprising a CDRH1 consisting of the amino acid sequence represented by SEQ ID NO: 30 (FIG. 20), a CDRH2 consisting of the amino acid sequence represented by SEQ ID NO: (FIG. 20), and a CDRH3 consisting of the amino acid sequence represented by SEQ ID NO: 32 (FIG. 20); and a light chain comprising a CDRL1 consisting of the amino acid sequence represented by SEQ ID NO: 33 (FIG. 20), a CDRL2 consisting of the amino acid sequence represented by SEQ ID NO: 34 (FIG. 20), and a CDRL3 consisting of the amino acid sequence represented by SEQ ID NO: 35 (FIG. 20);

(5) The monoclonal antibody or antigen binding fragment thereof according to (1) or (2), wherein the monoclonal antibody comprises the amino acid sequences of a heavy chain variable region and a light chain variable region described in any one of the following (i) to (iv):
 (i) the amino acid sequence of a heavy chain variable region represented by SEQ ID NO: 8 (FIG. 15B) and the amino acid sequence of a light chain variable region represented by SEQ ID NO: 10 (FIG. 15D);
 (ii) an amino acid sequence 95% or more identical to the amino acid sequence of a heavy chain variable region represented by SEQ ID NO: 8 (FIG. 15B) and an amino acid sequence 95% or more identical to the amino acid sequence of a light chain variable region represented by SEQ ID NO: 10 (FIG. 15D);
 (iii) an amino acid sequence derived from the amino acid sequence of a heavy chain variable region represented by SEQ ID NO: 8 (FIG. 15B) by the substitution, deletion, insertion, or addition of 1 to several amino acids and an amino acid sequence derived from the amino acid sequence of a light chain variable region represented by SEQ ID NO: 10 (FIG. 15D) by the substitution, deletion, insertion, or addition of 1 to several amino acids; and
 (iv) an amino acid sequence encoded by the nucleotide sequence of a polynucleotide that hybridizes under stringent conditions to a polynucleotide comprising a nucleotide sequence encoding the amino acid sequence of a heavy chain variable region represented by SEQ ID NO: 8 (FIG. 15B), and an amino acid sequence encoded by the nucleotide sequence of a polynucleotide that hybridizes under stringent conditions to a polynucleotide comprising a nucleotide sequence encoding the amino acid sequence of a light chain variable region represented by SEQ ID NO: 10 (FIG. 15D);

(6) The monoclonal antibody or antigen binding fragment thereof according to any one of (1) to (5), wherein the monoclonal antibody comprises the amino acid sequence of a heavy chain represented by SEQ ID NO: 21 (FIG. 18B) and the amino acid sequence of a light chain represented by SEQ ID NO: 23 (FIG. 18D);

(7) The monoclonal antibody or antigen binding fragment thereof according to (1) or (2), wherein the monoclonal antibody or antigen binding fragment thereof binds to a site on hFGFR2 IIIc and/or hFGFR2 IIIb which is recognized by an antibody or an antigen binding fragment thereof according to any one of (3) to (6), or competes with an antibody or an antigen binding fragment thereof according to any one of (3) to (6) for binding to hFGFR2 IIIc and/or hFGFR2 IIIb;

(8) The monoclonal antibody or antigen binding fragment thereof according to (1), wherein the monoclonal antibody or antigen binding fragment thereof binds to neither non-denatured human fibroblast growth factor receptor 2 (hFGFR2) IIIb nor denatured hFGFR2 IIIb in a preparation fixed in formalin;

(9) The monoclonal antibody or antigen binding fragment thereof according to (1) or (8), wherein the monoclonal antibody consists of a heavy chain comprising a CDRH1 consisting of the amino acid sequence represented by SEQ ID NO: 24 (FIG. 19) or an amino acid sequence derived from the amino acid sequence by the substitution of one or two amino acids, a CDRH2 consisting of the amino acid sequence represented by SEQ ID NO: 25 (FIG. 19) or an amino acid sequence derived from the amino acid sequence by the substitution of one or two amino acids, and a CDRH3 consisting of the amino acid sequence represented by SEQ ID NO: 26 (FIG. 19) or an amino acid sequence derived from the amino acid sequence by the substitution of one or two amino acids; and a light chain comprising a CDRL1 consisting of the amino acid sequence represented by SEQ ID NO: 27 (FIG. 19) or an amino acid sequence derived from the amino acid sequence by the substitution of one or two amino acids, a CDRL2 consisting of the amino acid sequence represented by SEQ ID NO: 28 (FIG. 19) or an amino acid sequence derived from the amino acid sequence by the substitution of one or two amino acids, and a CDRL3 consisting of the amino acid sequence represented by SEQ ID NO: 29 (FIG. 19) or an amino acid sequence derived from the amino acid sequence by the substitution of one or two amino acids;

(10) The monoclonal antibody or antigen binding fragment thereof according to (9), wherein the monoclonal antibody consists of a heavy chain comprising a CDRH1 consisting of the amino acid sequence represented by SEQ ID NO: 24 (FIG. 19), a CDRH2 consisting of the amino acid sequence represented by SEQ ID NO: 25 (FIG. 19), and a CDRH3 consisting of the amino acid sequence represented by SEQ ID NO: 26 (FIG. 19); and a light chain comprising a CDRL1 consisting of the amino acid sequence represented by SEQ ID NO: 27 (FIG. 19), a CDRL2 consisting of the amino acid sequence represented by SEQ ID NO: 28 (FIG. 19), and a CDRL3 consisting of the amino acid sequence represented by SEQ ID NO: 29 (FIG. 19);

(11) The monoclonal antibody or antigen binding fragment thereof according to (1) or (8), wherein the monoclonal antibody comprises the amino acid sequences of a heavy chain variable region and a light chain variable region described in any one of the following (i) to (iv):

(i) the amino acid sequence of a heavy chain variable region represented by SEQ ID NO: 3 (FIG. 14B) and the amino acid sequence of a light chain variable region represented by SEQ ID NO: 6 (FIG. 14D);

(ii) an amino acid sequence 95% or more identical to the amino acid sequence of a heavy chain variable region represented by SEQ ID NO: 3 (FIG. 14B) and an amino acid sequence 95% or more identical to the amino acid sequence of a light chain variable region represented by SEQ ID NO: 6 (FIG. 14D);

(iii) an amino acid sequence derived from the amino acid sequence of a heavy chain variable region represented by SEQ ID NO: 3 (FIG. 14B) by the substitution, deletion, insertion, or addition of 1 to several amino acids and an amino acid sequence derived from the amino acid sequence of a light chain variable region represented by SEQ ID NO: 6 (FIG. 14D) by the substitution, deletion, insertion, or addition of 1 to several amino acids; and (iv) an amino acid sequence encoded by the nucleotide sequence of a polynucleotide that hybridizes under stringent conditions to a polynucleotide comprising a nucleotide sequence encoding the amino acid sequence of a heavy chain variable region represented by SEQ ID NO: 3 (FIG. 14B), and an amino acid sequence encoded by the nucleotide sequence of a polynucleotide that hybridizes under stringent conditions to a polynucleotide comprising a nucleotide sequence encoding the amino acid sequence of a light chain variable region represented by SEQ ID NO: 6 (FIG. 14D);

(12) The monoclonal antibody or antigen binding fragment thereof according to any one of (1) and (8) to (11), wherein the monoclonal antibody comprises the amino acid sequence of a heavy chain represented by SEQ ID NO: 15 (FIG. 17B) and the amino acid sequence of a light chain represented by SEQ ID NO: 19 (FIG. 17D);

(13) The monoclonal antibody or antigen binding fragment thereof according to (1) or (8), wherein the monoclonal antibody or antigen binding fragment thereof binds to a site on hFGFR2 IIIc which is recognized by an antibody or an antigen binding fragment thereof according to any one of (9) to (12), or competes with an antibody or an antigen binding fragment thereof according to any one of (9) to (12) for binding to hFGFR2 IIIc;

(14) A polynucleotide encoding a monoclonal antibody according to any one of (1) to (13);

(15) A vector comprising a polynucleotide according to (14);

(16) A cell comprising a polynucleotide according to (14) or a vector according to (15);

(17) A method for producing a monoclonal antibody or an antigen binding fragment thereof according to (1), (2), or (8), comprising the following steps (i) and (ii):

(i) culturing a cell according to (16); and (ii) recovering the monoclonal antibody or antigen binding fragment thereof from the cultures of step (i);

(18) A monoclonal antibody or an antigen binding fragment thereof which is obtained by a method according to (17);

(19) A composition comprising a monoclonal antibody or an antigen binding fragment thereof according to any one of (1) to (7) and (18);

(20) The composition according to (19), wherein the composition is used in a method for detecting or assaying hFGFR2 IIIc and hFGFR2 IIIb in a tissue preparation which is paraffin-embedded and then deparaffinized, the tissue preparation comprising the monoclonal antibody or antigen binding fragment thereof according to any one of (1) to (7) and (18) (hereinafter, this tissue preparation is simply referred to as a "preparation");

(21) The composition according to (20), wherein the preparation is subjected to heat treatment following the deparaffinization treatment;

(22) The composition according to (21), wherein the heat treatment is performed at 90 to 100° C. and at pH 8 to 10;

(23) The composition according to any one of (19) to (22), wherein the composition is used in a method for detecting or assaying hFGFR2 IIIc and hFGFR2 IIIb in a preparation, the method comprising the step of contacting the monoclonal antibody or antigen binding fragment thereof according to any one of (1) to (7) and (18) or the composition according to (19) with the test preparation;

(24) The composition according to (23), wherein the method for detecting or assaying hFGFR2 IIIc and hFGFR2 IIIb further comprises the step of determining the test preparation to be positive when hFGFR2 IIIc and hFGFR2 IIIb are detected or assayed in the test preparation or when the expression levels of hFGFR2 IIIc and hFGFR2 IIIb in the test preparation are equivalent to or higher than predetermined references; and determining the test preparation to be negative when neither hFGFR2 IIIc nor hFGFR2 IIIb is detected or assayed in the test preparation or when the expression levels of hFGFR2 IIIc and hFGFR2 IIIb in the test preparation are equivalent to or lower than the predetermined references;

(25) The composition according to any one of (19) to (24), wherein the composition is used in a method for testing or diagnosing a hFGFR2 IIIc- and hFGFR2 IIIb-positive disease;

(26) The composition according to (25), wherein the method for testing or diagnosing a hFGFR2 IIIc- and hFGFR2 IIIb-positive disease comprises determining a test subject, from which a test preparation determined to be positive in the detection or assay of hFGFR2 IIIc and hFGFR2 IIIb is derived, to be suitable for a method for treating or preventing the hFGFR2 IIIc- and hFGFR2 IIIb-positive disease, comprising the step of administering an antibody specifically binding to hFGFR2 IIIc and hFGFR2 IIIb or an antigen binding fragment thereof, and determining a test subject from which a test preparation determined to be negative therein is derived, to be not suitable for the method for treating or preventing the hFGFR2 IIIc- and hFGFR2 IIIb-positive disease, comprising the step of administering an antibody specifically binding to hFGFR2 IIIc and hFGFR2 IIIb or an antigen binding fragment thereof;

(27) The composition according to (25) or (26), wherein the hFGFR2 IIIc- and hFGFR2 IIIb-positive disease is hFGFR2 IIIc- and hFGFR2 IIIb-positive cancer;

(28) A pharmaceutical composition which is administered to a test subject described in any one of the following (i) to (iii), the pharmaceutical composition comprising an antibody specifically binding to hFGFR2 IIIc and hFGFR2 IIIb or an antigen binding fragment thereof:
(i) a test subject from which a test preparation is derived, wherein hFGFR2 IIIc and hFGFR2 IIIb are detected or assayed in the test preparation using a composition according to any one of (19) to (23) and (25);
(ii) a test subject from which a test preparation determined to be positive in the detection or assay of hFGFR2 IIIc and hFGFR2 IIIb using a composition according to (24) is derived; and
(iii) a test subject determined, using a composition according to (26) or (27), to be suitable for the treatment or prevention of a hFGFR2 IIIc- and hFGFR2 IIIb-positive disease, comprising the step of administering an antibody specifically binding to hFGFR2 IIIc and hFGFR2 IIIb or an antigen binding fragment thereof;

(29) A method for detecting or assaying hFGFR2 IIIc and hFGFR2 IIIb, comprising the following step (i) or steps (i) and (ii):
(i) contacting a monoclonal antibody or an antigen binding fragment of the antibody according to any one of (1) to (7) and (18) or a composition according to (19) to (22) with a test preparation; and
(ii) determining the test preparation to be positive when hFGFR2 IIIc and hFGFR2 IIIb are detected or assayed in the test preparation or when the expression levels of hFGFR2 IIIc and hFGFR2 IIIb in the test preparation are equivalent to or higher than predetermined references; and determining the test preparation to be negative when neither hFGFR2 IIIc nor hFGFR2 IIIb is detected or assayed in the test preparation or when the expression levels of hFGFR2 IIIc and hFGFR2 IIIb in the test preparation are equivalent to or lower than the predetermined references;

(30) A method for identifying a suitable individual for treating with a pharmaceutical composition comprising an antibody specifically binding to hFGFR2 or an antigen binding fragment of the antibody, the method comprising the following step (i) or steps (i) and (ii):
(i) contacting an antibody or an antigen binding fragment of the antibody according to any one of (1) to (7) and (18) or a composition according to (19) to (22) with an individual-derived sample; and
(ii) determining the individual to be positive when hFGFR2 IIIc and hFGFR2 IIIb are detected or assayed in the individual-derived sample or when the expression levels of hFGFR2 IIIc and hFGFR2 IIIb in the individual-derived sample are equivalent to or higher than predetermined references, and determining the individual to be negative when neither hFGFR2 IIIc nor hFGFR2 IIIb is detected or assayed in the individual-derived sample or when the expression levels of hFGFR2 IIIc and hFGFR2 IIIb in the individual-derived sample are equivalent to or lower than the predetermined references;

(31) A method for detecting or assaying hFGFR2 IIIc, comprising the following steps (i) to (iii):
(i) contacting a composition comprising an antibody or an antigen binding fragment of the antibody according to any one of (1) to (7) and (18) with a test preparation to detect or assay hFGFR2 IIIb and hFGFR2 IIIc in the test preparation;
(ii) contacting a composition comprising an antibody specifically binding to hFGFR2 IIIb or an antigen binding fragment of the antibody with the test preparation to detect or assay hFGFR2 IIIb in the test preparation; and
(iii) comparing the results of the detection or assay in step (i) with the results of detection or assay in step (ii) or subtracting the results of detection or assay in step (ii) from the results of detection or assay in step (i) to obtain detection or assay results or a value of hFGFR2 IIIc in the sample;

(32) The method according to any one of (29) to (31), wherein the method is used in a method for testing or diagnosing a hFGFR2 IIIc- and hFGFR2 IIIb-positive disease;

(33) The method according to (30), wherein the method is used in a method for identifying an individual having a hFGFR2 IIIc- and hFGFR2 IIIb-positive disease or being at risk thereof;

(34) A method for treating a hFGFR2 IIIc- and hFGFR2 IIIb-positive disease, comprising administering a pharmaceutical composition comprising an antibody specifically binding to hFGFR2 or an antigen binding fragment of the antibody to a test subject described in any one of (i) to (iii) of (28);

(35) A kit for testing or diagnosing a hFGFR2 IIIc- and hFGFR2 IIIb-positive disease, comprising an antibody or an antigen binding fragment of the antibody according to any one of (1) to (7) and (18);

(36) The method according to any one of (32) to (34) or the kit according to (35), wherein the hFGFR2 IIIc- and hFGFR2 IIIb-positive disease is hFGFR2 IIIc- and hFGFR2 IIIb-positive cancer;

(37) A composition comprising a monoclonal antibody or an antigen binding fragment thereof according to any one of (1), (8) to (13), and (18);

(38) The composition according to (37), wherein the composition is used in a method for detecting or assaying hFGFR2 IIIc in a tissue preparation paraffin-embedded and then deparaffinized, the tissue preparation comprising the monoclonal antibody or antigen binding fragment thereof according to any one of (1), (8) to (13), and (18) (hereinafter, this tissue preparation is simply referred to as a "preparation");

(39) The composition according to (38), wherein the preparation is subjected to enzymatic treatment following the deparaffinization treatment;

(40) The composition according to (39), wherein the enzymatic treatment is the reaction of protease at 20 to 38° C.;

(41) The composition according to any one of (37) to (40), wherein the composition is used in a method for detecting or assaying hFGFR2 IIIc in a preparation, the method comprising the step of contacting the monoclonal antibody or antigen binding fragment thereof according to any one of (1), (8) to (13), and (18) or the composition according to (37) with the test preparation;

(42) The composition according to (41), wherein the method for detecting or assaying hFGFR2 IIIc further comprises the step of determining the test preparation to be positive when hFGFR2 IIIc is detected or assayed in the test preparation or when the expression level of hFGFR2 IIIc in the test preparation is equivalent to or higher than a predetermined reference; and determining the test preparation to be negative when no hFGFR2 IIIc is detected or assayed in the test preparation or when the expression level of hFGFR2 IIIc in the test preparation is equivalent to or lower than the predetermined reference;

(43) The composition according to any one of (37) to (42), wherein the composition is used in a method for testing or diagnosing a hFGFR2 IIIc-positive disease;

(44) The composition according to (43), wherein the method for testing or diagnosing a hFGFR2 IIIc-positive disease comprises determining a test subject from which a test preparation determined to be positive in the detection or assay of hFGFR2 IIIc is derived, to be suitable for a method for treating or preventing the hFGFR2 IIIc-positive disease, comprising the step of administering an antibody specifically binding to hFGFR2 IIIc or an antigen binding fragment thereof, and determining a test subject from which a test preparation determined to be negative therein is derived, to be not suitable for the method for treating or preventing the hFGFR2 IIIc-positive disease, comprising the step of administering an antibody specifically binding to hFGFR2 IIIc or an antigen binding fragment thereof;

(45) The composition according to (43) or (44), wherein the hFGFR2 IIIc-positive disease is hFGFR2 IIIc-positive cancer;

(46) A pharmaceutical composition which is administered to a test subject described in any one of the following (i) to (iii), the pharmaceutical composition comprising an antibody specifically binding to hFGFR2 IIIc or an antigen binding fragment thereof:
(i) a test subject from which a test preparation is derived, wherein hFGFR2 IIIc is detected or assayed in the test preparation using a composition according to any one of (37) to (40) and (43);
(ii) a test subject from which a test preparation determined to be positive in the detection or assay of hFGFR2 IIIc using a composition according to (42) is derived; and
(iii) a test subject determined, using a composition according to (44) or (45), to be suitable for the treatment or prevention of a hFGFR2 IIIc-positive disease, comprising the step of administering an antibody specifically binding to hFGFR2 IIIc or an antigen binding fragment thereof; and

(47) The pharmaceutical composition according to (46), wherein the hFGFR2 IIIc-positive disease is hFGFR2 IIIc-positive cancer.

BRIEF DESCRIPTION OF DRAWINGS

FIG. 1 is a diagram showing the results of testing binding activity of mouse chimeric anti-FGFR2 antibodies FR2-2nd_#028 and FR2-2nd_#023 against each non-denatured molecule of the human FGFR family. The vertical axis represents a relative value of the average fluorescence intensity assayed by flow cytometry.

FIG. 2A is a diagram showing the results of immunostaining blocks of 293α cells forced to express a FGFR1 IIIb or FGFR1 IIIc molecule, using a commercially available anti-FGFR2 antibody (18601).

FIG. 2B is a diagram showing the results of immunostaining blocks of 293α cells forced to express a FGFR2 IIIb or FGFR2 IIIc molecule, using a commercially available anti-FGFR2 antibody (18601).

FIG. 2C is a diagram showing the results of immunostaining blocks of 293α cells forced to express a FGFR3 IIIb or FGFR3 IIIc molecule, using a commercially available anti-FGFR2 antibody (18601).

FIG. 2D is a diagram showing the results of immunostaining blocks of 293α cells forced to express a FGFR4 molecule and blocks of 293α cells transfected with an empty vector, using a commercially available anti-FGFR2 antibody (18601).

FIG. 3 is a diagram showing the results of immunostaining blocks of SNU-16 (A), NCI-H716 (B), and KATO III (C) cells using a commercially available anti-FGFR2 antibody (18601).

FIG. 4A is a diagram showing the results of immunostaining blocks of 293α cells forced to express a FGFR1 IIIb or FGFR1 IIIc molecule, using a rat anti-FGFR2 antibody FR2-2nd_#028.

FIG. 4B is a diagram showing the results of immunostaining blocks of 293α cells forced to express a FGFR2 IIIb or FGFR2 IIIc molecule, using a rat anti-FGFR2 antibody FR2-2nd_#028.

FIG. 4C is a diagram showing the results of immunostaining blocks of 293α cells forced to express a FGFR3 IIIb or FGFR3 IIIc molecule, using a rat anti-FGFR2 antibody FR2-2nd_#028.

FIG. 4D is a diagram showing the results of immunostaining blocks of 293α cells forced to express a FGFR4 molecule and blocks of 293α cells transfected with an empty vector, using a rat anti-FGFR2 antibody FR2-2nd_#028.

FIG. 5A is a diagram showing the results of immunostaining blocks of 293α cells forced to express a FGFR1 IIIb or FGFR1 IIIc molecule, using a mouse chimeric anti-FGFR2 antibody FR2-2nd_#028.

FIG. 5B is a diagram showing the results of immunostaining blocks of 293α cells forced to express a FGFR2 IIIb or FGFR2 IIIc molecule, using a mouse chimeric anti-FGFR2 antibody FR2-2nd_#028.

FIG. 5C is a diagram showing the results of immunostaining blocks of 293α cells forced to express a FGFR3 IIIb or FGFR3 IIIc molecule, using a mouse chimeric anti-FGFR2 antibody FR2-2nd_#028.

FIG. 5D is a diagram showing the results of immunostaining blocks of 293α cells forced to express a FGFR4 molecule and blocks of 293α cells transfected with an empty vector, using a mouse chimeric anti-FGFR2 antibody FR2-2nd_#028.

FIG. 6 is a diagram showing the results of immunostaining blocks of SNU-16 (A), NCI-H716 (B), and KATO III (C) cells using a rat anti-FGFR2 antibody FR2-2nd_#028.

FIG. 7 is a diagram showing the results of immunostaining blocks of SNU-16 (A), NCI-H716 (B), and KATO III (C) cells using a mouse chimeric anti-FGFR2 antibody FR2-2nd_#028.

FIG. 8 is a diagram showing the results of immunostaining a xenograft tumor sample of NCI-H716 cells using a rat anti-FGFR2 antibody FR2-2nd_#028 (upper: low magnification, lower: high magnification of the upper boxed site).

FIG. 9A is a diagram showing the results of immunostaining blocks of 293α cells forced to express a FGFR1 IIIb or FGFR1 IIIc molecule, using a rat anti-FGFR2 antibody FR2-2nd_#023.

FIG. 9B is a diagram showing the results of immunostaining blocks of 293α cells forced to express a FGFR2 IIIb or FGFR2 IIIc molecule, using a rat anti-FGFR2 antibody FR2-2nd_#023.

FIG. 9C is a diagram showing the results of immunostaining blocks of 293α cells forced to express a FGFR3 IIIb or FGFR3 IIIc molecule, using a rat anti-FGFR2 antibody FR2-2nd_#023.

FIG. 9D is a diagram showing the results of immunostaining blocks of 293α cells forced to express a FGFR4 molecule and blocks of 293α cells transfected with an empty vector, using a rat anti-FGFR2 antibody FR2-2nd_#023.

FIG. 10A is a diagram showing the results of immunostaining blocks of 293α cells forced to express a FGFR1 IIIb or FGFR1 IIIc molecule, using a mouse chimeric anti-FGFR2 antibody FR2-2nd_#023.

FIG. 10B is a diagram showing the results of immunostaining blocks of 293α cells forced to express a FGFR2 IIIb or FGFR2 IIIc molecule, using a mouse chimeric anti-FGFR2 antibody FR2-2nd_#023.

FIG. 10C is a diagram showing the results of immunostaining blocks of 293α cells forced to express a FGFR3 IIIb or FGFR3 IIIc molecule, using a mouse chimeric anti-FGFR2 antibody FR2-2nd_#023.

FIG. 10D is a diagram showing the results of immunostaining blocks of 293α cells forced to express a FGFR4 molecule and blocks of 293α cells transfected with an empty vector, using a mouse chimeric anti-FGFR2 antibody FR2-2nd_#023.

FIG. 11 is a diagram showing the results of immunostaining blocks of SNU-16 (A), NCI-H716 (B), and KATO III (C) cells using a rat anti-FGFR2 antibody FR2-2nd_#023.

FIG. 12 is a diagram showing the results of immunostaining blocks of SNU-16 (A), NCI-H716 (B), and KATO III (C) cells using a mouse chimeric anti-FGFR2 antibody FR2-2nd_#023.

FIG. 13A is a diagram showing the results of immunostaining blocks of 293α cells forced to express a FGFR1 IIIb or FGFR1 IIIc molecule, using a commercially available anti-FGFR2 antibody (ab58201).

FIG. 13B is a diagram showing the results of immunostaining blocks of 293α cells forced to express a FGFR2 IIIb or FGFR2 IIIc molecule, using a commercially available anti-FGFR2 antibody (ab58201).

FIG. 13C is a diagram showing the results of immunostaining blocks of 293α cells forced to express a FGFR3 IIIb or FGFR3 IIIc molecule, using a commercially available anti-FGFR2 antibody (ab58201).

FIG. 13D is a diagram showing the results of immunostaining blocks of 293α cells forced to express a FGFR4 molecule and blocks of 293α cells transfected with an empty vector, using a commercially available anti-FGFR2 antibody (ab58201).

FIG. 14A shows a nucleotide sequence encoding the heavy chain variable region of the rat anti-FGFR2 antibody FR2-2nd_#028 (SEQ ID NO: 2).

FIG. 14B shows the amino acid sequence of the heavy chain variable region of the rat anti-FGFR2 antibody FR2-2nd_#028 (SEQ ID NO: 3).

FIG. 14C shows a nucleotide sequence encoding the light chain variable region of the rat anti-FGFR2 antibody FR2-2nd_#028 (SEQ ID NO: 5).

FIG. 14D shows the amino acid sequence of the light chain variable region of the rat anti-FGFR2 antibody FR2-2nd_#028 (SEQ ID NO: 6).

FIG. 15A shows a nucleotide sequence encoding the heavy chain variable region of the rat anti-FGFR2 antibody FR2-2nd_#023 (SEQ ID NO: 7).

FIG. 15B shows the amino acid sequence of the heavy chain variable region of the rat anti-FGFR2 antibody FR2-2nd_#023 (SEQ ID NO: 8).

FIG. 15C shows a nucleotide sequence encoding the light chain variable region of the rat anti-FGFR2 antibody FR2-2nd_#023 (SEQ ID NO: 9).

FIG. 15D shows the amino acid sequence of the light chain variable region of the rat anti-FGFR2 antibody FR2-2nd_#023 (SEQ ID NO: 10).

FIG. 16 shows the nucleotide sequence of a DNA fragment comprising a nucleotide sequence encoding the amino acid sequence of a human κ chain secretory signal sequence and a human κ chain constant region (SEQ ID NO: 11).

FIG. 17A shows a nucleotide sequence comprising a nucleotide sequence (nucleotide positions 26 to 1411) encoding the heavy chain of the mouse chimeric anti-FGFR2 antibody FR2-2nd_#028 (SEQ ID NO: 14).

FIG. 17B shows the amino acid sequence of the heavy chain of the mouse chimeric anti-FGFR2 antibody FR2-2nd_#028 (SEQ ID NO: 15).

FIG. 17C shows a nucleotide sequence comprising a nucleotide sequence (nucleotide positions 26 to 724) encoding the light chain of the mouse chimeric anti-FGFR2 antibody FR2-2nd_#028 (SEQ ID NO: 18).

FIG. 17D shows the amino acid sequence of the light chain of the mouse chimeric anti-FGFR2 antibody FR2-2nd_#028 (SEQ ID NO: 19).

FIG. 18A shows a nucleotide sequence comprising a nucleotide sequence (nucleotide positions 26 to 1423) encoding the heavy chain of the mouse chimeric anti-FGFR2 antibody FR2-2nd_#023 (SEQ ID NO: 20).

FIG. 18B shows the amino acid sequence of the heavy chain of the mouse chimeric anti-FGFR2 antibody FR2-2nd_#023 (SEQ ID NO: 21).

FIG. 18C shows a nucleotide sequence comprising a nucleotide sequence (nucleotide positions 26 to 724) encoding the light chain of the mouse chimeric anti-FGFR2 antibody FR2-2nd_#023 (SEQ ID NO: 22).

FIG. 18D shows the amino acid sequence of the light chain of the mouse chimeric anti-FGFR2 antibody FR2-2nd_#023 (SEQ ID NO: 23).

FIG. 19 shows the amino acid sequences of CDRH1 to CDRH3 and CDRL1 to CDRL3 of the rat anti-human FGFR2 antibody FR2-2nd_#028 (SEQ ID NOs: 24 to 29).

FIG. 20 shows the amino acid sequences of CDRH1 to CDRH3 and CDRL1 to CDRL3 of the rat anti-human FGFR2 antibody FR2-2nd_#023 (SEQ ID NOs: 30 to 35).

DESCRIPTION OF EMBODIMENTS

1. Definitions

In the present invention, the term "gene" means a nucleotide comprising a nucleotide sequence encoding the amino acids of a protein, or its complementary strand. The term "gene" is meant to include, for example, a polynucleotide, an oligonucleotide, DNA, mRNA, cDNA, and cRNA as the nucleotide comprising a nucleotide sequence encoding the amino acids of a protein, or its complementary strand. Such a gene may be a single-stranded, double-stranded, or triple or more stranded nucleotide. The term "gene" is also meant to include an association of DNA and RNA strands, a mixture of ribonucleotides (RNAs) and deoxyribonucleotides (DNAs) on one nucleotide strand, and a double-stranded or triple or more stranded nucleotide comprising such a nucleotide strand. Examples of the "FGFR2 gene" of the present invention can include DNA, mRNA, cDNA, and cRNA comprising a nucleotide sequence encoding the amino acid sequence of the FGFR2 protein.

In the present invention, the term "nucleotide" has the same meaning as a "nucleic acid" and is also meant to include, for example, DNA, RNA, a probe, an oligonucleotide, a polynucleotide, and a primer. Such a nucleotide is a single-stranded, double-stranded, or triple or more stranded nucleotide. The term "nucleotide" is also meant to include an association of DNA and RNA strands, a mixture of ribonucleotides (RNAs) and deoxyribonucleotides (DNAs) on one nucleotide strand, and an associate of two strands or three or more strands comprising such a nucleotide strand.

In the present invention, the terms "polypeptide", "peptide", and "protein" have the same meaning.

In the present invention, the term "antigen" has the same meaning as "immunogen".

In the present invention, the term "cell" also includes, for example, various cells derived from individual animals, subcultured cells, primary cultured cells, cell lines, recombinant cells, and microbial cells.

In the present invention, antibodies recognizing FGFR2, FGFR2 IIIb, FGFR2 IIIc, FGFR3, FGFR4, and the like are also referred to as an "anti-FGFR2 antibody", an "anti-FGFR2 IIIb antibody", an "anti-FGFR2 IIIc antibody", an "anti-FGFR3 antibody", and an "anti-FGFR4 antibody", respectively. These antibodies include chimeric antibodies, humanized antibodies, human antibodies, and the like.

In the present invention, the term "functional fragment of the antibody" means an antibody fragment that exhibits at least a portion of the functions exhibited by the original antibody. Examples of the "functional fragment of the antibody" can include, but are not limited to, Fab, F(ab')2, scFv, Fab', and single chain immunoglobulin. Such a functional fragment of the antibody may be obtained by treating a full-length molecule of the antibody protein with an enzyme such as papain or pepsin, or may be a recombinant protein produced in an appropriate host cell using a recombinant gene.

In the present invention, the "site" to which an antibody binds, i.e., the "site" recognized by an antibody, means a partial peptide or partial conformation on an antigen bound or recognized by the antibody. In the present invention, such a site is also referred to as an epitope or an antibody binding site. Examples of the site on the FGFR2 protein bound or recognized by the anti-FGFR2 antibody of the present invention can include a partial peptide or partial conformation on the FGFR2 protein.

The heavy and light chains of an antibody molecule are known to each have three complementarity determining regions (CDRs). The complementarity determining regions are also called hypervariable domains. These regions are located in the variable regions of the antibody heavy and light chains. These sites have a particularly highly variable primary structure and are usually separated at three positions on the respective primary structures of heavy and light chain polypeptide strands. In the present invention, the complementarity determining regions of the antibody are referred to as CDRH1, CDRH2, and CDRH3 from the amino terminus of the heavy chain amino acid sequence for the complementarity determining regions of the heavy chain; and as CDRL1, CDRL2, and CDRL3 from the amino terminus of the light chain amino acid sequence for the complementarity determining regions of the light chain. These sites are proximal to each other on the three-dimensional structure and determine specificity for the antigen to be bound.

In the present invention, the term "antibody mutant" means a polypeptide that has an amino acid sequence derived from the amino acid sequence of the original antibody by the substitution, deletion, addition, and/or insertion (hereinafter, collectively referred to as a "mutation") of amino acid(s) and binds to the FGFR2 protein of the present invention. The number of mutated amino acids in such an antibody mutant is 1 to 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40, or 1 to 50. Such an antibody mutant is also encompassed by the "antibody" of the present invention.

In the present invention, the term "several" in "1 to several" refers to 3 to 10.

Examples of activities or properties exhibited by the antibody of the present invention can include biological activities or physicochemical properties and can specifically include various biological activities, binding activity against an antigen or an epitope, stability during production or storage, and thermal stability.

In the present invention, the phrase "hybridizing under stringent conditions" means hybridization under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or hybridization under conditions equivalent thereto. SSC means an aqueous solution of 150 mM NaCl-15 mM sodium citrate, and n×SSC means SSC with an n-fold concentration.

In the present invention, the term "cytotoxicity" refers to some pathological change brought about to cells and means not only direct trauma but any structural or functional damage to cells, including DNA cleavage, formation of base dimers, chromosomal break, damage to mitotic apparatus, and reduction in the activities of various enzymes.

In the present invention, the term "cytotoxic activity" means activity that causes the cytotoxicity mentioned above. In the present invention, the term "antibody dependent cellular cytotoxic activity", also called "ADCC activity", means the effect or activity of damaging target cells such as tumor cells by NK cells via antibodies.

In the present invention, the term "antibody dependent cell phagocytosis activity", also called "ADCP activity", means the effect or activity of englobing target cells such as tumor cells by monocyte or macrophage cells via antibodies. This activity is also referred to as "antibody dependent phagocytic effect or activity".

In the present invention, the term "complement dependent cytotoxic activity", also called "CDC activity", means the effect or activity of damaging target cells such as tumor cells by complement via antibodies.

In the present invention, the term "cancer" has the same meaning as "tumor".

In the present invention, the term "immunohistochemistry (IHC)" means a histological (histochemical) approach of detecting an antigen in a tissue preparation. The term immunohistochemistry is synonymous with an "immune antibody method" and has the same meaning as "immunostaining".

In the present invention, "denatured" FGFR means a FGFR molecule in a preparation fixed in formalin. The "denatured" FGFR also refers to a FGFR molecule in a preparation fixed in formalin, then treated with paraffin, and deparaffinized.

In the present invention, "non-denatured" FGFR means FGFR in a sample that is not fixed in formalin. The "non-denatured" FGFR also refers to a FGFR molecule in a preparation that is not fixed in formalin.

2. Antigenic Protein (2-1) Properties

FGFRs are receptor proteins that bind to fibroblast growth factors (FGFs). In the present invention, FGFRs are derived from vertebrates, preferably mammals, more preferably humans. Human FGFs and FGFRs are classified into 22 FGFs (FGF1 to FGF14 and FGF16 to FGF23) and 4 FGFRs (FGFR1 to FGFR4) having a tyrosine kinase domain, respectively. These FGFRs are each composed of an extracellular region comprising a ligand binding site composed of 2 or 3 immunoglobulin-like domains (IgD1 to IgD3), a single-pass transmembrane region, and an intracellular region comprising the tyrosine kinase domain. FGFR1, FGFR2, and FGFR3 each have two splicing variants called IIIb and IIIc. These isoforms differ in the sequence of approximately 50 amino acids in the latter half of IgD3 and exhibit distinctive tissue distribution and ligand specificity. FGFRs have the following activities: (1) binding to FGFs; (2) this binding dimerizes the FGFRs; (3) this dimerization phosphorylates the FGFRs at their particular tyrosine residues; (4) this phosphorylation promotes the recruitment of adaptor proteins such as FGFR substrate 2α (FRS2α); and (5) this transduces signals generated by FGF stimulation to cells or tissues expressing the FGFRs or activates signal transduction.

The FGFR2 protein according to the present invention has the following properties:

(i) Binding to FGF.

The FGFR2 IIIb protein typically binds to one or two or more FGFs selected from the group consisting of FGF1, FGF3, FGF7 (KGF), FGF10, FGF22, and FGF23. The FGFR2 IIIb protein may bind to other FGFs and may not bind to mutated forms of the FGFs included in the above group.

The FGFR2 IIIc protein typically binds to one or two or more FGFs selected from the group consisting of FGF1, FGF2, FGF4, FGF6, FGF9, FGF17, FGF18, FGF21, and FGF23. The FGFR2 IIIc protein may bind to other FGFs and may not bind to mutated forms of the FGFs included in the above group.

(ii) Transducing signals generated by FGF stimulation into FGFR2-expressing cells or tissues Examples of the transduction of signals generated by FGF stimulation can include, but are not particularly limited to, FGFR2 autophosphorylation, recruitment of FGFR substrates and promotion thereof, and activation of signaling pathways such as MAPK, PI3K, Akt, and extracellular signal-regulated kinase (ERK) pathways via these events. Examples of the FGFR substrates can include FGFR substrate 2α (FRS2α).

Testing methods for evaluating the activation of this signal transduction and the inhibition thereof are not particularly limited and can be arbitrarily selected from methods known in the art. Examples thereof can include evaluation systems for ERK signal transduction, and Elk1 luciferase reporter assay described later.

(iii) The FGFR2 IIIb protein according to the present invention comprises an amino acid sequence described in any one of the following (a) to (d) (hereinafter, referred to as an "FGFR2 IIIb amino acid sequence"), consists of an amino acid sequence comprising the FGFR2 IIIb amino acid sequence, or consists of the FGFR2 IIIb amino acid sequence:

(a) the amino acid sequence represented by the amino acid sequence of NP_075259 published on the database;
(b) an amino acid sequence that exhibits 80% or higher, 82% or higher, 84% or higher, 86% or higher, 88% or higher, 90% or higher, 92% or higher, 94% or higher, 96% or higher, 98% or higher, or 99% or higher, sequence identity to the amino acid sequence represented by the amino acid sequence of NP_075259 and is carried by a polypeptide having FGF binding activity;
(c) an amino acid sequence that is derived from the amino acid sequence represented by the amino acid sequence of NP_075259 by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and is carried by a polypeptide having FGF binding activity; and
(d) an amino acid sequence that is encoded by the nucleotide sequence of a nucleotide hybridizing under stringent conditions to a nucleotide having a nucleotide sequence complementary to a nucleotide sequence encoding the amino acid sequence represented by the amino acid sequence of NP_075259 and is carried by a polypeptide having FGF binding activity.

The polypeptide described in any one of (b) to (d) may have FGFR2 activities other than FGF binding activity.

The FGFR2 IIIc protein according to the present invention comprises an amino acid sequence described in any one of the following (a) to (d) (hereinafter, referred to as an "FGFR2 IIIc amino acid sequence"), consists of an amino acid sequence comprising the FGFR2 IIIc amino acid sequence, or consists of the FGFR2 IIIc amino acid sequence:

(a) an amino acid sequence represented by NP_000132 published on the database;
(b) an amino acid sequence that exhibits 80% or higher, 82% or higher, 84% or higher, 86% or higher, 88% or higher, 90% or higher, 92% or higher, 94% or higher, 96% or higher, 98% or higher, or 99% or higher, sequence identity to the amino acid sequence represented by NP_000132 and is carried by a polypeptide having FGF binding activity;
(c) an amino acid sequence that is derived from the amino acid sequence represented by NP_000132 by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and is carried by a polypeptide having FGF binding activity; and
(d) an amino acid sequence that is encoded by the nucleotide sequence of a nucleotide hybridizing under stringent conditions to a nucleotide having a nucleotide sequence complementary to a nucleotide sequence encoding the amino acid sequence represented by NP_000132 and is carried by a polypeptide having FGF binding activity.

The polypeptide described in any one of (b) to (d) may have FGFR2 activities other than FGF binding activity.

(iv) The FGFR2 protein of the present invention can be obtained from FGFR2-expressing cells, tissues, or cancer tissues, cells derived from the tissues, cultures of the cells, and the like, of a vertebrate, preferably of a mammal, more preferably of a rodent such as a mouse or a rat and a human, even more preferably of a mouse, rat and a human.

Examples of normal tissues highly expressing FGFR2 can include the brain, the large intestine, thyroid glands, the uterus, the gallbladder, and the skin. Gene amplification is found in some cancers highly expressing FGFR2, such as stomach cancer and breast cancer, while overexpression is found in some cancers highly expressing FGFR2, such as pancreatic cancer and ovarian cancer. Examples of cultured cell lines highly expressing FGFR2 IIIb can include stomach cancer cell lines and breast cancer cell lines. Examples of cultured cell lines highly expressing FGFR2 IIIc can include colorectal (cecal) cancer cell lines. Examples of cancer tissues expressing FGFR2 IIIc can include tissues with uterine cervix cancer and non-small cell lung cancer. Of these cancers, uterine cervix cancer highly expresses FGFR2 IIIc.

The FGFR2 protein of the present invention may be a native (non-recombinant) or recombinant protein. The FGFR2 protein is also meant to include fusion products with another peptide or protein such as a carrier or a tag. The FGFR2 protein is further meant to include forms provided with chemical modification including the addition of a polymer such as PEG and/or with biological modification including sugar chain modification. Moreover, the FGFR2 protein of the present invention is meant to include an FGFR2 protein fragment. An FGFR2 protein fragment possessing the properties described above in (i) and/or (ii) is referred to as a functional fragment of the FGFR2 protein.

(2-2) Antigen Gene

The FGFR2 IIIb gene according to the present invention comprises a nucleotide sequence described in any one of the following (a) to (c) (hereinafter, referred to as an "FGFR2 IIIb gene sequence"), consists of a nucleotide sequence comprising the FGFR2 gene sequence, or consists of the FGFR2 gene sequence:

(a) a nucleotide sequence encoding the amino acid sequence represented by NP_075259;
(b) a nucleotide sequence that hybridizes under stringent conditions to a nucleotide consisting of a nucleotide sequence complementary to the nucleotide sequence encoding the amino acid sequence represented by NP_075259 and encodes the amino acid sequence of a polypeptide having FGF binding activity; and
(c) a nucleotide sequence that encodes an amino acid sequence derived from the amino acid sequence represented by NP_075259 by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and encodes the amino acid sequence of a polypeptide having FGF binding activity.

The polypeptide having the amino acid sequence encoded by the nucleotide sequence (b) or (c) may have FGFR2 activities other than FGF binding activity.

The FGFR2 IIIc gene according to the present invention comprises a nucleotide sequence described in any one of the following (a) to (c) (hereinafter, referred to as an "FGFR2 IIIc gene sequence"), consists of a nucleotide sequence comprising the FGFR2 gene sequence, or consists of the FGFR2 gene sequence:

(a) a nucleotide sequence encoding the amino acid sequence represented by NP_000132;
(b) a nucleotide sequence that hybridizes under stringent conditions to a nucleotide consisting of a nucleotide sequence complementary to the nucleotide sequence encoding the amino acid sequence represented by NP_000132 and encodes the amino acid sequence of a polypeptide having FGF binding activity; and
(c) a nucleotide sequence that encodes an amino acid sequence derived from the amino acid sequence represented by NP_000132 by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and encodes the amino acid sequence of a polypeptide having FGF binding activity.

The polypeptide having the amino acid sequence encoded by the nucleotide sequence (b) or (c) may have FGFR2 activities other than FGF binding activity.

The expression and expression level of the FGFR2 gene may be assayed with either an FGFR2 gene transcript or the FGFR2 protein as an index. The former index can be determined by RT-PCR, Northern blot hybridization, or the like, while the latter index can be determined by, for example, immunoassay such as enzyme-linked immunosorbent assay (hereinafter, referred to as "ELISA"), Western blotting, or immunohistological staining.

(2-3) Preparation of an Antigenic Protein

The FGFR2 protein of the present invention can be prepared by purification or isolation from animal tissues (including body fluids), cells derived from the tissues, or cultures of the cells, gene recombination, in vitro translation, chemical synthesis, etc.

(2-3-1) Purification or Isolation of Non-Recombinant FGFR2

Non-recombinant FGFR2 protein can be purified or isolated from FGFR2-expressing cells, normal tissues, or cancer tissues, or cells derived therefrom. Examples of FGFR2-expressing normal tissues, cancer tissues, or cancer cells can include those described in (iv) of paragraph (2-1), though the origin of the non-recombinant FGFR2 protein is not limited thereto.

Purification or isolation from such tissues, cells, cell cultures, or the like, can be performed by any combination of approaches well known by those skilled in the art, such as fractionation and chromatography. Such approaches include, but are not limited to, salting out, gel filtration, ion-exchange chromatography, affinity chromatography, hydrophobic chromatography, normal-phase or reverse-phase chromatography, and the like. A column for affinity chromatography can be prepared by packing the column with an affinity gel cross-linked with an anti-FGFR2 monoclonal antibody. A crude or partially purified fraction containing the FGFR2 protein is applied to this column. Subsequently, non-specifically adsorbed substances are removed with sterilized phosphate-buffered saline (PBS), and a buffer solution for elution can then be applied thereto to thereby selectively recover the FGFR2 protein. The solution containing the FGFR2 protein can be subjected to gel filtration or to buffer replacement and/or concentration using a concentrator such as Centriprep.

(2-3-2) Preparation of Recombinant FGFR2 Protein

The FGFR2 protein of the present invention can also be prepared in a recombinant form. Specifically, host cells are transfected with a gene encoding the amino acid sequence of the FGFR2 protein or an FGFR2 protein fragment, and the FGFR2 protein can be recovered from cultures of the cells. For example, the FGFR2 gene or its fragment is inserted into an expression vector. Subsequently, prokaryotic or eukaryotic host cells are transfected with the resulting recombinant vector, and the obtained recombinant cells can be incubated to thereby express the FGFR2 protein. An expression pattern known in the art, such as secretion expression, intracellular expression of soluble forms, or expression in inclusion body forms can be used. Also, the FGFR2 protein can be expressed not only as a molecule having the same amino terminus (N terminus) and/or carboxy terminus (C terminus) as native ones, but also as a fusion protein with a secretory signal, an intracellular localization signal, a tag for affinity purification, or a partner peptide. The FGFR2 protein can be purified or isolated from such recombinant cell cultures by an appropriate combination of methods such as fractionation and chromatography described in (2-3-1).

The FGFR2 gene or its fragment can be prepared by a method well known by those skilled in the art.

Examples thereof can include: polymerase chain reaction (hereinafter, referred to as "PCR"; Saiki, R. K., et al., Science (1988) 239, p. 487-489) with a cDNA library prepared from FGFR2-expressing cells, tissues, or the like as a template using one set of primers capable of specifically amplifying the sequence; reverse transcription PCR (hereinafter, referred to as "RT-PCR") with an mRNA fraction prepared from FGFR2-expressing cells, tissues, or the like as a template using a primer capable of reverse-transcribing the sequence and one set of primers capable of specifically amplifying the sequence; expression cloning using immunoassay; and cDNA cloning using the partial amino acid sequence of purified FGFR2 protein.

(2-3-3) In Vitro Translation

The FGFR2 protein of the present invention can also be prepared by in vitro translation. Such a translation method is not particularly limited as long as the method employs a cell-free translation system involving enzymes necessary for transcription and translation, substrates, and energy substances. Examples thereof can include a method using Rapid Translation System (RTS) manufactured by Roche Diagnostics K.K.

(2-3-4) Chemical Synthesis

The FGFR2 protein of the present invention can also be prepared by chemical synthesis. Examples of the chemical synthesis method can include solid-phase peptide synthesis methods such as Fmoc and Boc synthesis methods.

3. Antibody (3-1) Antibody Classification

The antibodies of the present invention may be either monoclonal or polyclonal antibodies. Examples of the monoclonal antibody of the present invention can include non-human animal-derived antibodies (non-human animal antibodies), human-derived antibodies (human antibodies), chimeric antibodies, and humanized antibodies.

Examples of a non-human animal antibody can include antibodies derived from vertebrates such as mammals and birds. Examples of a mammal-derived antibody can include rodent-derived antibodies such as mouse antibodies and rat antibodies. Examples of a bird-derived antibody can include chicken antibodies. Examples of an anti-human FGFR2 rat monoclonal antibody can include FR2-2nd_#023, and FR2-2nd_#028.

Examples of a chimeric antibody can include, but are not limited to, an antibody comprising non-human animal antibody-derived variable regions bound with human antibody (human immunoglobulin) constant regions. Examples thereof can include: mouse chimeric FR2-2nd_#023 (a nucleotide sequence encoding the amino acid sequence of the heavy chain is described in nucleotide positions 26 to 1423 of SEQ ID NO: 20 or FIG. 18A; the amino acid sequence of the heavy chain is described in SEQ ID NO: 21 or FIG. 18B; a nucleotide sequence encoding the amino acid sequence of the light chain is described in nucleotide positions 26 to 724 of SEQ ID NO: 22 or FIG. 18C; and the amino acid sequence of the light chain is described in SEQ ID NO: 23 or FIG. 18D) derived from rat FR2-2nd_#023 (a nucleotide sequence encoding the amino acid sequence of the heavy chain variable region is described in SEQ ID NO: 7 or FIG. 15A; the amino acid sequence of the heavy chain variable region is described in SEQ ID NO: 8 or FIG. 15B; a nucleotide sequence encoding the amino acid sequence of the light chain variable region is described in SEQ ID NO: 9 or FIG. 15C; and the amino acid sequence of the light chain variable region is described in SEQ ID NO: 10 or FIG. 15D) by the replacement of its constant regions with mouse antibody constant regions; and mouse chimeric FR2-2nd_#028 (a nucleotide sequence encoding the amino acid sequence of the heavy chain is described in nucleotide positions 26 to 1411 of SEQ ID NO: 14 or FIG. 17A; the amino acid sequence of the heavy chain is described in SEQ ID NO: 15 or FIG. 17B; a nucleotide sequence encoding the amino acid sequence of the light chain is described in nucleotide positions 26 to 724 of SEQ ID NO: 18 or FIG. 17C; and the amino acid sequence of the light chain is described in SEQ ID NO: 19 or FIG. 17D) derived from rat FR2-2nd_#028 (a nucleotide sequence encoding the amino acid sequence of the heavy chain variable region is described in SEQ ID NO: 2 or FIG. 14A; the amino acid sequence of the heavy chain variable region is described in SEQ ID NO: 3 or FIG. 14B; a nucleotide sequence encoding the amino acid sequence of the light chain variable region is described in SEQ ID NO: 5 or FIG. 14C; and the amino acid sequence of the light chain variable region is described in SEQ ID NO: 6 or FIG. 14D) by the replacement of its constant regions with mouse antibody constant regions.

Examples of a humanized antibody can include, but are not limited to, a human antibody (human immunoglobulin variable regions) grafted with CDRs in the variable regions of a non-human animal antibody, a human antibody grafted with the CDRs as well as with partial sequences of framework regions of a non-human animal antibody, and an antibody having human antibody amino acid(s) substituted for one or two or more non-human animal antibody-derived amino acid(s) in any of these humanized antibodies.

A human antibody is not particularly limited as long as the antibody recognizes the antigen of the present invention. Examples thereof can include a human antibody binding to the same site, as in the case of an antibody having the CDRs of the antibody of the present invention, and a human antibody binding to the same site on FGFR2 as in the case of the FR2-2nd_#023 antibody or the chimeric antibody thereof or FR2-2nd_#028 or the chimeric antibody thereof mentioned above.

The antibody according to the present invention may be comprised of portions derived from a plurality of different antibodies as long as the antibody has FGFR2 binding activity. Examples of such an antibody can include an antibody comprising heavy and/or light chains exchanged among a plurality of different antibodies, an antibody comprising full-length heavy and/or light chains exchanged among a plurality of different antibodies, an antibody comprising variable or constant regions exchanged among a plurality of different antibodies, and an antibody comprising all or some CDRs exchanged among a plurality of different antibodies. The heavy and light chain variable regions of the chimeric antibody may be derived from different antibodies of the present invention. CDRH1 to CDRH3 and CDRL1 to CDRL3 in the heavy and light chain variable regions of the humanized antibody may be derived from two or more different antibodies of the present invention. CDRH1 to CDRH3 and CDRL1 to CDRL3 in the heavy and light chain variable regions of the human antibody may be a combination of CDRs carried by two or more different antibodies of the present invention.

Examples of the isotype of the monoclonal antibody of the present invention can include, but are not particularly limited to, IgG such as IgG1, IgG2, IgG3, and IgG4, IgM, IgA such as IgA1 and IgA2, IgD, and IgE and can preferably include IgG and IgM. The isotype and subclass of the monoclonal antibody can be determined by, for example, an Ouchterlony test, ELISA, or radio immunoassay (hereinafter, referred to as "RIA"). A commercially available kit for identification (e.g., Mouse Typer Kit; Bio-Rad Laboratories, Inc., and RAT MONOCLONAL ANTIBODY ISOTYPING TEST KIT: AbD Serotec) may be used.

(3-2) Antibody Binding Specificity

The antibody of the present invention recognizes the FGFR2 protein. In other words, the antibody of the present invention binds to the FGFR2 protein. Such an antibody is referred to as an "anti-FGFR2 antibody". Preferably, the antibody of the present invention specifically recognizes the FGFR2 protein. In other words, preferably, the antibody of the present invention specifically binds to the FGFR2 protein. More preferably, the antibody of the present invention specifically binds to the FGFR2 IIIb protein and/or the FGFR2 IIIc protein. Even more preferably, the antibody of the present invention specifically binds to the immunoglobulin-like domain (hereinafter, referred to as "Ig-like domain") of the FGFR2 IIIb protein and/or the FGFR2 IIIc protein. Examples of such an Ig-like domain can include Ig-like domain 2 and Ig-like domain 3.

According to an aspect, preferably, the antibody specifically binds to the human FGFR2 IIIb protein and the human FGFR2 IIIc protein.

According to another aspect, preferably, the antibody specifically binds to the human FGFR2 IIIc protein, but does not bind to the human FGFR2 IIIb protein.

According to an aspect, preferably, the antibody specifically binds to both non-denatured human FGFR2 and denatured FGFR2 in a preparation fixed in formalin. More preferably, the antibody specifically binds to none of the following: non-denatured human FGFR1 (IIIb and IIIc proteins), FGFR3 (IIIb and IIIc proteins), and FGFR4, or denatured human FGFR1 (IIIb and IIIc proteins), FGFR3 (IIIb and IIIc proteins), and FGFR4 in a preparation fixed in formalin. For example, the binding specificity for a non-denatured molecule of the FGFR family can be evaluated by a method described in Example 3, and the binding specificity for a denatured molecule of the FGFR family can be evaluated by a method described in Example 4.

Thus, even more preferred examples of the antibody of the present invention can include, but are not limited to:
(A) an antibody that specifically binds to non-denatured and denatured human FGFR2 IIIc and human FGFR2 IIIb, but specifically binds to none of the following: non-denatured and denatured human FGFR1, human FGFR3, and human FGFR4; and
(B) an antibody that specifically binds to non-denatured and denatured human FGFR2 IIIc, but specifically binds to neither non-denatured nor denatured human FGFR2 IIIb and specifically binds to none of the following: non-denatured and denatured human FGFR1, human FGFR3, and human FGFR4.

In the present invention, the term "specific recognition", i.e., "specific binding", means binding which is not non-specific adsorption. Examples of criteria for determination of whether binding is specific or not can include a dissociation constant (hereinafter, referred to as "KD"). Preferably, the antibody of the present invention has a KD value of $1\times10^{-3}$ M or lower, $5\times10^{-6}$ M or lower, $2\times10^{-6}$ M or lower, or $1\times10^{-6}$ M or lower, more preferably $5\times10^{-7}$ M or lower, $2\times10^{-7}$ M or lower, or $1\times10^{-7}$ M or lower, even more preferably $5\times10^{-8}$ M or lower, $2\times10^{-8}$ M or lower, or $1\times10^{-8}$ M or lower, further more preferably $5\times10^{-9}$ M or lower, $2\times10^{-9}$ M or lower, or $1\times10^{-9}$ M or lower, most preferably $5\times10^{-10}$ M or lower, $2\times10^{-10}$ M or lower, or $1\times10^{-10}$ M or lower for the FGFR2 protein.

In the present invention, the term "selective" has the same meaning as "specific".

In the present invention, the binding of the antibody to the antigen can be assayed or determined by ELISA, RIA, surface plasmon resonance (hereinafter, referred to as "SPR") analysis, or the like. Examples of equipment used in the SPR analysis can include BIAcore™ (manufactured by GE Healthcare Bio-Sciences Corp.), ProteOn™ (manufactured by Bio-Rad Laboratories, Inc.), SPR-Navi™ (manufactured by BioNavis Oy Ltd.), Spreeta™ (manufactured by Texas Instruments Inc.), SPRi-Plex II™ (manufactured by Horiba, Ltd.), and Autolab SPR™ (manufactured by Metrohm Japan Ltd.). The binding of the antibody to the antigen expressed on cell surface can be assayed by flow cytometry, Cell-ELISA, or the like.

(3-3) Monoclonal Antibody

The present invention provides a monoclonal antibody. The monoclonal antibody includes, for example, non-human animal-derived monoclonal antibodies such as rat, mouse, rabbit, chicken, and fish antibodies, chimeric antibodies, humanized antibodies, human antibodies, functional fragments thereof, and modified forms of these antibodies or functional fragments. Of them, examples of the rat monoclonal antibody can include the FR2-2nd_#023, and FR2-2nd_#028.

FR2-2nd_#023 is an anti-human FGFR2 rat monoclonal antibody obtained by the method described in Example 1. The nucleotide sequence of the heavy chain variable region is described in SEQ ID NO: 7 (FIG. 15A), and its amino acid sequence is described in SEQ ID NO: 8 (FIG. 15B). The nucleotide sequence of the light chain variable region is described in SEQ ID NO: 9 (FIG. 15C), and its amino acid sequence is described in SEQ ID NO: 10 (FIG. 15D). The amino acid sequence of CDRH1 is described in SEQ ID NO: 30 (FIG. 20). The amino acid sequence of CDRH2 thereof is described in SEQ ID NO: 31 (FIG. 20). The amino acid sequence of CDRH3 thereof is described in SEQ ID NO: 32 (FIG. 20). The amino acid sequence of CDRL1 thereof is described in SEQ ID NO: 33 (FIG. 20). The amino acid sequence of CDRL2 thereof is described in SEQ ID NO: 34 (FIG. 20). The amino acid sequence of CDRL3 thereof is described in SEQ ID NO: 35 (FIG. 20).

FR2-2nd_#028 is an anti-human FGFR2 rat monoclonal antibody obtained by the method described in Example 1. The nucleotide sequence of the heavy chain variable region is described in SEQ ID NO: 2 (FIG. 14A), and its amino acid sequence is described in SEQ ID NO: 3 (FIG. 14B). The nucleotide sequence of the light chain variable region is described in SEQ ID NO: 5 (FIG. 14C), and its amino acid sequence is described in SEQ ID NO: 6 (FIG. 14D). The amino acid sequence of CDRH1 is described in SEQ ID NO: 24 (FIG. 19). The amino acid sequence of CDRH2 thereof is described in SEQ ID NO: 25 (FIG. 19). The amino acid sequence of CDRH3 thereof is described in SEQ ID NO: 26 (FIG. 19). The amino acid sequence of CDRL1 thereof is described in SEQ ID NO: 27 (FIG. 19). The amino acid sequence of CDRL2 thereof is described in SEQ ID NO: 28 (FIG. 19). The amino acid sequence of CDRL3 thereof is described in SEQ ID NO: 29 (FIG. 19).

An antibody mutant of the present invention preferably exhibits, for example, reduced sensitivity to protein degradation or oxidation, an improved biological activity, an improved ability to bind to the antigen, or physicochemical or functional properties imparted thereto. Examples of such an antibody mutant can include an antibody having an amino acid sequence derived from the amino acid sequence of the original antibody by conservative amino acid substitution. The conservative amino acid substitution is a substitution that occurs in an amino acid group related to amino acid side chains.

Preferred amino acid groups are as follows: an acidic group including aspartic acid and glutamic acid; a basic group including lysine, arginine, and histidine; a nonpolar group including alanine, valine, leucine, isoleucine, proline, phenylalanine, methionine, and tryptophan; and an uncharged polar family including glycine, asparagine, glutamine, cysteine, serine, threonine, and tyrosine. Other preferred amino acid groups are as follows: an aliphatic hydroxy group including serine and threonine; an amide-containing group including asparagine and glutamine; an aliphatic group including alanine, valine, leucine, and isoleucine; and an aromatic group including phenylalanine, tryptophan, and tyrosine. Such amino acid substitution in the antibody mutant is preferably performed without reducing the antigen binding activity of the original antibody.

Aspartic acid contained in a protein is easily converted to isoaspartic acid by isomerization when an amino acid linked thereto on the C terminal side has a small side chain. On the other hand, asparagine is easily converted to aspartic acid by deamidation and may be further converted to isoaspartic acid by isomerization. The progression of such isomerization or deamidation may influence the stability of the protein. Accordingly, aspartic acid or asparagine in the protein or, for example, an amino acid adjacent thereto, can be substituted by a different amino acid in order to circumvent such isomerization or deamidation. Preferably, an antibody mutant having such amino acid substitution maintains the antigen binding activity of the original antibody.

The present invention also encompasses, for example: an antibody mutant having an amino acid sequence derived from the amino acid sequence of antibodies of the present invention by conservative amino acid substitution; and a mouse antibody, a rat antibody, a chimeric antibody, a humanized antibody, or a human antibody comprising a CDR having an amino acid sequence in which a conservative amino acid mutation occurs in the amino acid sequence of any of CDRH1 to CDRH3 and CDRL1 to CDRL3 derived from antibodies of the present invention.

A mutant of the antibody of the present invention encompasses a human FGFR2-binding antibody mutant comprising CDRH1 to CDRH3 and CDRL1 to CDRL3 having amino acid sequences derived from the amino acid sequences of any one or two or more of CDRH1 to CDRH3 and CDRL1 to CDRL3 derived from antibodies of the present invention by the substitution of 1 to several, preferably 1 to 3, more preferably 1 or 2, most preferably 1 amino acid(s) by different amino acid(s).

An antibody mutant also includes an antibody having CDRH1 to CDRH3 and CDRL1 to CDRL3 derived from a plurality of antibodies. Examples of such a mutant can include an antibody mutant comprising CDRH3 derived from a certain antibody and CDRH1, CDRH2, and CDRL1 to CDRL3 derived from another antibody.

The term "antibody" according to the present invention also encompasses these antibody mutants.

The constant regions of the antibody of the present invention are not particularly limited. Preferably, constant regions derived from a human antibody are used in the antibody of the present invention for the treatment or prevention of a disease in a human. Examples of the heavy chain constant region of the human antibody can include Cγ1, Cγ2, Cγ3, Cγ4, Cμ, Cδ, Cα1, Cα2, and Cε. Examples of the light chain constant region of the human antibody can include Cκ and Cλ.

(3-4) Functional Fragments of the Antibody

According to one aspect, the present invention provides a functional fragment of the anti-FGFR2 antibody of the present invention. The functional fragment of the antibody means a fragment that maintains at least a portion of the functions of the antibody. Examples of such functions of the antibody can generally include antigen binding activity.

The functional fragment of the antibody is not particularly limited as long as the fragment of the antibody maintains at least a portion of the activities of the antibody. Examples thereof can include, but are not limited to, Fab, F(ab')2, Fv, single chain Fv (scFv) comprising heavy and light chain Fvs linked via an appropriate linker, diabodies, linear antibodies, multispecific antibodies formed from antibody fragments, and Fab', which is a monovalent fragment of antibody variable regions obtained by the treatment of F(ab')2 under reducing conditions. The functional fragment of the antibody of the present invention is also meant to include a molecule comprising the fragment of the antibody of the present invention as well as other portions, such as scFv retaining a linker portion.

A molecule that is derived from the antibody protein by the deletion of 1 to several or more amino acid(s) at its amino terminus and/or carboxy terminus and maintains at least a portion of the functions of the antibody is also encompassed in the meaning of the functional fragment of the antibody. For example, the heavy chain of an antibody produced by cultured mammalian cells is known to lack a lysine residue at the carboxy terminus (Journal of Chromatography A, 705: 129-134 (1995)). Also, the heavy chain of such an antibody is known to lack two amino acid residues (glycine and lysine) at the carboxy terminus and instead have an amidated proline residue at the carboxy terminus (Analytical Biochemistry, 360: 75-83 (2007)). The deletion and the modification in these heavy chain sequences, however, do not influence the ability of the antibody to bind to the antigen or its effector functions (complement activation, antibody dependent cytotoxic effects, etc.). Such a modified form of the functional fragment of the antibody is also encompassed by the antibody of the present invention or the functional fragment thereof, or a modified form (described later) of the antibody or functional fragment.

The antibody of the present invention or the functional fragment thereof may be a multispecific antibody having specificity for at least 2 types of different antigens. The multispecific antibody is not limited to a bispecific antibody, which binds to 2 types of different antigens, and an antibody having specificity for 3 or more types of different antigens is also encompassed in the meaning of the "multispecific antibody" of the present invention.

The multispecific antibody of the present invention may be a full-length antibody or a functional fragment thereof (e.g., bispecific F(ab')2 antibody). The bispecific antibody can also be prepared by linking the heavy and light chains (HL pairs) of two types of antibodies. Alternatively, the bispecific antibody may be obtained by fusing two or more types of monoclonal antibody-producing hybridomas to prepare bispecific antibody-producing fusion cells (Millstein et al., Nature (1983) 305, p. 537-539). The multispecific antibody can also be prepared in the same way as above.

According to one aspect, the antibody of the present invention is a single chain antibody (single chain Fv; hereinafter, referred to as "scFv"). The scFv is obtained by linking the heavy and light chain V regions of the antibody via a polypeptide linker (Pluckthun, The Pharmacology of Monoclonal Antibodies, 113, Rosenburg and Moore, ed., Springer Verlag, New York, p. 269-315 (1994); and Nature Biotechnology (2005), 23, p. 1126-1136). Also, bi-scFv comprising two scFvs linked via a polypeptide linker can be used as a bispecific antibody. Alternatively, multi-scFv comprising three or more scFvs may be used as a multispecific antibody.

The present invention includes a single chain immunoglobulin comprising full-length heavy and light chain sequences of the antibody linked via an appropriate linker (Lee, H-S, et al., Molecular Immunology (1999), 36, p. 61-71; and Shirrmann, T. et al., mAbs (2010), 2 (1) p. 1-4). Such a single chain immunoglobulin can be dimerized to thereby maintain a structure and activities similar to those of the antibody, which is originally a tetramer. Also, the antibody of the present invention may be an antibody that has a single heavy chain variable region and has no light chain region. Such an antibody, called a single domain antibody (sdAb) or a nanobody, has been reported to maintain the ability to bind to an antigen (Muyldemans S. et al., Protein Eng. (1994), 7 (9), 1129-35; and Hamers-Casterman C. et al., Nature (1993), 363 (6428), 446-8). These antibodies are also encompassed in the meaning of the functional fragment of the antibody according to the present invention.

The present invention also encompasses an antibody that comprises a heavy or light chain comprising an amino acid sequence having 80% or higher, 82% or higher, 84% or higher, 86% or higher, 88% or higher, 90% or higher, 92% or higher, 94% or higher, 96% or higher, 98% or higher, or 99% or higher identity to the amino acid sequence of the heavy or light chain, or heavy or light chain variable region of the present invention and binds to hFGFR2, or a functional fragment thereof. Such sequence identity is preferably 94% or higher, more preferably 96% or higher, even more preferably 98% or higher, most preferably 99% or higher.

The identity or homology between two types of amino acid sequences can be determined using the default parameter of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm is also available, for example, by Internet access at http://blast.ncbi.nlm.nih.gov/.

The present invention also encompasses an antibody that comprises a heavy or light chain comprising an amino acid sequence derived from the amino acid sequence of the heavy or light chain or the heavy or light chain variable region of the antibody of the present invention by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and binds to hFGFR2, or a functional fragment thereof. Such an amino acid mutation is preferably substitution. The number of mutated amino acids is preferably 1 to 5, more preferably 1 to 4, even more preferably 1 to 3, further more preferably 1 or 2, most preferably 1.

The present invention also encompasses an antibody that comprises a heavy or light chain comprising an amino acid sequence encoded by the nucleotide sequence of nucleotide hybridizing under stringent conditions to a nucleotide having a nucleotide sequence complementary to a nucleotide sequence encoding the amino acid sequence of the heavy or light chain or the heavy or light chain variable region of the antibody of the present invention and binds to hFGFR2, or a functional fragment thereof.

(3-5) Antibody Binding to the Epitope

An "antibody binding to the same site" as in the case of the antibody provided by the present invention is also included in the antibody of the present invention. The "antibody binding to the same site" as in the case of a certain antibody, means another antibody that binds to a site on an antigen molecule recognized by the antibody. If a second antibody binds to a partial peptide or a partial three-dimensional structure on an antigen molecule bound by a first antibody, the first and second antibodies are considered to bind to the same site. Alternatively, the first and second antibodies are considered to bind to the same site by confirming that the second antibody competes with the first antibody for binding to the antigen, i.e., the second antibody interferes with the binding of the first antibody to the antigen, even if the peptide sequence or three-dimensional structure of the specific binding site is not determined. When the first and second antibodies bind to the same site and the first antibody has an effect characteristic of one aspect of the antibody of the present invention, such as an antitumor activity, the second antibody also has an exceedingly high probability of having the same activity as the first. Thus, if a second anti-FGFR2 antibody binds to a site bound by a first anti-FGFR2 antibody, the first and second antibodies are considered to bind to the same site on the FGFR2 protein. Alternatively, the first and second anti-FGFR2 antibodies are considered to bind to the same site on the FGFR2 protein by confirming that the second anti-FGFR2 antibody competes with the first anti-FGFR2 antibody for binding to the FGFR2 protein.

The present invention also encompasses an antibody binding to a site on the FGFR2 protein recognized by the monoclonal antibody of the present invention.

The antibody binding site can be determined by a method well known by those skilled in the art, such as immunoassay. For example, a series of peptides are prepared by appropriately sequentially cleaving the amino acid sequence of the antigen from its C terminus or N terminus, and the reactivity of the antibody thereto is studied to roughly determine a recognition site. Then, shorter peptides are synthesized, and the reactivity of the antibody to these peptides can be studied to thereby determine the binding site. The antigen fragment peptides can be prepared using a technique such as gene recombination or peptide synthesis.

When the antibody binds to or recognizes the partial conformation of the antigen, the binding site for the antibody can be determined by identifying amino acid residues on the antigen adjacent to the antibody using X-ray structural analysis. For example, the antibody or its fragment and the antigen or its fragment can be bound to each other and crystallized, followed by structural analysis to identify each amino acid residue on the antigen having an interaction distance with the antibody. The interaction distance is 8 angstroms or shorter, preferably 6 angstroms or shorter, more preferably 4 angstroms or shorter. One or more such amino acid residues having an interaction distance with the antibody can constitute a site (epitope) on the antigen to which the antibody binds. Two or more such amino acid residues may not be adjacent to each other on the primary sequence.

(3-6) Modified Form of the Antibody

The present invention provides a modified form of the antibody or functional fragment thereof. The modified form of the antibody of the present invention or the functional fragment thereof means an antibody of the present invention or a functional fragment thereof provided with chemical or biological modification. The chemically modified form includes, for example, a form having an amino acid skeleton conjugated with a chemical moiety, and a form having a chemically modified N-linked or O-linked carbohydrate chain. A biologically modified form includes, for example, a form that has undergone post-translational modification (e.g., N-linked or O-linked glycosylation, N-terminal or C-terminal processing, deamidation, isomerization of aspartic acid, or oxidation of methionine), and a form containing a methionine residue added to the N-terminus by expression using prokaryotic host cells. Such a modified form is also meant to include a form labeled to permit detection or isolation of the antibody or the antigen of the present invention, for example, an enzyme-labeled form, a fluorescently labeled form, or an affinity-labeled form. Such a modified form of the antibody of the present invention or the functional fragment thereof is useful for improvement of the stability or blood retention of the original antibody of the present invention or the original functional fragment thereof, reduction in antigenicity, detection or isolation of the antibody or the antigen, etc.

Examples of a chemical moiety contained in the chemically modified form can include water-soluble polymers such as polyethylene glycol, ethylene glycol/propylene glycol copolymers, carboxymethylcellulose, dextran, and polyvinyl alcohol.

Examples of a biologically modified form can include a form modified by enzymatic treatment, cell treatment, or the like, a form fused with another peptide, such as a tag, added by gene recombination, and a form prepared from host cells expressing an endogenous or exogenous sugar chain-modifying enzyme.

Such a modification may be made at an arbitrary position or a desired position in the antibody or functional fragment thereof. Alternatively, the same or two or more different modifications may be made at one or two or more positions therein.

In the present invention, the term "modified form of the antibody fragment" is also meant to include even a "fragment of the modified form of the antibody".

In the present invention, a modified form of the antibody or a modified form of the functional fragment thereof is also simply referred to as an "antibody" or a "functional fragment of the antibody".

4. Methods for Producing the Antibody (4-1) Method Using a Hybridoma

In order to prepare the anti-FGFR2 antibody of the present invention, anti-FGFR2 antibody-producing cells are isolated from the spleens of animals immunized with the FGFR2 protein or its soluble form according to the method of Kohler and Milstein (Kohler and Milstein, Nature (1975), 256, p. 495-497; and Kennet, R. ed., Monoclonal Antibodies, p. 365-367, Plenum Press, N.Y. (1980)). The cells are fused with myeloma cells to thereby establish hybridomas. Monoclonal antibodies can be obtained from cultures of these hybridomas.

(4-1-1) Preparation of an Antigen

An antigen for preparation of the anti-FGFR2 antibody can be obtained according to, for example, the method for preparing a native or recombinant FGFR2 protein described in other paragraphs of the present specification. Examples of the antigen that may be thus prepared can include the FGFR2 protein and an FGFR2 protein fragment comprising a partial sequence with at least 6 consecutive amino acids of the FGFR2 protein, and their derivatives further comprising an arbitrary amino acid sequence or carrier added thereto (hereinafter, collectively referred to as an "FGFR2 antigen").

The recombinant FGFR2 antigen can be prepared by transfecting host cells with a gene comprising a nucleotide sequence encoding the amino acid sequence of the FGFR2 antigen, and recovering the antigen from cultures of the cells. Such a recombinant antigen may be a fusion protein with another protein such as an immunoglobulin Fc region. An FGFR2 antigen obtained in a cell-free in vitro translation system from a gene comprising a nucleotide sequence encoding the amino acid sequence of the FGFR2 antigen is also included in the recombinant FGFR2 antigen. The non-recombinant FGFR2 antigen can be purified or isolated from FGFR2-expressing normal tissues, cancer tissues, or cancer cells, cultures of the cancer cells, or the like described in (iv) of paragraph (2-1).

(4-1-2) Production of an Anti-FGFR2 Monoclonal Antibody (a) Purification of the Antigen This step is performed according to the method for preparing the FGFR2 protein described above in (2-3).

(b) Step of Preparing an Antibody-Producing Cell

The antigen obtained in step (a) is mixed with an adjuvant such as a complete or incomplete Freund's adjuvant or potassium aluminum sulfate, and laboratory animals are immunized with the resulting immunogen. Any laboratory animal used in a hybridoma preparation method known in the art can be used without limitations. Specifically, for example, mice, rats, goats, sheep, cattle, or horses can be used. From the viewpoint of readily available myeloma cells to be fused with isolated antibody-producing cells, etc., the animals to be immunized are preferably mice or rats.

The strain of mice or rats actually used is not particularly limited. In the case of mice, for example, A, AKR, BALB/c, BALB/cAnNCrj, BDP, BA, CE, C3H, 57BL, C57BL, C57L, DBA, FL, HTH, HT1, LP, NZB, NZW, RF, R III, SJL, SWR, WB, or 129 can be used. In the case of rats, for example, Wistar, Low, Lewis, Sprague-Dawley, ACI, BN, or Fischer can be used.

Such mice and rats are available from laboratory animal breeders or distributors, for example, CLEA Japan, Inc. or Charles River Laboratories Japan Inc.

Of these mice and rats, a BALB/c mouse strain or Wistar and Low rat strains are particularly preferred as animals to be immunized in consideration of fusion compatibility with the myeloma cells described later.

Also, in consideration of the homology between human and mouse antigens, mice whose biological mechanism to remove autoantibodies has been reduced, i.e., autoimmune disease mice, are also preferably used.

In this context, these mice or rats are preferably 5 to 12 weeks old, more preferably 6 to 8 weeks old, at the time of immunization.

The animals can be immunized with the FGFR2 protein using, for example, the method of Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Ill. (1964).

Examples of methods for determining antibody titers can include, but are not limited to, immunoassay such as RIA and ELISA.

Antibody-producing cells derived from spleen cells or lymphocytes separated from the immunized animals, can be prepared according to a method known in the art, for example, Kohler et al., Nature (1975) 256, p. 495; Kohler et al., Eur. J. Immol. (1977) 6, p. 511; Milstein et al., Nature (1977), 266, p. 550; Walsh, Nature, (1977) 266, p. 495.

In the case of spleen cells, a general method can be adopted, which involves chopping the spleens, filtering cells through a stainless mesh, and then floating the resulting cells in an Eagle's minimum essential medium (MEM) or the like, to separate antibody-producing cells.

(c) Step of Preparing Myeloma

The myeloma cells used in cell fusion are not particularly limited and can be selected appropriately for use from cell lines known in the art. For example, a hypoxanthine-guanine phosphoribosyl transferase (HGPRT)-deficient line, i.e., mouse-derived X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), FO, 5149/5XXO, or BU.1, rat-derived 210.RSY3.Ag.1.2.3 (Y3), or human-derived U266AR (SKO-007), GM1500-GTG-A12 (GM1500), UC729-6, LICR-LOW-HMy2 (HMy2), or 8226AR/NIP4-1 (NP41), whose screening procedures have already been established, is preferably used in consideration of convenience in the selection of hybridomas from fusion cells. These HGPRT-deficient lines are available from, for example, American Type Culture Collection (ATCC).

These cell lines are subcultured in an appropriate medium, for example, an 8-azaguanine medium [RPMI-1640 medium supplemented with glutamine, 2-mercaptoethanol, gentamicin, and fetal bovine serum (hereinafter, referred to as "FBS") and further supplemented with 8-azaguanine], an Iscove's modified Dulbecco's medium (hereinafter, referred to as "IMDM"), or a Dulbecco's modified Eagle medium (hereinafter, referred to as "DMEM") and subcultured in a normal medium [e.g., ASF104 medium (manufactured by Ajinomoto Co., Inc.) containing 10% FBS] 3 to 4 days before cell fusion to secure that the number of cells is equal to or greater than $2 \times 10^7$ cells on the day of cell fusion.

(d) Fusing the Antibody-Producing Cell with a Myeloma Cell

The antibody-producing cells can be fused with the myeloma cells under conditions that prevent cell viability from being exceedingly reduced, according to any method known in the art (e.g., Weir, D. M., Handbook of Experimental Immunology Vol. I. II. III., Blackwell Scientific Publications, Oxford (1987)). For example, a chemical method which involves mixing antibody-producing cells with myeloma cells in a high-concentration solution of a polymer such as polyethylene glycol, or a physical method using electric stimulation can be used.

(e) Screening for a Hybridoma Group Producing the Antibody of Interest

A method for selection from the hybridomas obtained by the cell fusion is not particularly limited, and a hypoxanthine-aminopterin-thymidine (HAT) selection method (Kohler et al., Nature (1975) 256, p. 495; Milstein et al., Nature (1977) 266, p. 550) is typically used. This method is effective for obtaining hybridomas using an HGPRT-deficient myeloma cell line, which cannot survive in the presence of aminopterin. Specifically, unfused cells and hybridomas can be cultured in a HAT medium to thereby allow only hybridomas resistant to aminopterin to selectively live and grow.

(f) Obtaining a Single Cell Clone (Cloning)

The hybridomas can be cloned using any method known in the art, for example, a methylcellulose, soft agarose, or limiting dilution method (see e.g., Barbara, B. M. and Stanley, M. S.: Selected Methods in Cellular Immunology, W.H. Freeman and Company, San Francisco (1980)). The limiting dilution method is preferred.

(g) Culturing the Hybridoma and Raising a Hybridoma-Transplanted Animal

The selected hybridomas can be cultured to thereby produce monoclonal antibodies. Preferably, the desired hybridomas are cloned and then subjected to antibody production.

The monoclonal antibody produced by such a hybridoma can be recovered from cultures of the hybridoma. Also, a recombinant antibody can be recovered from cultures of cells transfected with the monoclonal antibody gene. Alternatively, the hybridoma may be injected intraperitoneally to mice of the same strain (e.g., BALB/cAnNCrj described above) or Nu/Nu mice and allowed to grow. Then, the monoclonal antibody can be recovered from their ascites.

(h) Assaying or Determining the Biological Activity of the Monoclonal Antibody

Various biological tests can be selected and applied thereto according to the purpose.

(4-2) Cell Immunization Method

Cells expressing the native FGFR2 protein, cells expressing the recombinant FGFR2 protein or its fragment, or the like, can be used as immunogens to thereby prepare an anti-FGFR2 antibody by the hybridoma method described above.

Examples of cells expressing the native FGFR2 protein can include FGFR2-expressing cells, cell lines derived from FGFR2-expressing tissues or cancer, and cell lines derived from cancer tissues in which switching from FGFR2 IIIb to FGFR2 IIIc expression is seen. Cancers highly expressing FGFR2 include: cancers found to have gene amplification, such as stomach cancer and breast cancer; and cancers found to have overexpression, such as pancreatic cancer and ovarian cancer. Examples of cultured cell lines highly expressing FGFR2 IIIb can include stomach cancer cell lines and breast cancer cell lines. Examples of cultured cell lines highly expressing FGFR2 IIIc can include colorectal (cecal) cancer cell lines. Examples of cancer tissues in which switching from FGFR2 IIIb to FGFR2 IIIc expression is seen can include tissues of prostate cancer, urinary bladder cancer, and breast cancer. Examples of cancer tissues expressing FGFR2 IIIc can include tissues of uterine cervix cancer and non-small cell lung cancer. Of these cancers, uterine cervix cancer highly expresses FGFR2 IIIc. Examples of normal tissues highly expressing FGFR2 can include the brain, the large intestine, thyroid glands, the uterus, the gallbladder, and the skin.

These FGFR2-expressing cells are used in an amount of $1 \times 10^5$ to $1 \times 10^9$ cells, preferably $1 \times 10^6$ to $1 \times 10^8$ cells, more preferably 0.5 to $2 \times 10^7$ cells, even more preferably $1 \times 10^7$ cells, per immunization shot. The number of cells used for immunization can be changed according to the expression level of the FGFR2 protein. The immunogens are generally administered intraperitoneally and may be administered through an intradermal route or the like. The hybridomas can be prepared by the application of the method described in paragraph (4-1-2).

(4-3) Gene Recombination

In order to prepare the antibody of the present invention, a nucleotide (heavy chain nucleotide) comprising a nucleotide sequence encoding the amino acid sequence of its heavy chain and a nucleotide (light chain nucleotide) comprising a nucleotide sequence encoding the amino acid sequence of its light chain, or a vector having an insert of the heavy chain nucleotide and a vector having an insert of the light chain nucleotide are introduced into host cells, and then the cells are cultured, and the antibody can be recovered from the cultures. The heavy chain nucleotide and the light chain nucleotide may be inserted in one vector.

Prokaryotic or eukaryotic cells can be used as the host cells. In the case of using host eukaryotic cells, animal cells, plant cells, or eukaryotic microbes can be used.

Examples of animal cells can include mammal-derived cells, i.e., monkey-derived COS cells (Gluzman, Y. Cell (1981), 23, p. 175-182, ATCC CRL-1650), mouse fibroblast NIH3T3 (ATCC No. CRL-1658), a mouse NSO cell line (ECACC), Chinese hamster ovary cells (CHO cells, ATCC CCL-61), dihydrofolate reductase-deficient lines thereof (CHO$^{dhfr-}$; Urlaub, G. and Chasin, L. A. Proc. Natl. Acad. Sci. U.S.A. (1980), 77, p. 4126-4220), CHOK1SV (Lonza Biologics), cells derived from birds such as chickens, and cells derived from insects.

Examples of eukaryotic microbes can include yeasts.

Examples of prokaryotic cells can include *E. coli* and *Bacillus subtilis*.

A signal peptide for secretion of the antibody of the present invention (monoclonal antibody derived from each animal, rat antibody, mouse antibody, chimeric antibody, humanized antibody, human antibody, etc.) is not limited to the secretory signal of an antibody of the same species, the same type, and the same subtype as the antibody of the present invention or to the antibody of the present invention's own secretory signal. Any secretory signal of an antibody of different type or subtype therefrom or any secretory signal of a protein derived from a different eukaryotic species therefrom or a prokaryotic species can be selected and used.

(4-4) Methods for Designing and Preparing a Humanized Antibody

Examples of the humanized antibody can include, but are not limited to, a human-derived antibody having CDRs replaced with the CDRs of a non-human animal antibody (see Nature (1986), 321, p. 522-525), a human antibody grafted with the CDR sequences and with some amino acid residues of framework regions by CDR grafting (see WO90/07861 and U.S. Pat. No. 6,972,323), and an antibody having human antibody amino acid(s) replaced for one or two or more non-human animal antibody-derived amino acid(s) in any of these humanized antibodies.

(4-5) Methods for Preparing a Human Antibody

Further examples of the antibody of the present invention can include a human antibody. The anti-FGFR2 human antibody means an anti-FGFR2 antibody consisting of the amino acid sequence of a human-derived antibody. The anti-FGFR2 human antibody can be obtained by a method using human antibody-producing mice carrying human genomic DNA fragments comprising human antibody heavy and light chain genes (see e.g., Tomizuka, K. et al., Nature Genetics (1997) 16, p. 133-143; Tomizuka, K. et. al., Proc. Natl. Acad. Sci. USA (2000) 97, p. 722-727).

Specifically, such human antibody-producing animals may be any of the recombinant animals that are obtained by disrupting the endogenous immunoglobulin heavy and light chain gene loci of non-human mammals and instead introducing thereto human immunoglobulin heavy and light chain gene loci via yeast artificial chromosome (YAC) vectors or the like, and recombinant animals that are created by crossing these animals.

Alternatively, eukaryotic cells may be transfected with cDNAs encoding the heavy and light chains, respectively, of such a human antibody, preferably with vectors comprising the cDNAs, by a gene recombination technique. The transfected cells producing a recombinant human monoclonal antibody can be cultured. This antibody can be obtained from the culture supernatant. In this context, for example, eukaryotic cells, preferably mammalian cells such as CHO cells, lymphocytes, or myelomas, can be used as the hosts.

Also, a method for obtaining a phage display-derived human antibody selected from a human antibody library (see e.g., Siriwardena, D. et. al., Opthalmology (2002) 109 (3), p. 427-431) is known. For example, a phage display method (Nature Biotechnology (2005), 23, (9), p. 1105-1116) can be used, which involves allowing the variable regions of a human antibody to be expressed as a single chain antibody (scFv) on a phage surface and selecting a phage binding to the antigen. The phage selected on the basis of its ability to bind to the antigen can be subjected to gene analysis to thereby determine DNA sequences encoding the variable regions of the human antibody binding to the antigen. If the DNA sequence of the scFv binding to the antigen is determined, an expression vector having this sequence can be prepared and introduced to appropriate hosts to allow them to express the human antibody (e.g., Nature Biotechnology (2005) 23 (9), p. 1105-1116).

(4-6) Methods for Preparing a Functional Fragment of the Antibody

The method for preparing a single chain antibody is well known in the art (see e.g., U.S. Pat. Nos. 4,946,778, 5,260, 203, 5,091,513, and 5,455,030). In this scFv, a heavy chain variable region and a light chain variable region are linked via a linker that prevents them from forming a conjugate, preferably a polypeptide linker (Huston, J. S. et al., Proc. Natl. Acad. Sci. U.S.A. (1988), 85, p. 5879-5883). The heavy chain variable region and the light chain variable region in the scFv may be derived from the same antibody or may be derived from different antibodies.

For example, an arbitrary single chain peptide consisting of 12 to 19 residues is used as the polypeptide linker that links these variable regions.

In order to obtain scFv-encoding DNA, of the sequences of DNA encoding the heavy chain or heavy chain variable region of the antibody and DNA encoding the light chain or light chain variable region thereof, each DNA portion encoding the whole or desired amino acid sequence is used as a template and amplified by PCR using a primer pair flanking both ends of the template. Subsequently, DNA encoding the polypeptide linker moiety is further amplified in combination with a primer pair flanking both ends of the DNA so that the obtained fragment can be linked at its ends to the heavy and light chain DNAs, respectively.

The scFv-encoding DNA can be used to thereby prepare, according to a routine method, an expression vector containing the DNA and host cells transformed with the expression vector. In addition, the host cells can be cultured, and the scFv can be recovered from the cultures according to a routine method.

Also in order to obtain any other functional fragment of the antibody, a gene encoding the functional fragment is obtained according to the method described above and introduced into cells. The functional fragment of interest can be recovered from cultures of the cells.

The antibody of the present invention may be multimerized to thereby enhance its affinity for the antigen. In this case, antibodies of the same type may be multimerized, or a plurality of antibodies recognizing a plurality of epitopes, respectively, of the same antigen may be multimerized. Examples of methods for multimerizing these antibodies can include the binding of two scFvs to an IgG CH3 domain, the binding thereof to streptavidin, and the introduction of a helix-turn-helix motif.

The antibody of the present invention may be a mixture of plural types of anti-FGFR2 antibodies differing in amino acid sequence, i.e., a polyclonal antibody. Examples of a polyclonal antibody can include a mixture of plural types of antibodies differing in a portion or the whole of CDRs. Such a polyclonal antibody can be recovered from cultures of mixed-cultured different antibody-producing cells (WO2004/061104). Alternatively, separately prepared antibodies may be mixed. Antiserum, which is one aspect of the polyclonal antibody, can be prepared by immunizing animals with the desired antigen and recovering serum from the animals according to a standard method.

Antibodies conjugated with various molecules such as polyethylene glycol (PEG) can also be used as modified forms of the antibody.

The antibody of the present invention may further be a conjugate formed by these antibodies with other drugs (immunoconjugates). Examples of such an antibody can include the antibody conjugated with a radioactive material or a compound having a pharmacological action (Nature Biotechnology (2005), 23, p. 1137-1146).

(4-7) Purification of the Antibody

The obtained antibody can be purified until homogeneous. Usual protein separation and purification methods can be used for the separation and purification of the antibody.

The antibody can be separated and purified by appropriately selected or combined approach(es), for example, chromatography columns, filters, ultrafiltration, salting out, dialysis, preparative polyacrylamide gel electrophoresis, and/or isoelectric focusing (e.g., Antibodies: A Laboratory Manual. Ed Harlow and David Lane, Cold Spring Harbor Laboratory (1988)) though the separation and purification method is not limited thereto.

Examples of chromatography include affinity chromatography, ion-exchange chromatography, hydrophobic chromatography, gel filtration, reverse-phase chromatography, and adsorption chromatography.

These chromatography approaches can be performed using liquid-phase chromatography such as HPLC or FPLC.

Examples of columns used in affinity chromatography can include protein A, protein G, and antigen columns.

Examples of the protein A columns include Protein A Ceramic HyperD (manufactured by Pall Corp.), POROS (manufactured by Applied Biosystems, Inc.), and Sepharose F.F. (manufactured by GE Healthcare Bio-Sciences Corp.).

Also, the antibody may be purified using its binding activity against the antigen using an antigen-immobilized carrier.

(4-8) Nucleotides Encoding the Antibody, Recombinant Vectors, and Recombinant Cells The present invention provides a nucleotide(s) encoding the antibody of the present invention or a functional fragment thereof, or a modified form of the antibody or functional fragment (hereinafter, this nucleotide is referred to as an "antibody gene"), a recombinant vector having an insert of the gene, a cell comprising the gene or the vector (hereinafter, this cell is referred to as an "antibody gene-transfected cell"), and a cell producing the antibody of the present invention or a functional fragment thereof, or a modified form of the antibody or functional fragment (hereinafter, this cell is referred to as an "antibody-producing cell").

Preferably, the antibody gene of the present invention comprises a nucleotide sequence described in any one of the following (a) to (e) (hereinafter, referred to as an "antibody gene sequence"), consists of a nucleotide sequence comprising the antibody gene sequence, or consists of the antibody gene sequence:

(a) a combination of a nucleotide sequence encoding the heavy chain amino acid sequence of the rat FR2-2nd_#023 antibody or the mouse chimeric antibody thereof or the rat FR2-2nd_#028 antibody or the mouse chimeric antibody thereof and a nucleotide sequence encoding the light chain amino acid sequence thereof;

(b) a combination of a nucleotide sequence encoding the amino acid sequence of a heavy chain comprising CDRH1 to CDRH3 of any of the antibodies described in (a) and a nucleotide sequence encoding the amino acid sequence of a light chain comprising CDRL1 to CDRL3 of any of thereof;

(c) a combination of a nucleotide sequence encoding a heavy chain amino acid sequence comprising the amino acid sequence of the heavy chain variable region of any of the antibodies described in (a) and a nucleotide sequence encoding a light chain amino acid sequence comprising the amino acid sequence of the light chain variable region of any of thereof;

(d) a nucleotide sequence that hybridizes under stringent conditions to a nucleotide consisting of a nucleotide sequence complementary to any one of the nucleotide sequences (a) to (c) and encodes the amino acid sequence of an antibody binding to FGFR2; and (e) a nucleotide sequence that encodes an amino acid sequence derived from any one of the amino acid sequences (a) to (c) by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and encodes the amino acid sequence of an antibody binding to FGFR2.

However, the antibody gene of the present invention is not limited to those described in (a) to (e).

The present invention provides, as described in paragraph (4-3), a method for producing the antibody of the present invention or a functional fragment thereof, or a modified form of the antibody or functional fragment, comprising the steps of: culturing the antibody gene-transfected cell of the present invention and recovering the antibody, the functional fragment, or the modified form from the cultures. The antibody or functional fragment thereof, or the modified form of the antibody or functional fragment obtained by this production method is also included in the present invention.

5. Composition for Diagnosis

The present invention provides a composition for testing or diagnosis (hereinafter, collectively referred to as a "composition for diagnosis") comprising the anti-FGFR2 antibody of the present invention or a functional fragment thereof, or a modified form of the antibody or functional fragment.

The composition for diagnosis of the present invention is useful in the testing or diagnosis of FGFR2-related diseases such as cancer or of FGFR2 expression. In the present invention, the testing or the diagnosis includes, for example, the determination or measurement of a risk of developing a disease, the determination of the presence or absence of a disease, the measurement of the degree of progression or exacerbation of a disease, the measurement or determination of the effect of drug therapy using the pharmaceutical composition comprising the anti-FGFR2 antibody or the like, the measurement or determination of the effect of therapy other than drug therapy, the measurement of a risk of recurrence of a disease, and the determination of the presence or absence of recurrence of a disease. However, the testing or diagnosis according to the present invention is not limited to these, and any approach can be used.

The composition for diagnosis of the present invention is useful in the identification of a recipient individual for the antibody of the present invention or the functional fragment thereof, or a modified form of the antibody or functional fragment, a composition comprising the same, or a pharmaceutical composition comprising the same.

The composition for diagnosis can comprise a pH buffer, an osmoregulator, salts, a stabilizer, an antiseptic, a color developer, a sensitizer, an aggregation inhibitor, and the like.

The present invention also provides a method for testing or diagnosing FGFR2-related diseases such as cancer, use of the antibody of the present invention for preparing a composition for diagnosis of the diseases, and use of the antibody of the present invention for testing or diagnosing the diseases. The present invention also encompasses a kit for testing or diagnosis comprising the antibody of the present invention.

The desirable testing or diagnosis method involving the antibody of the present invention is sandwich ELISA. Any usual detection method using antibodies, such as ELISA, RIA, enzyme-linked immunospot (ELISPOT) assay, dot blotting, Ouchterlony test, counterimmunoelectrophoresis (CIE), chemiluminescent immunoassay (CLIA), or flow cytometry (FCM), may be used. The antibodies can be labeled by a method using biotin or by any other labeling method that can be carried out in biochemical analysis using, for example, a label such as HRP, alkaline phosphatase, a fluorophore (e.g., FITC), or a radioisotope. A chromogenic substrate such as TMB (3,3',5,5'-tetramethylbenzidine), BCIP (5-bromo-4-chloro-3-indolyl phosphate), ρ-NPP (ρ-nitrophenyl phosphate), OPD (o-Phenylenediamine), ABTS (3-Ethylbenzothiazoline-6-sulfonic acid), and SuperSignal ELISA Pico Chemiluminescent Substrate (Thermo Fisher Scientific Inc.), a fluorescent substrate QuantaBlu™ Fluorogenic Peroxidase Substrate (Thermo Fisher Scientific Inc.), and a chemiluminescent substrate can be used in detection using enzymatic labeling. Samples derived from humans or non-human animals as well as artificially treated samples such as recombinant proteins can be subjected to this assay. Examples of test samples derived from individual organisms can include, but are not limited to, blood, synovial fluids, ascites, lymph, cerebrospinal fluids, tissue homogenate supernatants, and tissue sections.

The sandwich ELISA kit for testing or diagnosis comprising the antibody of the present invention may comprise a solution of FGFR2 protein standards, a coloring reagent, a buffer solution for dilution, an antibody for solid phase, an antibody for detection, and a washing solution, and the like. Preferably, the amount of the antibody bound to the antigen can be measured by the application of a method such as an absorbance, fluorescence, luminescence, or radioisotope (RI) method. Preferably, an absorbance plate reader, a fluorescence plate reader, a luminescence plate reader, an RI liquid scintillation counter, or the like is used in the measurement.

Such a composition, etc. of the present invention can be used not only in these immunohistological tests but in Western blotting or dot blot which involves preparing soluble proteins according to a routine method from cells, tissues, or an organ in a sample, or a portion thereof, and reacting the soluble proteins with a labeled antibody to confirm the presence or absence of FGFR2 in the soluble proteins.

The present invention provides an antibody useful for immunohistochemistry (IHC) analysis or a functional fragment thereof, and a modified form of the antibody or functional fragment, and a composition comprising the same. Such a composition is also encompassed by the "composition for diagnosis" of the present invention.

The immunohistochemistry is not particularly limited as long as this approach involves reacting a tissue section with an antigen-binding antibody (primary antibody) and detecting the primary antibody bound with the antigen.

Preferably, the tissue section is fixed in formalin and then treated with paraffin. The paraffin-treated tissue section is deparaffinized, followed by antigen retrieval treatment and nonspecific reaction inhibition treatment. Examples of methods for the antigen retrieval treatment (hereinafter, also simply referred to as "retrieval") can include heat treatment and enzymatic treatment.

The heat treatment is usually performed under preferred conditions involving a temperature of 80 to 110° C., pH 7 to 12, and a treatment time ranging from 1 to 300 minutes, more preferably a temperature of 90 to 100° C., pH 8 to 10, and a treatment time of 20 to 60 minutes. A buffer solution, more preferably, a buffer solution containing EDTA (examples thereof include, but are not limited to, a 10 mM Tris buffer solution containing 1 mM EDTA) or the like can be used in pH adjustment. Examples of commercially available buffer solutions can include Bond Epitope Retrieval Solution 2 (manufactured by Leica Biosystems Nussloch GmbH; pH 9, EDTA-containing). The retrieval by heat treatment can be preferably used in the detection of an antigen using the rat FR2-2nd_#023 antibody, the mouse chimeric FR2-2nd_#023 antibody, or an antibody having a structure and/or binding specificity similar thereto.

The enzymatic treatment is usually performed under preferred conditions involving a temperature of 10 to 50° C. and a treatment time ranging from 1 to 120 minutes, more preferably a temperature of 20 to 38° C. and a treatment time ranging from 5 to 10 minutes. The enzyme is not particularly limited as long as the enzyme is protease. For example, proteinase or peptidase such as trypsin can be used. Examples of commercially available proteinase can include Enzyme Proteinase K (IHC) (manufactured by Leica Biosystems Nussloch GmbH) and DAKO Proteinase K RTU (manufactured by DAKO/Agilent Technologies, Inc.). The retrieval by enzymatic treatment can be preferably used in the detection of an antigen using the rat FR2-2nd_#028 antibody, the mouse chimeric FR2-2nd_#028 antibody, or an antibody having a structure and/or binding specificity similar thereto.

A method for inactivating an endogenous enzyme having the same or similar catalytic activity as an enzyme used in color development is usually used as the nonspecific reaction inhibition treatment. For color development through peroxidase reaction, endogenous peroxidase present in tissues is preferably inhibited in advance using $H_2O_2$ or the like. A solvent such as water or methanol can be used for $H_2O_2$. The concentration of $H_2O_2$ is 0.1 to 3%, preferably 0.3 to 3%. The $H_2O_2$ solution can be supplemented with sodium azide. Also, a blocking method using serum or casein can be used as the nonspecific reaction inhibition treatment. Tissues can be treated with serum or casein before the primary antibody reaction. Alternatively, serum or casein may be contained in a solvent for diluting the primary antibody.

The reaction conditions for the primary antibody are not particularly limited and involve a temperature of 20 to 50° C., preferably 25 to 42° C., more preferably 37° C. The reaction time is 5 minutes to all night and all day, preferably 10 minutes to 6 hours, more preferably 30 minutes to 2 hours.

Preferably, an antibody (secondary antibody) capable of being visualized and binding to the primary antibody can be used in the detection of the primary antibody. Preferably, the secondary antibody can be visualized by use of a method involving binding an enzyme such as peroxidase or alkaline phosphatase to the secondary antibody or adding biotin or the like to the secondary antibody and binding thereto streptavidin or the like conjugated with the enzyme, followed by reaction with a chromogenic substrate compatible with the enzyme. Examples of the method involving binding an enzyme to the secondary antibody can include a method using a reagent comprising a dextrin polymer or an amino acid polymer to which multiple molecules of the enzyme and the secondary antibody are attached (polymer method). A chromogenic substrate such as DAB can be used in the method involving reacting a biotinylated secondary antibody with peroxidase-labeled streptavidin (LSAB method). Also, a secondary antibody labeled with a fluorescent dye or the like can be used. After treatment with the fluorescently labeled secondary antibody, positive cells are detected using a fluorescence microscope.

A smear method involves separating isolated cells into cellular components and fluid components by application to glass or centrifugation in a centrifuge and immunostaining the cellular components. Specifically, the cellular components can be applied onto a glass slide, fixed in an ethanol solution, a 10% formalin solution, or the like, and then immunostained in the same way as in the tissue section.

A freeze embedding method involves embedding isolated tissues in an OCT compound or the like, then rapidly freezing the embedded tissues in liquid nitrogen or the like, and slicing the frozen tissues using a cryostat to prepare a slide preparation. This preparation can be fixed in a 10% formalin solution, an ethanol solution, or the like and then immunostained in the same way as in the tissue section.

The immunohistochemistry procedure can be performed automatically using an immunological apparatus programmed with a reaction solution, reaction conditions, the number of washing runs, etc.

For diagnostic imaging, an antibody is labeled with a pharmaceutically acceptable radionuclide or luminescent material and administered to a test subject, and images can be taken using a diagnostic imaging technique such as PET/CT to determine or test the presence of FGFR2.

The antibody or functional fragment thereof, or a modified form of the antibody or functional fragment comprised in the composition for diagnosis of the present invention is preferably an antibody binding to FGFR2, i.e., an antibody having FGFR2 selectivity or a functional fragment thereof, or a modified form of the antibody or functional fragment, more preferably an antibody having selectivity for both human FGFR2 IIIb and human FGFR2 IIIc or functional fragment thereof or a modified form of the antibody or functional fragment. More preferably, according to another aspect, the antibody or functional fragment thereof, or a modified form of the antibody or functional fragment contained in the composition for diagnosis of the present invention has selectivity for human FGFR2 IIIc.

Examples of the antibody having selectivity for both human FGFR2 IIIb and human FGFR2 IIIc can include an antibody comprising a heavy chain comprising the heavy chain CDRH1 to CDRH3 of the rat FR2-2nd_#023 antibody and a light chain comprising the light chain CDRL1 to CDRL3 thereof, an antibody comprising the heavy and light chain variable regions of the rat FR2-2nd_#023 antibody, and an antibody comprising the heavy and light chains of the rat FR2-2nd_#023 antibody. Examples of such an antibody can include, but are not limited to, the rat FR2-2nd_#023 antibody and the mouse chimeric FR2-2nd_#023 antibody.

Examples of the antibody having selectivity for human FGFR2 IIIc can include an antibody comprising a heavy chain comprising the heavy chain CDRH1 to CDRH3 of the rat FR2-2nd_#028 antibody and a light chain comprising the light chain CDRL1 to CDRL3 thereof, an antibody comprising the heavy and light chain variable regions of the rat FR2-2nd_#028 antibody, and an antibody comprising the heavy and light chains of the rat FR2-2nd_#028 antibody. Examples of such an antibody can include, but are not limited to, the rat FR2-2nd_#028 antibody and the mouse chimeric FR2-2nd_#028 antibody.

According to a preferred aspect, the composition for diagnosis of the present invention is for detection or assay of FGFR2, more preferably for detection or assay of human FGFR2 IIIb and/or human FGFR2 IIIc, even more preferably for detection or assay of human FGFR2 IIIb and human FGFR2 IIIc or of human FGFR2 IIIc.

The present invention provides a method for detecting or assaying human FGFR2 IIIc in a test sample.

Alternatively, human FGFR2 IIIc in a test sample can be detected or assayed by: (i) detecting or assaying human FGFR2 IIIb and human FGFR2 IIIc in the test sample; (ii) detecting or assaying human FGFR2 IIIb in the sample; and (iii) comparing the results of detection or assay in step (i) with the results of detection or assay in step (ii) or subtracting the results of detection or assay in step (ii) from the results of detection or assay in step (i). Such a method for detecting or assaying human FGFR2 IIIc is also encompassed in the present invention.

Examples of the antibody or antigen binding fragment thereof, or the composition used in the detection or assay of human FGFR2 IIIb and human FGFR2 IIIc in step (i) include, but are not limited to, the rat FR2-2nd_#023 antibody, the mouse chimeric FR2-2nd_#023 antibody, and a composition comprising the same. The composition may contain an additional antibody.

Examples of the antibody or antigen binding fragment thereof, or the composition used in the detection or assay of human FGFR2 IIIb in step (ii) include an antibody specifically binding to human FGFR2 IIIb or an antigen binding fragment thereof (e.g., a rat FR2-10 antibody or a chimeric antibody thereof (WO2013/154206)), and a composition comprising the same.

The present invention provides a method for detecting or assaying human FGFR2 IIIb in a test sample.

Alternatively, human FGFR2 IIIb in a test sample can be detected or assayed by: (i) detecting or assaying human FGFR2 IIIb and human FGFR2 IIIc in the test sample; (ii) detecting or assaying human FGFR2 IIIc in the sample; and (iii) comparing the results of detection or assay in step (i) with the results of detection or assay in step (ii) or subtracting the results of detection or assay in step (ii) from the results of detection or assay in step (i). Such a method for detecting or assaying human FGFR2 IIIb is also encompassed in the present invention.

Examples of the antibody or antigen binding fragment thereof, or the composition used in the detection or assay of human FGFR2 IIIb and human FGFR2 IIIc in step (i) include, but are not limited to, the rat FR2-2nd_#023 antibody, the mouse chimeric FR2-2nd_#023 antibody, and a composition comprising the same. The composition may contain an additional antibody.

Examples of the antibody or antigen binding fragment thereof, or the composition used in the detection or assay of human FGFR2 IIIc in step (ii) include, but are not limited to, the rat FR2-2nd_#028 antibody, the mouse chimeric FR2-2nd_#028 antibody, and a composition comprising the same.

The composition for diagnosis of the present invention can be used in these detection or assay methods. The present invention also encompasses such an assay method and a composition for diagnosis which are intended for diagnosis or testing of human FGFR2-positive cancer, preferably human FGFR2 IIIb- and/or human FGFR2 IIIc-positive cancer, more preferably human FGFR2 IIIc-positive cancer or human FGFR2 IIIb and human FGFR2 IIIc-positive cancer.

The present invention also encompasses a method for identifying a recipient individual for the pharmaceutical composition of the present invention. This identification method involves assaying human FGFR2 in a sample derived from the individual. The individual can be determined to be positive when human FGFR2 is detected in the sample or when human FGFR2 is detected in a larger amount than that of human FGFR2 detected in a sample derived from a healthy individual. The human FGFR2 in the identification method is preferably human FGFR2 IIIb and/or human FGFR2 IIIc, more preferably human FGFR2 IIIb and human FGFR2 IIIc, or human FGFR2 IIIc.

The composition for diagnosis of the present invention can be used in this method.

According to a preferred aspect, the individual in the identification method has cancer or is at risk thereof.

According to one aspect, the pharmaceutical composition of the present invention can be administered to an individual determined to be positive by the identification method.

6. Pharmaceutical Composition

The present invention provides a pharmaceutical composition comprising an anti-FGFR2 antibody or a functional fragment thereof, or a modified form of the antibody or functional fragment (WO2013/154206, WO2015/053407, etc.).

Examples of the antibody for the pharmaceutical composition specifically binding to human FGFR2 can include HuGAL-FR21 MAb, BAY-1179470, BAY-1187982, FGFR2/FGFR4 dual targeting antibody-drug conjugate (Novartis International AG), and antibodies described in WO2013/154206 (including hFR2-14_H19/L and hFR2-14_H12/L1). These antibodies can be preferably used in the treatment or prevention of human FGFR2-positive diseases. Examples of the antibody for the pharmaceutical composition specifically binding to human FGFR2 IIIc, particularly, the antibody for the pharmaceutical composition specifically binding to human FGFR2 IIIc and human FGFR2 IIIb, can include antibodies described in WO2013/154206 (including hFR2-14_H19/L1 and hFR2-14_H12/L1). These antibodies can be preferably used in the treatment or prevention of human FGFR2 IIIc-positive diseases, particularly, human FGFR2 IIIc- and human FGFR2 IIIb-positive diseases.

The pharmaceutical composition of the present invention is useful in the treatment or prevention of various diseases that are initiated or exacerbated by abnormal or increased FGFR2 signals due to overexpression of FGFR2 or its ligand or FGFR2 mutations or gene amplification, or by isoform switching of FGFR2 (hereinafter, these diseases are referred to as "FGFR2-related diseases"), particularly, various cancers.

Examples of causes of the initiation or exacerbation of such cancers to be treated or prevented can include single nucleotide polymorphism (SNP) in an intron of the FGFR2 gene, high expression of FGFR2, missense mutations that constitutively activate FGFR2, amplification or overexpression of the FGFR2 gene, and switching from FGFR2 IIIb to FGFR2 IIIc.

Examples of such cancer types can include breast cancer, endometrial cancer, ovary cancer, lung cancer (e.g., non-small cell lung cancer), stomach cancer, prostate cancer, kidney cancer, liver cancer, pancreatic cancer, colorectal cancer, esophageal cancer, urinary bladder cancer, uterine cervix cancer, blood cancer, lymphoma, and malignant melanoma. Preferred examples thereof can include these cancers expressing the FGFR2 protein.

In the present invention, the treatment or prevention of a disease includes, but is not limited to, the prevention of the onset of the disease, preferably the disease in an individual expressing the FGFR2 protein, the suppression or inhibition of exacerbation or progression thereof, the alleviation of one or two or more symptoms exhibited by an individual affected with the disease, the suppression or remission of exacerbation or progression thereof, the treatment or prevention of a secondary disease, etc.

The pharmaceutical composition of the present invention can comprise a therapeutically or prophylactically effective amount of the anti-FGFR2 antibody or the functional fragment of the antibody and a pharmaceutically acceptable diluent, vehicle, solubilizer, emulsifier, preservative, and/or additive.

The "therapeutically or prophylactically effective amount" means an amount that exhibits therapeutic or prophylactic effects on a particular disease by means of a particular dosage form and administration route and has the same meaning as a "pharmacologically effective amount".

The pharmaceutical composition of the present invention may comprise materials for changing, maintaining, or retaining pH, osmotic pressure, viscosity, transparency, color, tonicity, sterility, or the stability, solubility, sustained release, absorbability, permeability, dosage form, strength, properties, shape, etc., of the composition or the antibody comprised therein (hereinafter, referred to as "pharmaceutical materials"). The pharmaceutical materials are not particularly limited as long as the materials are pharmacologically acceptable. For example, no or low toxicity is a property preferably possessed by these pharmaceutical materials.

Examples of the pharmaceutical materials can include amino acids, antimicrobial agents, antioxidants, buffers, fillers, chelating agents, complexing agents, bulking agents, monosaccharides, disaccharides, carbohydrates, coloring agents, corrigents, diluents, emulsifiers, hydrophilic polymers, antiseptics, solvents, sugar alcohols, suspending agents, surfactants, stability enhancers, elasticity enhancers, transport agents, diluents, excipients, and/or pharmaceutical additives. The amount of these materials added is 0.001 to 1000 times, preferably 0.01 to 100 times, more preferably 0.1 to 10 times the weight of the anti-FGFR2 antibody or functional fragment thereof, or a modified form of the antibody or functional fragment.

An immunoliposome comprising the anti-FGFR2 antibody or functional fragment thereof, or a modified form of the antibody or functional fragment encapsulated in a liposome, or a modified antibody form comprising the antibody conjugated with a liposome (U.S. Pat. No. 6,214,388, etc.) is also included in the pharmaceutical composition of the present invention.

The excipients or vehicles are not particularly limited as long as they are liquid or solid materials usually used in injectable water, saline, artificial cerebrospinal fluids, and other preparations for oral or parenteral administration. Examples of saline can include neutral saline and serum albumin-containing saline.

Examples of buffers can include a Tris buffer adjusted to bring the final pH of the pharmaceutical composition to 7.0 to 8.5, an acetate buffer adjusted to bring the final pH thereof to 4.0 to 5.5, a citrate buffer adjusted to bring the final pH thereof to 5.0 to 8.0, and a histidine buffer adjusted to bring the final pH thereof to 5.0 to 8.0.

The pharmaceutical composition of the present invention is a solid, a liquid, a suspension, or the like. Another example of the pharmaceutical composition of the present invention can include freeze-dried preparations. The freeze-dried preparations can be formed using an excipient such as sucrose.

The administration route of the pharmaceutical composition of the present invention may be any of enteral administration, local administration, and parenteral administration. Examples thereof can include intravenous administration, intraarterial administration, intramuscular administration, intradermal administration, hypodermic administration, intraperitoneal administration, transdermal administration, intraosseous administration, intraarticular administration, and the like.

The composition of a pharmaceutical composition can be determined according to the administration method, the binding affinity of the antibody for the FGFR2 protein, etc. The anti-FGFR2 antibody of the present invention or a functional fragment thereof, or a modified form of the antibody or functional fragment having higher affinity (lower KD value) for the FGFR2 protein can exhibit its pharmaceutical efficacy at a lower dose.

The dose of the anti-FGFR2 antibody of the present invention is not limited as long as the dose is a pharmacologically effective amount. The dose can be appropriately determined according to the species of an individual, the type of disease, symptoms, sex, age, pre-existing conditions, the binding affinity of the antibody for the FGFR2 protein or its biological activity, and other factors. A dose of usually 0.01 to 1000 mg/kg, preferably 0.1 to 100 mg/kg, can be administered once every day to every 180 days or twice or three or more times a day.

Examples of the form of the pharmaceutical composition can include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

The pharmaceutical composition comprising the anti-FGFR2 antibody or functional fragment thereof, or a modified form of the antibody or functional fragment as an active ingredient can be administered concurrently with or separately from an additional drug. For example, the pharmaceutical composition comprising the anti-FGFR2 antibody or functional fragment thereof as an active ingredient may be administered after administration of the additional drug, or the additional drug may be administered after administration of the pharmaceutical composition. Alternatively, the pharmaceutical composition and the additional drug may be administered concurrently. Examples of the additional drug can include various anticancer agents such as chemotherapeutics and radiation therapy. These use approaches are collectively referred to as "combined use of the additional drug" with the antibody of the present invention. The present invention also encompasses a pharmaceutical composition comprising the antibody of the present invention or a functional fragment thereof, or a modified form of the antibody or functional fragment and further comprising an additional drug.

The present invention provides a method for treating or preventing FGFR-related diseases such as cancer, use of the antibody of the present invention for preparing a pharmaceutical composition for treatment or prevention of the diseases, and use of the antibody of the present invention for treating or preventing the diseases. The present invention also encompasses a kit for treatment or prevention comprising the antibody of the present invention.

7. Reagent and Kit

The antibody of the present invention or functional fragment thereof, or a modified form of the antibody or a functional fragment is also useful as a reagent and a kit. Such a reagent and a kit are used for testing or diagnosis as mentioned above, for research, and for any other use.

EXAMPLES

Hereinafter, the present invention will be described further specifically with reference to the Examples. However, the present invention is not intended to be limited to them.

Procedures related to gene manipulation in the Examples below were performed according to the methods described in "Molecular Cloning" (Sambrook, J., Fritsch, E. F. and Maniatis, T., Cold Spring Harbor Laboratory Press, 1989) or the methods described in other experimental manuals used by those skilled in the art, or using commercially available reagents or kits according to the instruction manuals, unless otherwise specified.

Example 1

Preparation of a Rat Anti-Human FGFR2 Antibody

1)-1 Immunization

Female WKY/Izm rats (Japan SLC, Inc.) were used in immunization. A mixture of an antigenic protein Recombinant Human FGFR2β (IIIc)/Fc Chimera (manufactured by R&D Systems, Inc.) and Freund's Complete Adjuvant (manufactured by Wako Pure Chemicals Industries, Ltd.) was administered to the tail base of each WKY/Izm rat. The lymph node and the spleen were collected from the rat and used in hybridoma preparation.

1)-2 Hybridoma Preparation

The lymph node cells or the spleen cells were electrically fused with mouse myeloma SP2/0-Ag14 cells (ATCC: CRL-1581) using LF301-Cell Fusion Unit (manufactured by BEX Co., Ltd.). The fused cells were diluted with ClonaCell-HY Selection Medium D (manufactured by StemCell Technologies Inc.) and cultured. Hybridoma colonies that appeared were recovered to prepare monoclonal hybridomas. Each hybridoma colony thus recovered was cultured, and the obtained hybridoma culture supernatant was used to screen for an anti-FGFR2 antibody-producing hybridoma.

1)-3 Construction of an Expression Vector for Screening for Antigen-Binding Antibody 1)-3-1 Construction of Human FGFR2 IIIb and FGFR2 IIIc Expression Vectors (pcDNA-DEST40-FGFR2 IIIb and pcDNA-DEST40-FGFR2 IIIc)

cDNAs encoding a human FGFR2 IIIb variant protein (amino acid sequence of positions 1 to 822 of isoform 2(NP_075259)) and a human FGFR2 IIIc variant protein (amino acid sequence of positions 1 to 821 of isoform 1(NP_000132)) were cloned into pcDNA-DEST40 vectors to construct vectors pcDNA-DEST40-FGFR2 IIIb and pcDNA-DEST40-FGFR2 IIIc for expression of each variant protein, respectively.

1)-3-2 Construction of Human FGFR1 IIIc, Human FGFR3 IIIb, Human FGFR3 IIIc, and Human FGFR4 Expression Vectors cDNAs encoding a human FGFR1 IIIc variant protein (amino acid sequence of positions 1 to 822 of isoform 1 (NP_075598)), a human FGFR3 IIIb variant protein (amino acid sequence of positions 1 to 808 of isoform 3 (NP_001156685)), a human FGFR3 IIIc variant protein (amino acid sequence of positions 1 to 806 of isoform 1 (NP_000133)), and a human FGFR4 protein (amino acid sequence of positions 1 to 802 of isoform 1 (NP_002002)) were cloned into pcDNA-DEST40 vectors to construct vectors pcDNA-DEST40-FGFR1 IIIc, pcDNA-DEST40-FGFR3 IIIb, pcDNA-DEST40-FGFR3 IIIc, and pcDNA-DEST40-FGFR4 for expression of each variant protein, respectively.

1)-3-3 Construction of a Human FGFR1 IIIb Expression Vector (pcDNA-DEST40-FGFR1 IIIb)

A cDNA encoding a human FGFR1 IIIb variant protein (protein comprising the amino acid sequence of the FGFR1 IIIb domain (AAB19502) between an amino acid sequence of positions 1 to 310 and an amino acid sequence of positions 359 to 820 of isoform 2 (NP_056934)) was cloned into a pcDNA-DEST40 vector to construct pcDNA-DEST40-FGFR1 IIIb.

1)-4 Antibody Screening by Cell-ELISA

1)-4-1 Preparation of an Antigen Gene-Expressing Cell for Cell-ELISA

HEK293 cells were adjusted to $7.5 \times 10^5$ cells/ml in a DMEM medium containing 10% FBS. pcDNA-DEST40-FGFR2 IIIc or a control pcDNA-DEST40 was transfected thereto using Lipofectamine 2000 (manufactured by Life Technologies Corp.). The resulting cells were dispensed in an amount of 50 µl/well to a 96-well half area plate (manufactured by Corning Inc.) and cultured overnight at 37° C. under 5% $CO_2$ conditions in a DMEM medium containing 10% FBS. The obtained transfected cells were used in the attached state in Cell-ELISA.

1)-4-2 Cell-ELISA

After removal of the culture supernatant from the expression vector-transfected HEK293 cells prepared in Example 1)-4-1, each hybridoma culture supernatant was added to the pcDNA-DEST40-FGFR2 IIIc- or pcDNA-DEST40-transfected HEK293 cells, and the plate was left standing at 4° C. for 1 hour. The cells in the wells were washed once with PBS containing 5% FBS. Then, Anti-Rat IgG-Peroxidase antibody produced in rabbit (manufactured by Sigma-Aldrich Corp.) diluted 500-fold with PBS containing 5% FBS was added thereto, and the plate was left standing at 4° C. for 1 hour. The cells in the wells were washed 6 times with PBS containing 5% FBS. Then, an OPD chromogenic solution (OPD solution (o-phenylenediamine dihydrochloride (manufactured by Wako Pure Chemicals Industries, Ltd.) and $H_2O_2$ dissolved at concentrations of 0.4 mg/ml and 0.6% (v/v), respectively, in 0.05 M trisodium citrate and 0.1 M disodium hydrogen phosphate dodecahydrate, pH 4.5)) was added thereto at a concentration of 25 µl/well. Color reaction was performed with occasional stirring and stopped by the addition of 1 M HCl at a concentration of 25 µl/well. Then, the absorbance was measured at 490 nm using a plate reader (ENVISION; PerkinElmer, Inc.). In order to select a hybridoma producing an antibody specifically binding to FGFR2 expressed on cell membrane surface, hybridomas that yielded a culture supernatant exhibiting higher absorbance for the pcDNA-DEST40-FGFR2 IIIc expression vector-transfected HEK293 cells compared with the control pcDNA-DEST40-transfected HEK293 cells were selected as anti-FGFR2 antibody production-positive hybridomas.

1)-5 Antibody Screening by Flow Cytometry

1)-5-1 Preparation of an Antigen Gene-Expressing Cell for Flow Cytometry Analysis HEK293T cells were inoculated at a density of $5 \times 10^4$ cells/cm$^2$ to a 225-cm$^2$ flask (manufactured by Sumitomo Bakelite Co., Ltd.) and cultured overnight at 37° C. under 5% $CO_2$ conditions in a DMEM medium containing 10% FBS. On the next day, the pcDNA-DEST40-FGFR2 IIIc, the pcDNA-DEST40-FGFR2 IIIb or a control pcDNA-DEST40 was transfected to the HEK293T cells using Lipofectamine 2000, and the cells were further cultured overnight at 37° C. under 5% $CO_2$ conditions. On the next day, the expression vector-transfected HEK293T cells were treated with TrypLE Express (manufactured by Life Technologies Corp.), washed with DMEM containing 10% FBS, and then suspended in PBS containing 5% FBS. The obtained cell suspension was used in flow cytometry analysis.

1)-5-2 Flow Cytometry Analysis

The pcDNA-DEST40-FGFR2 IIIc and pcDNA-DEST40-FGFR2 IIIb binding specificity of the antibody produced by each hybridoma determined to be positive by Cell-ELISA in Example 1)-4 was further confirmed by flow cytometry. Each HEK293T cell suspension prepared in Example 1)-5-1 was centrifuged to remove a supernatant. Then, the pcDNA-DEST40-FGFR2 IIIc-transfected HEK293T cells, the pcDNA-DEST40-FGFR2 IIIb-transfected HEK293T cells, or the pcDNA-DEST40-transfected HEK293T cells were suspended by the addition of the hybridoma culture supernatant and left standing at 4° C. for 1 hour. The cells were washed once with PBS containing 5% FBS, then suspended by the addition of Anti-Rat IgG FITC conjugate (manufactured by Sigma-Aldrich Corp.) diluted 500-fold with PBS containing 5% FBS, and left standing at 4° C. for 1 hour. The cells were washed 3 times with PBS containing 5% FBS and then resuspended in PBS containing 5% FBS and 2 µg/ml 7-aminoactinomycin D (manufactured by Molecular Probes, Inc.), followed by detection using a flow cytometer (FC500; manufactured by Beckman Coulter Inc.). The data was analyzed using Flowjo (manufactured by Tree Star Inc.). After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the pcDNA-DEST40-FGFR2 IIIc- or pcDNA-DEST40-FGFR2 IIIb-transfected HEK293T cells compared with the fluorescence intensity histogram of the control pcDNA-DEST40-transfected HEK293T cells were selected such that rat FR2-2nd_#028 was obtained as a hybridoma producing an antibody specifically binding to FGFR2 IIIc and rat FR2-2nd_#023 was obtained as a hybridoma producing an antibody binding to both FGFR2 IIIb and FGFR2 IIIc.

1)-6 Isotyping of the Antibody

The rat FR2-2nd_#028 and FR2-2nd_#023 produced by the anti-FGFR2 antibody-producing hybridomas were isotyped using Rat monoclonal isotyping test kit (manufactured by AbD Serotec). As a result, their isotypes were confirmed to be IgG2b and κ chains for the rat FR2-2nd_#028 and IgG1 and κ chains for the rat FR2-2nd_#023.

1)-7 Preparation of a Monoclonal Antibody

Each rat anti-human FGFR2 monoclonal antibody was purified from the hybridoma culture supernatant.

First, the hybridoma producing the FR2-2nd_#023 or the FR2-2nd_#028 antibody was grown into a sufficient amount with ClonaCell-HY Selection Medium E. Then, the medium was replaced with Hybridoma SFM (Life Technologies Corp.) supplemented with 20% of Ultra Low IgG FBS (Life Technologies Corp.), followed by culture for 7 days. This culture supernatant was recovered and sterilized through a 0.45-μm filter.

The antibody was purified using Hitrap protein G HP (manufactured by GE Healthcare Bio-Sciences Corp.) according to the description of the attached manual. The recovered culture supernatant was added to a column, which was then washed with a binding buffer (0.02 M sodium phosphate (pH 7.0)), followed by elution with 0.1 M glycine (pH 2.7). The eluted antibody solution was neutralized, then buffer-replaced with PBS using PD-10 SX G-25(M) 30ST column (manufactured by GE Healthcare Bio-Sciences Corp.), and concentrated using Amicon-Ultra 4 centrifugal filter (Merck Millipore).

The concentration of the antibody was determined by the measurement of absorbance (O.D. 280 nm) using Gene Spec I (manufactured by Hitachi, Ltd.). Specifically, the peak area of the absorbance (O.D. 280 nm) of the antibody solution was measured, and the concentration was calculated according to the following expression: Antibody sample concentration (mg/ml)=(Peak area of the antibody sample)/(Peak area of a standard (human IgG1))×Concentration (mg/ml) of the standard×Dilution ratio of the sample. Also, the concentration of endotoxin contained in the obtained antibody was measured using The Endosafe-PTS Portable Test System (Charles River Laboratories Japan Inc.) and confirmed to be 1 EU/mg or lower. The antibody was used in the subsequent experiments.

Example 2

Cloning of the Rat Antibody FR2-2nd_#028 and the Rat Antibody FR2-2nd_#023

2)-1 Cloning of the Rat Antibody FR2-2nd_#028

2)-1-1 Preparation of Total RNA from the Hybridoma Producing Rat Antibody FR2-2nd_#028

In order to amplify cDNAs encoding the variable regions of the rat antibody FR2-2nd_#028, total RNA was prepared from the hybridoma producing the rat antibody 2nd_#28 using TRIzol Reagent (Ambion/Thermo Fisher Scientific Inc.).

2)-1-2 Synthesis of cDNA (5'-RACE-Ready cDNA)

cDNAs (5'-RACE-Ready cDNAs) were synthesized using 1 μg of the total RNA prepared in Example 2)-1-1 and SMARTer RACE cDNA Amplification Kit (Clontech Laboratories, Inc.).

2)-1-3 5'-RACE PCR Amplification and Sequencing of cDNA Encoding the Heavy Chain Variable Region of the Rat Antibody FR2-2nd_#028

The primers used for PCR amplification of the variable region-encoding cDNA of the heavy chain gene of the rat antibody FR2-2nd_#028 were oligonucleotides having the sequences of UPM (Universal Primer A Mix; attached to SMARTer RACE cDNA Amplification Kit) and 5'-CTCCAGAGTTCCAGGTCACGGTGACTGGC-3' (RG2AR3: SEQ ID NO: 1). The UPM used was attached to SMARTer RACE cDNA Amplification Kit (Clontech Laboratories, Inc.), while RG2AR3 was designed from the sequences of rat heavy chain constant regions in the database.

cDNA encoding the heavy chain variable region of the rat antibody FR2-2nd_#028 was amplified by 5'-RACE PCR using this primer set and the cDNA (5'-RACE-Ready cDNA) synthesized in Example 2)-1-2 as a template. This PCR was carried out on the Touchdown PCR program according to the manual of SMARTer RACE cDNA Amplification Kit (Clontech Laboratories, Inc.) using polymerase KOD-Plus- (Toyobo Co., Ltd.).

The heavy chain variable region-encoding cDNA amplified by 5'-RACE PCR was purified using MinElute PCR Purification Kit (Qiagen N.V.) and then cloned using Zero Blunt TOPO PCR Cloning Kit (Invitrogen Corp.). The cloned heavy chain variable region-encoding cDNA was analyzed by sequencing.

The sequencing primers used an oligonucleotide having the sequence 5'-CTCCAGAGTTCCAGGTCACGGTGACTGGC-3' (RG2AR3: SEQ ID NO: 1) designed from the sequences of rat heavy chain constant regions in the database, and NUP (Nested Universal Primer A; attached to SMARTer RACE cDNA Amplification Kit).

The sequencing analysis was carried out using a gene sequence analyzer ("ABI PRISM 3700 DNA Analyzer; Applied Biosystems, Inc." or "Applied Biosystems 3730x1 Analyzer; Applied Biosystems, Inc."). GeneAmp 9700 (Applied Biosystems, Inc.) was used in sequencing reaction.

The determined nucleotide sequence of the cDNA encoding the heavy chain variable region of the rat antibody FR2-2nd_#028 is shown in SEQ ID NO: 2 (FIG. 14A), and the amino acid sequence thereof is shown in SEQ ID NO: 3 (FIG. 14B).

2)-1-4 5'-RACE PCR Amplification and Sequencing of cDNA Encoding the Light Chain Variable Region of the Rat Antibody FR2-2nd_#028

The primers used for PCR amplification of the variable region-encoding cDNA of the light chain gene of the rat antibody FR2-2nd_#028 were oligonucleotides having the sequences of UPM (Universal Primer A Mix; attached to SMARTer RACE cDNA Amplification Kit) and 5'-TCAGTAACACTGTCCAGGACACCATCTC-3' (RKR5: SEQ ID NO: 4). The UPM used was attached to SMARTer RACE cDNA Amplification Kit (Clontech Laboratories, Inc.), while RKR5 was designed from the sequences of rat light chain constant regions in the database.

cDNA encoding the light chain variable region of the rat antibody FR2-2nd_#028 was amplified by 5'-RACE PCR using this primer set and the cDNA (5'-RACE-Ready cDNA) synthesized in Example 2)-1-2 as a template. This PCR was carried out on the Touchdown PCR program according to the manual of SMARTer RACE cDNA Amplification Kit (Clontech Laboratories, Inc.) using polymerase KOD-Plus- (Toyobo Co., Ltd.).

The light chain variable region-encoding cDNA amplified by 5'-RACE PCR was purified using MinElute PCR Purification Kit (Qiagen N.V.) and then cloned using Zero Blunt TOPO PCR Cloning Kit (Invitrogen Corp.). The cloned light chain variable region-encoding cDNA was analyzed by sequencing.

The sequencing primers used were an oligonucleotide having the sequence 5'-TCAGTAACACTGTCCAGGACACCATCTC-3' (RKR5: SEQ ID NO: 4) designed from the sequences of rat light chain constant regions in the database, and NUP (Nested Universal Primer A; attached to SMARTer RACE cDNA Amplification Kit).

The sequencing analysis was carried out using a gene sequence analyzer ("ABI PRISM 3700 DNA Analyzer; Applied Biosystems, Inc." or "Applied Biosystems 3730x1 Analyzer; Applied Biosystems, Inc."). GeneAmp 9700 (Applied Biosystems, Inc.) was used in sequencing reaction.

The determined nucleotide sequence of the cDNA encoding the light chain variable region of the rat antibody FR2-2nd_#028 is shown in SEQ ID NO: 5 (FIG. 14C), and the amino acid sequence thereof is shown in SEQ ID NO: 6 (FIG. 14D).

2)-2 Cloning of the Rat Antibody FR2-2nd_#023

2)-2-1 Preparation of Total RNA from the Hybridoma Producing the Rat Antibody FR2-2nd_#023

In order to amplify cDNAs encoding the variable regions of the rat antibody FR2-2nd_#023, total RNA was prepared from the hybridoma producing the rat antibody 2nd_#023 in the same way as in Example 2)-1-1.

2)-2-2 Synthesis of cDNA (5'-RACE-Ready cDNA)

cDNAs (5'-RACE-Ready cDNAs) were synthesized in the same way as in Example 2)-1-2 using 1 μg of the total RNA prepared in Example 2)-2-1.

2)-2-3 5'-RACE PCR Amplification and Sequencing of cDNA Encoding the Heavy Chain Variable Region of the Rat Antibody FR2-2nd_#023 cDNA encoding the heavy chain variable region of the rat antibody FR2-2nd_#023 was amplified using the cDNA (5'-RACE-Ready cDNA) synthesized in Example 2)-2-2 as a template, and sequenced, in the same way as in Example 2)-1-3.

The determined nucleotide sequence of the cDNA encoding the heavy chain variable region of the rat antibody FR2-2nd_#023 is shown in SEQ ID NO: 7 (FIG. 15A), and the amino acid sequence thereof is shown in SEQ ID NO: 8 (FIG. 15B).

2)-2-4 5'-RACE PCR Amplification and Sequencing of cDNA Encoding the Light Chain Variable Region of the Rat Antibody FR2-2nd_#023 cDNA encoding the light chain variable region of the rat antibody FR2-2nd_#023 was amplified using the cDNA (5'-RACE-Ready cDNA) synthesized in Example 2)-2-2 as a template, and sequenced, in the same way as in Example 2)-1-4.

The determined nucleotide sequence of the cDNA encoding the light chain variable region of the rat antibody FR2-2nd_#023 is shown in SEQ ID NO: 9 (FIG. 15C), and the amino acid sequence thereof is shown in SEQ ID NO: 10 (FIG. 15D).

Example 3

Preparation of the Mouse IgG1 Chimeric FR2-2nd_#028 and Mouse IgG1 Chimeric FR2-2nd_#023

3)-1 Construction of the Expression Vector pCMA-LK

A plasmid pcDNA3.3-TOPO/LacZ (Invitrogen Corp.) was digested with restriction enzymes XbaI and PmeI. The obtained fragment of approximately 5.4 kb was ligated with a DNA fragment comprising a nucleotide sequence (shown in SEQ ID NO: 11 (FIG. 16)) encoding a human κ chain secretory signal and a human κ chain constant region using In-Fusion Advantage PCR cloning kit (Clontech Laboratories, Inc.) to prepare pcDNA3.3/LK.

PCR was performed with pcDNA3.3/LK as a template using a primer set shown below. The obtained fragment of approximately 3.8 kb was phosphorylated and then self-ligated to construct an expression vector pCMA-LK having a signal sequence and the nucleotide sequence encoding the human κ chain constant region, downstream of the CMV promoter.

```
Primer set
                                  (3.3-F1: SEQ ID NO: 12)
   5'-TATACCGTCGACCTCTAGCTAGAGCTTGGC-3'

(3.3-R1: SEQ ID NO: 13)
   5'-GCTATGGCAGGGCCTGCCGCCCCGACGTTG-3'
```

3)-2 Construction of the Mouse Chimeric FR2-2nd_#028 Heavy Chain Expression Vector A DNA fragment comprising a nucleotide sequence (shown in SEQ ID NO: 14) encoding the heavy chain of mouse chimeric FR2-2nd_#028 was synthesized (GeneScript Gene Synthesis Service). The DNA fragment comprising a nucleotide sequence encoding the heavy chain of mouse chimeric FR2-2nd_#028 was amplified using the synthesized DNA fragment as a template, KOD-Plus- (Toyobo Co., Ltd.), and a primer set shown below, and inserted to the site from which the DNA sequence encoding the κ chain secretory signal and the human κ chain constant region was removed by the digestion of the expression vector pCMA-LK with restriction enzymes XbaI and PmeI, using In-Fusion HD PCR cloning kit (Clontech Laboratories, Inc.) to construct a chimeric 2nd_#028 heavy chain expression vector. The obtained expression vector was designated as "pCMA/2nd_#28H".

```
Primer set
                                  (CM-inf-F: SEQ ID NO: 16)
   5'-CCAGCCTCCGGACTCTAGAGCCACC-3'

(CM-inf-R: SEQ ID NO: 17)
   5'-AGTTAGCCTCCCCCGTTTAAACTC-3'
```

The amino acid sequence of the heavy chain of the mouse chimeric FR2-2nd_#028 is shown in SEQ ID NO: 15.

3)-3 Construction of the Mouse Chimeric 2nd_#028 Light Chain Expression Vector

A DNA fragment comprising a nucleotide sequence (shown in SEQ ID NO: 18) encoding the light chain of the mouse chimeric FR2-2nd_#028 was synthesized (GeneScript Artificial Gene Synthesis Service). A chimeric 2nd_#28 light chain expression vector was constructed in the same way as in Example 3)-2. The obtained expression vector was designated as "pCMA/2nd_#28L".

The amino acid sequence of the light chain of the mouse chimeric FR2-2nd_#028 is shown in SEQ ID NO: 19.

3)-4 Construction of the Mouse Chimeric 2nd_#023 Heavy Chain Expression Vector

A DNA fragment comprising a nucleotide sequence (shown in SEQ ID NO: 20) encoding the heavy chain of mouse chimeric FR2-2nd_#023 was synthesized (GeneScript Artificial Gene Synthesis Service). A mouse chimeric 2nd_#023 heavy chain expression vector was constructed in the same way as in Example 3)-2. The obtained expression vector was designated as "pCMA/2nd_#23H".

The amino acid sequence of the heavy chain of the mouse chimeric FR2-2nd_#023 is shown in SEQ ID NO: 21.

3)-5 Construction of the Mouse Chimeric 2nd_#023 Light Chain Expression Vector

A DNA fragment comprising a sequence (shown in SEQ ID NO: 22) encoding the light chain of the mouse chimeric FR2-2nd_#023 was synthesized (GeneScript Artificial Gene Synthesis Service). A mouse chimeric 2nd_#023 light chain expression vector was constructed in the same way as in Example 3)-2. The obtained expression vector was designated as "pCMA/2nd_#23L".

The amino acid sequence of the light chain of the mouse chimeric FR2-2nd_#023 is shown in SEQ ID NO: 23.

3)-6 Production of the Mouse Chimeric FR2-2nd_#028 and Mouse Chimeric FR2-2nd_#023

FreeStyle 293F cells (Invitrogen Corp.) were subcultured and cultured according to the manual. $1.2 \times 10^9$ FreeStyle 293F cells (Invitrogen Corp.) in the logarithmic growth phase were inoculated to a 3-L Fernbach Erlenmeyer Flask (Corning Inc.), adjusted to $2.0 \times 10^6$ cells/ml by dilution with FreeStyle 293 expression medium (Invitrogen Corp.), and then shake-cultured at 90 rpm at 37° C. for 1 hour in an 8% $CO_2$ incubator. 1.8 mg of polyethyleneimine (Polysciences #24765) was dissolved in 20 ml of Opti-Pro SFM medium (Invitrogen Corp.). Next, each H chain expression vector (0.24 mg) and each L chain expression vector (0.36 mg) prepared using NucleoBond Xtra (Takara Bio Inc.) were added to 20 ml of Opti-Pro SFM medium (Invitrogen Corp.). 20 ml of the expression vector/Opti-Pro SFM mixed solution was added to 20 ml of the polyethyleneimine/Opti-Pro SFM mixed solution, and the mixture was gently stirred, left for 5 minutes, and then added to the FreeStyle 293F cells. The cells were shake-cultured at 90 rpm at 37° C. for 4 hours in an 8% $CO_2$ incubator. Then, 600 ml of EX-CELL VPRO medium (SAFC Biosciences), 18 ml of GlutaMAX I (GIBCO/Thermo Fisher Scientific Inc.), and 30 ml of Yeastolate Ultrafiltrate (GIBCO/Thermo Fisher Scientific Inc.) were added thereto. The cells were shake-cultured at 90 rpm at 37° C. for 7 days in an 8% $CO_2$ incubator, and the obtained culture supernatant was filtered through Disposable Capsule Filter (Advantec #CCS-045-E1H).

The chimeric antibody of the rat antibody FR2-2nd_#028 obtained by the combination of pCMA/2nd_#28H and pCMA/2nd_#28L was designated as "mouse chimeric FR2-2nd_#028", and the chimeric antibody of the rat antibody FR2-2nd_#023 obtained by the combination of pCMA/2nd_#23H and pCMA/2nd_#23L was designated as "mouse chimeric FR2-2nd_#023".

3)-7 Purification of the Mouse Chimeric FR2-2nd_#023 and Mouse Chimeric FR2-2nd_#028

Each culture supernatant obtained in Example 3)-6 was purified by one step using rProtein A affinity chromatography (at 4 to 6° C.). A buffer replacement step after the rProtein A affinity chromatography purification was carried out at 4 to 6° C. First, the culture supernatant was applied to MabSelect SuRe (GE Healthcare Bio-Sciences Corp.) equilibrated with PBS. After entry of the whole culture solution into the column, the column was washed with PBS in an amount at least twice the column volume. Next, antibody-containing fractions were collected by elution with a 2 M arginine hydrochloride solution (pH 4.0). The fractions were buffer-replaced with HBSor (25 mM histidine and 5% sorbitol, pH 6.0) by dialysis (Thermo Fisher Scientific Inc., Slide-A-Lyzer Dialysis Cassette). The fractions were concentrated and adjusted to an IgG concentration of 5 mg/ml using Centrifugal UF Filter Device VIVASPIN 20 (molecular weight cutoff: UF10K, Sartorius Japan K.K., at 4° C.). Finally, the concentrate was filtered through Minisart-Plus filter (Sartorius Japan K.K.) and used as a purified sample.

3)-8 Analysis of the Mouse Chimeric FR2-2nd_#028 and Mouse Chimeric FR2-2nd_#028 for Binding to Each Molecule of FGFR Family by Flow Cytometry Analysis 3)-8-1 Preparation of an Antigen Gene-Expressing Cell for Flow Cytometry Analysis HEK293T cells were adjusted to $7.5 \times 10^5$ cells/ml in a DMEM medium containing 10% FBS. The cells were transfected with the FGFR1 IIIb, FGFR1 IIIc, FGFR2 IIIb, FGFR2 IIIc, FGFR3 IIIb, FGFR3 IIIc, or FGFR4 expression vector constructed in Examples 1)-3-1, 1)-3-2, and 1)-3-3 or an empty vector, i.e., pcDNA-DEST40-FGFR1 IIIb, pcDNA-DEST40-FGFR1 IIIc, pcDNA-DEST40-FGFR2 IIIb, pcDNA-DEST40-FGFR2 IIIc, pcDNA-DEST40-FGFR3 IIIb, pcDNA-DEST40-FGFR3 IIIc, pcDNA-DEST40-FGFR4, or pcDNA-DEST40, using Lipofectamine 2000 (manufactured by Life Technologies Corp.) and cultured at 37° C. under 5% $CO_2$ conditions in a DMEM medium containing 10% FBS. On the next day, the expression vector-transfected HEK293T cells were treated with TrypLE Express (manufactured by Life Technologies Corp.), washed with DMEM containing 10% FBS, and then suspended in PBS containing 5% FBS. The obtained cell suspension was used in flow cytometry analysis.

3)-8-2

The binding specificity of the mouse chimeric FR2-2nd_#028 and the mouse chimeric FR2-2nd_#023 prepared in Example 3)-7 for non-denatured molecules of the FGFR family was confirmed by flow cytometry. Each HEK293T cell suspension prepared in Example 3)-8-1 was centrifuged to remove a supernatant. Then, the pcDNA-DEST40-FGFR1 IIIb-, pcDNA-DEST40-FGFR1 IIIc-, pcDNA-DEST40-FGFR2 IIIb-, pcDNA-DEST40-FGFR2 IIIc-, pcDNA-DEST40-FGFR3 IIIb-, pcDNA-DEST40-FGFR3 IIIc-, pcDNA-DEST40-FGFR4-, or pcDNA-DEST40-transfected HEK293T cells were suspended by the addition of a negative control mouse IgG1 (manufactured by R&D Systems, Inc.) or the mouse chimeric FR2-2nd_#028 or the mouse chimeric FR2-2nd_#023 adjusted to 5 μg/ml, and left standing at 4° C. for 1 hour. The cells were washed once with PBS containing 5% FBS, then suspended by the addition of Fluorescein-Conjugated Goat IgG Fraction to Mouse IgG (manufactured by MP Biomedicals, Inc.) diluted 500-fold with PBS containing 5% FBS, and left standing at 4° C. for 1 hour. The cells were washed 3 times with PBS containing 5% FBS and then resuspended in PBS containing 5% FBS and 2 μg/ml 7-aminoactinomycin D (manufactured by Molecular Probes, Inc.), followed by detection using a flow cytometer (FC500; manufactured by Beckman Coulter Inc.). The data was analyzed using Flowjo (manufactured by Tree Star Inc.). After removal of 7-aminoactinomycin D-positive dead cells by gating, the average fluorescence intensity (MFI) of the FITC of live cells was calculated (FIG. 1). As compared with the fluorescence intensity histogram of the control pcDNA-DEST40-transfected HEK293T cells, the mouse chimeric FR2-2nd_#028 exhibited specific binding to the FGFR2 IIIc-expressing HEK293T cells and no binding to the HEK293T cells expressing FGFR2 IIIb or the other members of the FGFR family. Also, FR2-2nd_#023 exhibited specific binding to the FGFR2 IIIb- or FGFR2 IIIc-expressing HEK293T cells and no binding to the HEK293T cells expressing the other members of the FGFR family.

Example 4

Immunostaining

4)-1 Preparation of a Sample for Immunostaining

4)-1-1 Preparation of a Cell Line Expressing Each Molecule of FGFR Family

Cell line 293α cells, which were HEK293 cells stably transfected with integrin av and integrin β3 expression vectors, were adjusted to $6\times10^6$ cells/225-cm$^2$ flask (manufactured by Sumitomo Bakelite Co., Ltd.) in a DMEM medium containing 10% FBS and cultured overnight at 37° C. under 5% $CO_2$ conditions. The cells were transfected with the FGFR1 IIIb, FGFR1 IIIc, FGFR2 IIIb, FGFR2 IIIc, FGFR3 IIIb, FGFR3 IIIc, or FGFR4 expression vector constructed in Examples 1)-3-1, 1)-3-2, and 1)-3-3 or an empty vector, i.e., pcDNA-DEST40-FGFR1 IIIb, pcDNA-DEST40-FGFR1 IIIc, pcDNA-DEST40-FGFR2 IIIb, pcDNA-DEST40-FGFR2 IIIc, pcDNA-DEST40-FGFR3 IIIb, pcDNA-DEST40-FGFR3 IIIc, pcDNA-DEST40-FGFR4, or pcDNA-DEST40 using FuGENE 6 (manufactured by Roche Diagnostics K.K.) and cultured for two nights at 37° C. under 5% $CO_2$ conditions. The obtained cells were recovered using TrypLE Express (manufactured by Life Technologies Corp.) and centrifuged to obtain a pellet, which was then washed once with PBS and centrifuged. The resulting pellet was fixed in 20% neutral buffered formalin.

4)-1-2 Preparation of a FGFR2-Expressing Cancer Cell Line

A human stomach cancer line SNU-16 and a human colorectal cancer line NCI-H716 (purchased from ATCC) cultured in RPMI containing 10% FBS were each recovered and centrifuged to obtain a pellet, which was then fixed in 20% neutral buffered formalin. A human stomach cancer line KATO III (purchased from ATCC) cultured in DMEM containing 10% FBS was recovered and centrifuged to obtain a pellet, which was then fixed in 20% neutral buffered formalin.

4)-1-3 Preparation of a Tumor Sample of a FGFR2-Expressing Cancer Cell Line Xenograft Model $5\times10^6$ cells of SNU-16 were suspended in 50% Matrigel (manufactured by Nippon Becton Dickinson Company, Ltd.) and subcutaneously transplanted to the axillary region of each nude mice (CAnN.Cg-Foxnl$^{nu}$/CrlCrlj, purchased from Charles River Laboratories Japan Inc.). Twenty days after transplantation, tumor was recovered and fixed in Mildform (manufactured by Wako Pure Chemicals Industries, Ltd.).

$3\times10^5$ cells of KATO III were suspended in 100% Matrigel (manufactured by Nippon Becton Dickinson Company, Ltd.) and subcutaneously transplanted to the axillary region of each SCID mouse (CB17/lcr-Prkdc$^{scid}$/CrlCrlj, purchased from Charles River Laboratories Japan Inc.). Thirty days after transplantation, tumor was recovered and fixed in Mildform (manufactured by Wako Pure Chemicals Industries, Ltd.).

$2.5\times10^6$ cells of NCI-H716 were suspended in 100% Matrigel (manufactured by Nippon Becton Dickinson Company, Ltd.) and subcutaneously transplanted to the axillary region of each nude mice (CAnN.Cg-Foxnl$^{nu}$/CrlCrlj, purchased from Charles River Laboratories Japan Inc.). Twenty-one days after transplantation, tumor was recovered and fixed in Mildform (manufactured by Wako Pure Chemicals Industries, Ltd.).

4)-2 Paraffin Embedding and Sectioning

Paraffin embedding and sectioning are general approaches, and any tool or instrument can be used without particular limitations.

The cells of each line prepared in Examples 4)-1-1 and 4)-1-2 were recovered into a 15-mL tube and centrifuged at 1500 rpm for 5 minutes to remove a supernatant. 3 mL of 20% neutral buffered formalin (manufactured by Wako Pure Chemicals Industries, Ltd.) was layered over the cell pellet and left standing at room temperature for 30 minutes or longer for fixation. Then, 5 mL of chloroform was added thereto. Immediately thereafter, the tube was centrifuged at 1000 rpm for 10 minutes, and the formalin layer was immediately removed. Then, the cell pellet formed between the formalin layer and the chloroform layer was recovered. The cell pellet was put in a nylon mesh bag, which was then placed in a cassette for tissue preparation (Unicassette Standard, manufactured by Sakura Finetek Japan Co., Ltd.). The cell pellet, together with the cassette, was dipped in ethanol to wash off the chloroform. Each xenograft tissue prepared in Example 4)-1-3 was fixed in Mildform (purchased from Wako Pure Chemicals Industries, Ltd.), then trimmed at the cutout portion, and placed in a cassette.

The cell pellet and the xenograft tissue were paraffin-embedded by a conventional method.

Dehydration, delipidation, and paraffin impregnation were performed using an automatic fixation and embedding apparatus (Tissue-Tek VIP5 Jr.; manufactured by Sakura Finetek Japan Co., Ltd.). The cassette was taken out of the automatic fixation and embedding apparatus and transferred to the paraffin bath of a paraffin-embedded block preparation apparatus (Tissue-Tek TEC Plus; manufactured by Sakura Finetek Japan Co., Ltd.). A small amount of melted paraffin was injected into an embedding dish loaded to this apparatus. The cell pellet or the tissue was separated with tweezers from the cassette container or the nylon mesh taken out of the paraffin bath, and loaded into the paraffin in this embedding dish. Subsequently, a cassette was placed as an embedding frame on the embedding dish, and melted paraffin was poured over the cell pellet or the tissue within the cassette. The embedding dish containing the embedding frame integrated with the cells or the tissue was placed on a cooling unit and cooled. After solidification of paraffin, the embedded block was taken out of the embedding dish and subjected to sectioning. The sectioning was performed by the slicing of the embedded block thus prepared into sections with a thickness of 3 μm using a microtome (IVS-410; manufactured by Sakura Finetek Japan Co., Ltd.). Each section thus obtained was applied to an antistripping glass slide (Platinum; manufactured by Matsunami Glass Ind., Ltd.). The glass slide was dried overnight on a paraffin stretcher (manufactured by Sakura Finetek Japan Co., Ltd.) at 50° C., accommodated in a slide case, and stored in a desiccator.

4)-3 Staining

4)-3-1 Staining Using Commercially Available Antibody 18601 (Anti-Human K-Sam Rabbit IgG Affinity Purify, Manufactured by Immuno-Biological Laboratories Co., Ltd.)

Each sample was stained using an automatic staining apparatus (Discovery Ultra; manufactured by Ventana Medical Systems, Inc.). The reaction temperature during the staining process was set to 37° C., unless otherwise specified. The sample was deparaffinized by 3 incubation runs each involving 68° C. for 4 minutes using fresh EZ buffer (manufactured by Ventana Medical Systems, Inc.), and then washed with EZ buffer. Antigen retrieval was carried out by 4 runs each involving 95° C. using fresh CC1 buffer (manufactured by Ventana Medical Systems, Inc.) for a total of 52 minutes. The sample was washed 4 times with a reaction buffer (manufactured by Ventana Medical Systems, Inc.). Protein Block serum free (manufactured by DAKO/Agilent Technologies, Inc.) was added thereto, and the sample was incubated for 16 minutes and washed 3 times with a reaction buffer. 18601 was diluted to 5 µg/mL with an antibody diluent dedicated to Discovery (manufactured by Ventana Medical Systems, Inc.), and reacted with the sample for 1 hour. After washing 3 times with a reaction buffer, Inhibitor CM (ChromoMap kit; manufactured by Ventana Medical Systems, Inc.) was reacted therewith for 8 minutes, and the sample was then washed twice with a reaction buffer. UMap anti-Rb HRP (manufactured by Ventana Medical Systems, Inc.) was reacted therewith for 32 minutes, and the sample was washed 4 times with a reaction buffer. DAB CM (ChromoMap kit; manufactured by Ventana Medical Systems, Inc.) was reacted therewith for 4 minutes. Then, H2O2CM (ChromoMap kit; manufactured by Ventana Medical Systems, Inc.) was added thereto, followed by reaction with 8 minutes. The sample was washed once with a reaction buffer. Copper-CM (ChromoMap kit; manufactured by Ventana Medical Systems, Inc.) was reacted therewith for 4 minutes, and the sample was washed once with a reaction buffer. Hematoxylin II counter stain reagent (manufactured by Ventana Medical Systems, Inc.) was reacted therewith for 4 minutes, and the sample was washed twice with a reaction buffer. Bluing Reagent (lithium carbonate reagent, manufactured by Ventana Medical Systems, Inc.) was reacted therewith for 4 minutes, and the sample was washed once with a reaction buffer.

4)-3-2 Staining Using Rat FR2-2nd_#028 Antibody

Each sample was deparaffinized according to a standard method by passing the sample through 4 baths of 100% xylene and 3 baths of 100% ethanol for 5 minutes each, followed by washing with ion-exchanged water. Then, the sample was stained using an automatic staining apparatus (Dako Autostainer Link 48; manufactured by DAKO/Agilent Technologies, Inc.). After washing once with EnVision FLEX WASH BUFFER (manufactured by DAKO/Agilent Technologies, Inc.), the sample was incubated with DAKO Proteinase K RTU (manufactured by DAKO/Agilent Technologies, Inc.) at room temperature for 6 minutes and washed three times with EnVision FLEX WASH BUFFER. Peroxidase Block 3% H2O2 (manufactured by DAKO/Agilent Technologies, Inc.) was added thereto, and the sample was incubated for 5 minutes and washed twice with EnVision FLEX WASH BUFFER. Protein Block serum free (manufactured by DAKO/Agilent Technologies, Inc.) was added thereto, and the sample was incubated for 30 minutes and washed once with EnVision FLEX WASH BUFFER. The rat FR2-2nd_#028 was diluted to 15 µg/mL with DAKO REAL Antibody Diluent and reacted with the sample for 1 hour. After washing 3 times with EnVision FLEX WASH BUFFER, Histofine simple stain mouse MAX-PRO (Rat) #414311 (manufactured by Nichirei Biosciences Inc.) was added thereto, and the sample was incubated for 30 minutes and then washed twice with EnVision FLEX WASH BUFFER.

DAKO Liquid DAB+Substrate Chromogen System was added thereto, and the sample was incubated for a total of 10 minutes and then washed once with EnVision FLEX WASH BUFFER. EnVision FLEX Hematoxylin was added thereto, and the sample was incubated for 5 minutes and then washed a total of 3 times with EnVision FLEX WASH BUFFER and ion-exchanged water.

4)-3-3 Staining Using Mouse Chimeric FR2-2nd_#028 Antibody

Each sample was stained using an automatic staining apparatus (LEICA BOND-III; manufactured by Leica Biosystems Nussloch GmbH). For deparaffinization, the sample was heated to 72° C., then Bond Dewax Solution (manufactured by Leica Biosystems Nussloch GmbH) was added thereto, and the sample was incubated for 30 seconds, followed by addition of ethanol and washing 4 times with Bond Wash Solution (manufactured by Leica Biosystems Nussloch GmbH). Enzyme Proteinase K (IHC) (manufactured by Leica Biosystems Nussloch GmbH) diluted 200-fold was added thereto, and the sample was incubated at 37° C. for 5 minutes. The sample was washed 7 times with Bond Wash Solution. The mouse chimeric FR2-2nd_#028 was diluted to 15 µg/mL and reacted with the sample for 30 minutes.

The sample was washed 3 times with Bond Wash Solution. Post Primary reagent (Bond Polymer System/Leica IHC Refine kit, manufactured by Leica Biosystems Nussloch GmbH) was added thereto, and the sample was incubated for 8 minutes.

The sample was washed 4 times with Bond Wash Solution. Primary reagent (Bond Polymer System/Leica IHC Refine kit, manufactured by Leica Biosystems Nussloch GmbH) was added thereto, and the sample was incubated for 8 minutes. The sample was washed 4 times with Bond Wash Solution. Peroxide Block reagent (Bond Polymer System/Leica IHC Refine kit, manufactured by Leica Biosystems Nussloch GmbH) was added thereto, and the sample was incubated for 5 minutes. The sample was washed a total of 4 times with Bond Wash Solution and ion-exchanged water. DAB reagent (Bond Polymer System/Leica IHC Refine kit, manufactured by Leica Biosystems Nussloch GmbH) was added thereto, and the sample was incubated for 10 minutes. The sample was washed 4 times with ion-exchanged water. Hematoxylin (Bond Polymer System/Leica IHC Refine kit, manufactured by Leica Biosystems Nussloch GmbH) was added thereto, and the sample was incubated for 5 minutes and then washed a total of 4 times with ion-exchanged water and Bond Wash Solution.

4)-3-4 Staining Using Rat FR2-2nd_#023 or Mouse Chimeric FR2-2nd_#023 Antibodies Each sample was stained using an automatic staining apparatus (LEICA BOND-III; manufactured by Leica Biosystems Nussloch GmbH). For deparaffinization, the sample was heated to 72° C., then Bond Dewax Solution (manufactured by Leica Biosystems Nussloch GmbH) was added thereto, and the sample was incubated for 30 seconds, followed by addition of ethanol and washing 4 times with Bond Wash Solution (manufactured by Leica Biosystems Nussloch GmbH). Bond Epitope Retrieval Solution 2 (manufactured by Leica Biosystems Nussloch GmbH) was added thereto, and the sample was incubated at 100° C. for 20 minutes (rat FR2-2nd_#023) or 40 minutes (mouse chimeric FR2-2nd_#023). The sample was washed 7 times with Bond Wash Solution. Each antibody was diluted to 15 μg/mL and reacted with the sample for 30 minutes.

The sample was washed 3 times with Bond Wash Solution. Post Primary reagent (Bond Polymer System/Leica IHC Refine kit, manufactured by Leica Biosystems Nussloch GmbH) was added thereto, and the sample was incubated for 8 minutes.

The sample was washed 4 times with Bond Wash Solution. Primary reagent (Bond Polymer System/Leica IHC Refine kit, manufactured by Leica Biosystems Nussloch GmbH) was added thereto, and the sample was incubated for 8 minutes. The sample was washed 4 times with Bond Wash Solution. Peroxide Block reagent (Bond Polymer System/Leica IHC Refine kit, manufactured by Leica Biosystems Nussloch GmbH) was added thereto, and the sample was incubated for 5 minutes. The sample was washed a total of 4 times with Bond Wash Solution and ion-exchanged water. DAB reagent (Bond Polymer System/Leica IHC Refine kit, manufactured by Leica Biosystems Nussloch GmbH) was added thereto, and the sample was incubated for 10 minutes. The sample was washed 4 times with ion-exchanged water. Hematoxylin (Bond Polymer System/Leica IHC Refine kit, manufactured by Leica Biosystems Nussloch GmbH) was added thereto, and the sample was incubated for 5 minutes and then washed a total of 4 times with ion-exchanged water and Bond Wash Solution.

4)-3-5 Staining Using ab58201 Antibody (Anti-FGFR2 Antibody, Abcam Plc.)

Each sample was stained using an automatic staining apparatus (LEICA BOND-III; manufactured by Leica Biosystems Nussloch GmbH). For deparaffinization, the sample was heated to 72° C., then Bond Dewax Solution (manufactured by Leica Biosystems Nussloch GmbH) was added thereto, and the sample was incubated for 30 seconds, followed by addition of ethanol and washing 4 times with Bond Wash Solution (manufactured by Leica Biosystems Nussloch GmbH). Bond Epitope Retrieval Solution 2 (manufactured by Leica Biosystems Nussloch GmbH) was added thereto, and the sample was incubated at 100° C. for 20 minutes. The sample was washed 7 times with Bond Wash Solution. ab58201 was diluted to 2 μg/mL and reacted with the sample for 30 minutes.

The sample was washed 3 times with Bond Wash Solution. Post Primary reagent (Bond Polymer System/Leica IHC Refine kit, manufactured by Leica Biosystems Nussloch GmbH) was added thereto, and the sample was incubated for 8 minutes.

The sample was washed 4 times with Bond Wash Solution. Primary reagent (Bond Polymer System/Leica IHC Refine kit, manufactured by Leica Biosystems Nussloch GmbH) was added thereto, and the sample was incubated for 8 minutes. The sample was washed 4 times with Bond Wash Solution. Peroxide Block reagent (Bond Polymer System/Leica IHC Refine kit, manufactured by Leica Biosystems Nussloch GmbH) was added thereto, and the sample was incubated for 5 minutes. The sample was washed a total of 4 times with Bond Wash Solution and ion-exchanged water. DAB reagent (Bond Polymer System/Leica IHC Refine kit, manufactured by Leica Biosystems Nussloch GmbH) was added thereto, and the sample was incubated for 10 minutes. The sample was washed 4 times with ion-exchanged water. Hematoxylin (Bond Polymer System/Leica IHC Refine kit, manufactured by Leica Biosystems Nussloch GmbH) was added thereto, and the sample was incubated for 5 minutes and then washed a total of 4 times with ion-exchanged water and Bond Wash Solution.

4)-4 Evaluation of Stained Preparation: Binding Specificity for Each Denatured Molecule of FGFR Family The preparations completely stained in Example 4)-3 were dehydrated with ethanol series, cleared with xylene series, and then mounted on glass covers together with mounting agents. The preparations were observed under an optical microscope and evaluated for brown stains representing positive reaction products.

The commercially available antibody 18601 exhibited positive stains on cells forced to express FGFR2 IIIb or FGFR2 IIIc, but exhibited no positive stain on cells forced to express FGFR1 IIIb, FGFR1 IIIc, FGFR3 IIIb, FGFR3 IIIc, and FGFR4, which are other members of the FGFR family, or empty vector-transfected cells (FIGS. 2A to 2D). Furthermore, clear positive stains were observed on many cells in the blocks of SNU-16 cells (FIG. 3-(A)), KATO III cells (FIG. 3-(C)), and NCI-H716 cells (FIG. 3-(B)), demonstrating that these cell lines expressed the FGFR2 protein.

As shown in FIGS. 4A to 4D and FIGS. 5A to 5D, the rat FR2-2nd_#028 and the mouse chimeric FR2-2nd_#028 exhibited very strong stains only on some cells in the blocks of cells forced to express FGFR2 IIIc, but exhibited no positive stain on other forcedly expressing cells or empty vector-transfected cells. Thus, it was concluded that the rat FR2-2nd_#028 and the mouse chimeric FR2-2nd_#028 are capable of specifically staining FGFR2 IIIc. Also, the rat FR2-2nd_#028 and the mouse chimeric FR2-2nd_#028 exhibited clear positive stains on many NCI-H716 cells (FIGS. 6-(B) and 7-(B)) confirmed to express the FGFR2 IIIc protein, but exhibited no positive stain on SNU-16 cells (FIGS. 6-(A) and 7-(A)) and KATO III cells (FIGS. 6-(C) and 7-(C)) expressing no FGFR2 IIIc protein. From these results, the rat FR2-2nd_#028 and the mouse chimeric FR2-2nd_#028 were confirmed to also exhibit positive reaction with cancer cells endogenously having the FGFR2 IIIc protein. As shown in FIG. 8, the rat FR2-2nd_#028 exhibited clear positive stains on many cells in the xenograft tumors derived from NCI-H716 cells. From these results, the rat FR2-2nd_#028 was confirmed to also react with FGFR2 IIIc in the xenograft tumors.

As shown in FIGS. 9A to 9D and FIGS. 10A to 10D, the rat FR2-2nd_#023 and mouse chimeric FR2-2nd_#023 antibodies exhibited no positive stain on cells forced to express FGFR1 IIIb, FGFR1 IIIc, FGFR3 IIIb, FGFR3 IIIc, and FGFR4, which are other members of the FGFR family. Thus, it was concluded that the rat FR2-2nd_#023 and mouse chimeric FR2-2nd_#023 antibodies are capable of specifically staining FGFR2 IIIb or FGFR2 IIIc. As shown in FIGS. 11 and 12, the rat FR2-2nd_#023 and the mouse chimeric FR2-2nd_#023 exhibited clear positive stains on many cells in SNU-16 cells, NCI-H716 cells, and KATO III cells confirmed to express the FGFR2 protein. From these results, the rat FR2-2nd_#023 and the mouse chimeric FR2-2nd_#023 were confirmed to also exhibit positive reaction with cancer cells endogenously having the FGFR2 IIIb or FGFR2 IIIc protein.

The commercially available antibody 18601, a polyclonal antibody, was found to have lot-to-lot variation in staining. On the other hand, the rat FR2-2nd_#023, the mouse chimeric FR2-2nd_#023, the rat FR2-2nd_#028, and the mouse chimeric FR2-2nd_#028 are capable of staining with little variation due to being recombinant monoclonal antibodies. Particularly, the rat FR2-2nd_#023 and the mouse chimeric FR2-2nd_#023 rarely varied. As for stained states, 18601 offered a low contrast in positive images and a poor S/N ratio, as compared with the rat FR2-2nd_#023 and the mouse chimeric FR2-2nd_#023.

On the other hand, as shown in FIGS. 13A to 13D, ab58201 exhibited clear positive stains on many cells forced to express FGFR1 IIIb, FGFR1 IIIc, FGFR3 IIIb, and FGFR3 IIIc, which are other members of the FGFR family, and was therefore confirmed to be unsuitable for the expression analysis of FGFR2 alone.

INDUSTRIAL APPLICABILITY

Use of the antibody provided by the present invention enables the testing or diagnosis of various cancers.
Sequence Listing Free Text
SEQ ID NO: 1: Nucleotide sequence of a primer RG2AR3
SEQ ID NO: 2: Nucleotide sequence encoding the heavy chain variable region of a rat anti-FGFR2 antibody FR2-2nd_#028 (FIG. 14A)
SEQ ID NO: 3: Amino acid sequence of the heavy chain variable region of the rat anti-FGFR2 antibody FR2-2nd_#028 (FIG. 14B)
SEQ ID NO: 4: Nucleotide sequence of a primer RKR5
SEQ ID NO: 5: Nucleotide sequence encoding the light chain variable region of the rat anti-FGFR2 antibody FR2-2nd_#028 (FIG. 14C)
SEQ ID NO: 6: Amino acid sequence of the light chain variable region of the rat anti-FGFR2 antibody FR2-2nd_#028 (FIG. 14D)
SEQ ID NO: 7: Nucleotide sequence encoding the heavy chain variable region of a rat anti-FGFR2 antibody FR2-2nd_#023 (FIG. 15A)
SEQ ID NO: 8: Amino acid sequence of the heavy chain variable region of the rat anti-FGFR2 antibody FR2-2nd_#023 (FIG. 15B)
SEQ ID NO: 9: Nucleotide sequence encoding the light chain variable region of the rat anti-FGFR2 antibody FR2-2nd_#023 (FIG. 15C)
SEQ ID NO: 10: Amino acid sequence of the light chain variable region of the rat anti-FGFR2 antibody FR2-2nd_#023 (FIG. 15D)
SEQ ID NO: 11: DNA fragment comprising a DNA sequence encoding the amino acids of a human κ chain secretory signal sequence and a human κ chain constant region (FIG. 16)
SEQ ID NO: 12: Nucleotide sequence of a primer 3.3-F1
SEQ ID NO: 13: Nucleotide sequence of primer 3.3-R1
SEQ ID NO: 14: Nucleotide sequence comprising a nucleotide sequence (nucleotide positions 26 to 1141) encoding the heavy chain of a mouse chimeric anti-FGFR2 antibody FR2-2nd_#028 (FIG. 17A)
SEQ ID NO: 15: Amino acid sequence of the heavy chain of the mouse chimeric anti-FGFR2 antibody FR2-2nd_#028 (FIG. 17B)
SEQ ID NO: 16: Nucleotide sequence of a primer CM-inf-F
SEQ ID NO: 17: Nucleotide sequence of a primer CM-inf-R
SEQ ID NO: 18: Nucleotide sequence comprising a nucleotide sequence (nucleotide positions 26 to 724) encoding the light chain of the mouse chimeric anti-FGFR2 antibody FR2-2nd_#028 (FIG. 17C)
SEQ ID NO: 19: Amino acid sequence of the light chain of the mouse chimeric anti-FGFR2 antibody FR2-2nd_#028 (FIG. 17D)
SEQ ID NO: 20: Nucleotide sequence comprising a nucleotide sequence (nucleotide positions 26 to 1423) encoding the heavy chain of a mouse chimeric anti-FGFR2 antibody FR2-2nd_#023 (FIG. 18A)
SEQ ID NO: 21: Amino acid sequence of the heavy chain of the mouse chimeric anti-FGFR2 antibody FR2-2nd_#023 (FIG. 18B)
SEQ ID NO: 22: Nucleotide sequence comprising a nucleotide sequence (nucleotide positions 26 to 724) encoding the light chain of the mouse chimeric anti-FGFR2 antibody FR2-2nd_#023 (FIG. 18C)
SEQ ID NO: 23: Amino acid sequence of the light chain of the mouse chimeric anti-FGFR2 antibody FR2-2nd_#023 (FIG. 18D)
SEQ ID NO: 24: Amino acid sequence of the heavy chain CDR1 of the rat anti-FGFR2 antibody FR2-2nd_#028 (FIG. 19)
SEQ ID NO: 25: Amino acid sequence of the heavy chain CDR2 of the rat anti-FGFR2 antibody FR2-2nd_#028 (FIG. 19)
SEQ ID NO: 26: Amino acid sequence of the heavy chain CDR3 of the rat anti-FGFR2 antibody FR2-2nd_#028 (FIG. 19)
SEQ ID NO: 27: Amino acid sequence of the light chain CDR1 of the rat anti-FGFR2 antibody FR2-2nd_#028 (FIG. 19)
SEQ ID NO: 28: Amino acid sequence of the light chain CDR2 of the rat anti-FGFR2 antibody FR2-2nd_#028 (FIG. 19)
SEQ ID NO: 29: Amino acid sequence of the light chain CDR3 of the rat anti-FGFR2 antibody FR2-2nd_#028 (FIG. 19)
SEQ ID NO: 30: Amino acid sequence of the heavy chain CDR1 of the rat anti-FGFR2 antibody FR2-2nd_#023 (FIG. 20)
SEQ ID NO: 31: Amino acid sequence of the heavy chain CDR2 of the rat anti-FGFR2 antibody FR2-2nd_#023 (FIG. 20)
SEQ ID NO: 32: Amino acid sequence of the heavy chain CDR3 of the rat anti-FGFR2 antibody FR2-2nd_#023 (FIG. 20)
SEQ ID NO: 33: Amino acid sequence of the light chain CDR1 of the rat anti-FGFR2 antibody FR2-2nd_#023 (FIG. 20)
SEQ ID NO: 34: Amino acid sequence of the light chain CDR2 of the rat anti-FGFR2 antibody FR2-2nd_#023 (FIG. 20)
SEQ ID NO: 35: Amino acid sequence of the light chain CDR3 of the rat anti-FGFR2 antibody FR2-2nd_#023 (FIG. 20)

The invention claimed is:

1. A monoclonal antibody or an antigen binding fragment thereof,
   wherein the monoclonal antibody consists of
   a heavy chain comprising a complimentary determining region H1 (CDRH1) consisting of the amino acid sequence represented by SEQ ID NO: 30, a CDRH2 consisting of the amino acid sequence represented by SEQ ID NO: 31, and a CDRH3 consisting of the amino acid sequence represented by SEQ ID NO: 32; and
   a light chain comprising a CDRL1 consisting of the amino acid sequence represented by SEQ ID NO: 33, a CDRL2 consisting of the amino acid sequence represented by SEQ ID NO: 34, and a CDRL3 consisting of the amino acid sequence represented by SEQ ID NO: 35.

2. The monoclonal antibody or antigen binding fragment thereof according to claim 1, wherein the monoclonal antibody or antigen binding fragment thereof specifically binds to non-denatured human fibroblast growth factor receptor 2 (hFGFR2) IIIb and denatured hFGFR2 IIIb in a preparation fixed in formalin.

3. The monoclonal antibody or antigen binding fragment thereof according to claim 1, wherein the monoclonal antibody comprises a heavy chain variable region and a light chain variable region described in any one of the following (i) to (iv):
   (i) a heavy chain variable region of SEQ ID NO: 8 and a light chain variable region of SEQ ID NO: 10;
   (ii) a heavy chain variable region in which the framework region of the heavy chain variable region is 95% of more identical to the framework region of SEQ ID NO: 8 and a light chain variable region in which the framework region of the light chain variable region is 95% of more identical to the framework region of SEQ ID NO: 10;
   (iii) a heavy chain variable region derived from SEQ ID NO: 8 by incorporating a substitution, deletion, insertion, or addition of 1 or more amino acids into the framework region, and a light chain variable region derived from SEQ ID NO: 10 by incorporating a substitution, deletion, insertion, or addition of 1 or more amino acids into the framework region; and
   (iv) a heavy chain variable region encoded by a polynucleotide that hybridizes under stringent conditions to a polynucleotide that encodes SEQ ID NO: 8, and a light chain variable region encoded by a polynucleotide that hybridizes under stringent conditions to a polynucleotide that encodes SEQ ID NO: 10.

4. The monoclonal antibody or antigen binding fragment thereof according to claim 1, wherein the monoclonal antibody comprises the amino acid sequence of a heavy chain represented by SEQ ID NO: 21 and the amino acid sequence of a light chain represented by SEQ ID NO: 23.

5. The monoclonal antibody or antigen binding fragment thereof which has the following properties (i) to (iii):
   (i) specifically binds to non-denatured human fibroblast growth factor receptor 2 (hFGFR2) IIIc;
   (ii) specifically binds to none of the following: non-denatured human fibroblast growth factor receptor 1 (hFGFR1); non-denatured human fibroblast growth factor receptor 3 (hFGFR3); and non-denatured human fibroblast growth factor receptor 4 (hFGFR4); and
   (iii) specifically binds to denatured hFGFR2 IIIc in a preparation fixed in formalin, wherein the monoclonal antibody or antigen binding fragment thereof binds to a site on hFGFR2 IIIc and/or hFGFR2 IIIb which is recognized by an antibody or an antigen binding fragment thereof according to claim 1 or competes with an antibody or an antigen binding fragment thereof according to claim 1 for binding to hFGFR2 IIIc and/or hFGFR2 IIIb.

6. A monoclonal antibody or an antigen binding fragment thereof which is obtained by a method with comprising the following steps (i) and (ii):
   (i) culturing a cell comprising a polynucleotide encoding a monoclonal antibody according to claim 1 or a vector comprising a polynucleotide encoding a monoclonal antibody according to claim 1; and
   (ii) recovering the monoclonal antibody or antigen binding fragment thereof from the cultures of step (i).

7. A composition comprising a monoclonal antibody or an antigen binding fragment thereof according to claim 1.

8. A composition comprising a monoclonal antibody or an antigen binding fragment thereof according to claim 1, wherein the composition can detect or assay for hFGFR2 IIIc and hFGFR2 IIIb in a tissue preparation which is paraffin-embedded and then deparaffinized, the tissue preparation comprising the monoclonal antibody or antigen binding fragment thereof according to claim 1.

9. The composition comprising a monoclonal antibody or an antigen binding fragment thereof according to claim 1, wherein the composition can detect or assay for hFGFR2 IIIc in a tissue preparation paraffin-embedded and then deparaffinized, the tissue preparation comprising the monoclonal antibody or antigen binding fragment thereof according to claim 1.

10. The composition according to claim 9, wherein the preparation is subjected to enzymatic treatment following the deparaffinization treatment.

11. The composition according to claim 10, wherein the enzymatic treatment is the reaction of protease at 20 to 38° C.

12. A pharmaceutical composition comprising an antibody specifically binding to hFGFR2 IIIc and hFGFR2 IIIb or an antigen binding fragment thereof according to claim 1.

13. A pharmaceutical composition comprising an antibody specifically binding to hFGFR2 IIIc or an antigen binding fragment thereof according to claim 1.

14. A kit for testing or diagnosing a hFGFR2 IIIc- and hFGFR2 IIIb-positive patient, comprising an antibody or an antigen binding fragment of the antibody according to claim 1.

15. The kit according to claim 14, wherein the testing or diagnosing is for cancer.

16. A method for detecting or assaying hFGFR2 IIIc and hFGFR2 IIIb, comprising the following step (i) or steps (i) and (ii):
   (i) contacting a monoclonal antibody or an antigen binding fragment of the antibody according to claim 1 or a composition comprising a monoclonal antibody or an antigen binding fragment thereof according to claim 1 with a test preparation; and
   (ii) determining the test preparation to be positive when hFGFR2 IIIc and hFGFR2 IIIb are detected or assayed in the test preparation or when the expression levels of hFGFR2 IIIc and hFGFR2 IIIb in the test preparation are equivalent to or higher than predetermined references;
   and determining the test preparation to be negative when neither hFGFR2 IIIc nor hFGFR2 IIIb is detected or assayed in the test preparation or when the expression levels of hFGFR2 IIIc and hFGFR2 IIIb in the test preparation are equivalent to or lower than the predetermined references.

17. A method for identifying a suitable individual for treating with a pharmaceutical composition comprising an antibody specifically binding to hFGFR2 or an antigen binding fragment of the antibody, the method comprising the following step (i) or steps (i)-(iii):
   (i) contacting an antibody or an antigen binding fragment of the antibody according to claim 1 or a composition comprising a monoclonal antibody or an antigen binding fragment thereof according to claim 1 with an individual-derived sample;
   (ii) determining the individual to be positive when hFGFR2 IIIc and hFGFR2 IIIb are detected or assayed in the individual-derived sample or when the expression levels of hFGFR2 IIIc and hFGFR2 IIIb in the individual-derived sample are equivalent to or higher than predetermined references, and determining the individual to be negative when neither hFGFR2 IIIc nor hFGFR2 IIIb is detected or assayed in the individual-derived sample or when the expression levels of hFGFR2 IIIc and hFGFR2 IIIb in the individual-derived sample are equivalent to or lower than the predetermined references; and
   (iii) treating the individual who is determined to be positive with the pharmaceutical composition.

18. The method according to claim 17, wherein the method is used in a method for testing or diagnosing a hFGFR2 IIIc- and hFGFR2 IIIb-positive patient.

19. The method according to claim 18, wherein the testing or diagnosing is for cancer.

20. A method for detecting or assaying hFGFR2 IIIc, comprising the following steps (i) to (iii):
   (i) contacting a composition comprising an antibody or an antigen binding fragment of the antibody according to claim 1 with a test preparation to detect or assay hFGFR2 IIIb and hFGFR2 IIIc in the test preparation;
   (ii) contacting a composition comprising an antibody specifically binding to hFGFR2 IIIb or an antigen binding fragment of the antibody with the test preparation to detect or assay hFGFR2 IIIb in the test preparation; and (iii) comparing the results of the detection or assay in step (i) with the results of the detection or assay in step (ii) or subtracting the results of the detection or assay in step (ii) from the results of the detection or assay in step (i) to obtain detection or assay results or value of hFGFR2 IIIc in the sample.

21. A method for treating a patient that is positive for hFGFR2 IIIc- and hFGFR2 IIIb, comprising administering a pharmaceutical composition comprising an antibody or antigen binding fragment thereof according to claim 1 to a patient in need thereof.

* * * * *